United States Patent [19]
Lee et al.

[11] Patent Number: 5,658,885
[45] Date of Patent: Aug. 19, 1997

[54] AMIDINO AND GUANIDINO SUBSTITUTED BORONIC ACID INHIBITORS OF TRYPSIN-LIKE ENZYMES

[75] Inventors: Sheng-Lian O. Lee, West Chester, Pa.; David John Carini, Wilmington, Del.; John Matthew Fevig, New London, Pa.; Charles Adrian Kettner, Wilmington, Del.; Padmaja Mantri, Bombey, India; Zixia Feng, Wilmington, Del.

[73] Assignee: The DuPont Merck Pharmaceutical Company, Wilmington, Del.

[21] Appl. No.: 329,039

[22] Filed: Oct. 25, 1994

Related U.S. Application Data

[63] Continuation-in-part of Ser. No. 204,055, Mar. 2, 1994, abandoned, which is a continuation-in-part of Ser. No. 052,835, Apr. 27, 1993, abandoned.

[51] Int. Cl.⁶ ..................... A61K 38/05; C07C 241/00
[52] U.S. Cl. ................... 514/19; 514/13; 514/14; 514/15; 514/16; 514/17; 514/18; 530/326; 530/327; 530/328; 530/329; 530/330; 530/331; 562/560
[58] Field of Search ............... 514/16–19; 530/326–331; 562/560

[56] References Cited

U.S. PATENT DOCUMENTS 5,371,072  12/1994  Webb ........................................ 514/18

FOREIGN PATENT DOCUMENTS 0293881  7/1988  European Pat. Off. .......... C07K 5/00
9425051  11/1994  WIPO ............................. A61K 37/02

OTHER PUBLICATIONS

Iwanowicz, Bioorg Med Chem Lett 2, 1607, 1992.

*Primary Examiner*—Cecilia J. Tsang
*Assistant Examiner*—David Lukton

[57] ABSTRACT

This invention relates to Novel α-aminoacid and α-aminoboronic acid and corresponding peptide analogs of the following formula:

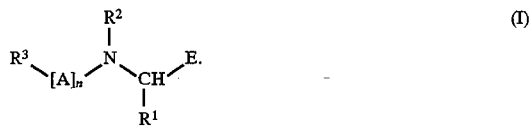

15 Claims, No Drawings

AMIDINO AND GUANIDINO SUBSTITUTED BORONIC ACID INHIBITORS OF TRYPSIN-LIKE ENZYMES

CROSS REFERENCE TO RELATED APPLICATIONS

This application is a continuation-in-part of application Ser. No. 08/204,055, filed Mar. 2, 1994, now abandoned which is a continuation-in-part of application Ser. No. 08/052,835, filed Apr. 27, 1993, now abandoned.

FIELD OF THE INVENTION

The present invention relates generally to α-amino acids and α-aminoboronic acids and corresponding peptide analogs in which the alpha carbon is substituted with an aromatic guanidino, amidino group, halogen, cyano group, aliphatic amidino, formamidino group, or other neutral group.

BACKGROUND OF THE INVENTION

Simple boronic acids are inhibitors of serine proteases. For example, Koehler et al. *Biochemistry* 10: 2477 (1971) reports that 2-phenylethane boronic acid inhibits chymotrypsin at millimolar levels. The synthesis of boronic acid analogs of N-acyl-α-amino acids has yielded more effective inhibitors. Ac-boroPhe—OH, R-1-acetamido-2-phenylethane boronic acid, inhibits chymotrypsin with a $K_i$ of 4 μM Matteson et al. *J. Am. Chem. Soc.* 103: 5241 (1981). More recently, Shenvi, U.S. Pat. No. 4,537,773 (1985) disclosed that boronic acid analogs of α-amino acids, containing a free amino group, were effective inhibitors of aminopeptidases. Shenvi, U.S. Pat. No. 4,499,082 (1985) discloses that peptides containing an α-aminoboronic acid with a neutral side chain were more effective inhibitors of serine proteases exceeding inhibitors disclosed earlier by as much as 3 orders of magnitude in potency. The chemistry of α-aminoboronic acids was further expanded to the synthesis of peptide analogs containing boronic acid with positive charged sidechains, boroLysine, boroArginine, boroOrnithine, and isothiouronium analogs (EPA 0 293 881, Dec. 7, 1988). This series of compounds have provided highly effective inhibitors of thrombin and other trypsin-like enzymes. The boroArginine analogs specifically designed as thrombin inhibitors are highly effective in the inhibition of blood coagulation both in vitro and in vivo. In the present invention, this group of compounds is extended to aliphatic amidino and formamidino, to aromatic amidino and guanidino, to cyano and halogen, and to other neutral substituted aromatic boronic acid analogs.

It should be noted that additional boronic acids have been disclosed. Metternich (EP 0471651) have described peptides containing boroArginine and boroLysine which contain at least one unnatural amino acid residue. Elgendy et al. *Tetrahedron Lett.*, 33, 4209–4212 (1992) have described peptides containing α-aminoboronic acids with aliphatic neutral sidechains which are thrombin inhibitors. Kakkar in (WO 92/07869) has claimed peptide thrombin inhibitors of the general structure, X-Aa$_1$-Aa$_2$-NH-CH(Y)-Z where Aa$_1$ and Aa$_2$ are unnatural amino acid residues. Z is —CN, —COR, —B(R$^2$)(R$^3$), -P(O)(R)(R), and Y is —[CH$_2$]$_n$-Q or —CH$_2$-Ar-Q where Q=H, amino, amidino, imidazole, guanidino or isothioureido and n=1–5 and where R$_2$ and R$_3$ are the same or different and are selected from the group consisting of OH, OR$^6$, and NR$^6$R$^7$, or R$^2$ and R$^3$ taken together represent the residue of a diol. This specialized group of compounds where Z is -B(R$^2$)(R$^3$) fall within the scope of our present application. It should be noted that this is a narrow subset of Kakkar et al. However, rather specialized chemical transformations are required to prepare these compounds and Kakkar et al. does not make an enabling disclosure.

SUMMARY OF THE INVENTION

A compound of formula (I)

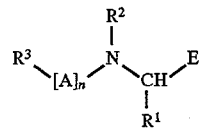

wherein

E is
  a) —BY$^1$Y$^2$,
  b) —C(=O)R$^{14}$;
  c) —C(=O)OR$^4$,
  d) —C(=O)NR$^{15}$R$^{16}$,
  e) —C(=O)R$^4$, or
  f) —C(=O)COOR$^4$;

Y$^1$ and Y$^2$ are
  a) —OH,
  b) -F,
  c) -NR$^4$R$^5$,
  d) C$_1$–C$_8$ alkoxy, or
  when taken together Y$^1$ and Y$^2$ form:
  e) a cyclic boron ester where said chain or ring contains from 2 to 20 carbon atoms and, optionally, 1–3 heteroatoms which can be N, S, or O,
  f) a cyclic boron amide where said chain or ring contains from 2 to 20 carbon atoms and, optionally, 1–3 heteroatoms which can be N, S, or O,
  g) a cyclic boron amide-ester where said chain or ring contains from 2 to 20 carbon atoms and, optionally, 1–3 heteroatoms which can be N, S, or O;

Y$^3$ and Y$^4$ are
  a) —OH,
  b) —H, or
  c) -F;

R$^1$ is
  a) C1–C12-alkyl is optionally substituted with —CN, —OR$^2$, —C(NH)NHR$^6$, —NHC(NH)NHR$^6$, —SC(NH)NHR$^6$, —NHC(NH) NHOH, —NHC(NH)NHC(O)R$^6$, —NHS(O) ,R$^4$, —NHC(O)NHR$^4$, —NHC(O)R$^4$, —NHC(O)CH(OH) R$^4$, —NHC(=NCN)—SR$^6$, —NHC(=NCN)NHR$^6$, —ONHR$^6$, —NHC(=NR$^6$)H, —ONHC(=NCN)NHR$^6$, —ONHC(=NH)NHR$^6$, —ONHC(=NR$^6$)H, —ONHC(=NH)NHOH, —C(NH)NHC(O)R$^6$, —SC(NH)NHC(O)R$^6$, —NHC(=NCN)NHC(O)R$^6$, —ONHC(O)R$^6$, —NHC(=NC (O)R$^6$)H, —ONHC(=NCN)NHC(O)R$^6$, —ONHC(=NH)NHC(O)R$^6$, —ONHC(=NC(O)R$^6$)H, —C(NH)NHC(O)OR$^6$, —NHC(NH)NHC(O)OR$^6$, —SC(NH)NHC(O)OR$^6$, —NHC(=NCN)NHC(O)OR$^6$, —ONHC(O)OR6, —NHC(=NC(O)OR$^6$)H, —ONHC(=NCN)NHC(O)OR$^6$, —ONHC(=NH)NHC(O)OR$^6$, —NHC(O)OR$^4$, —NHC(NH)NHC(O)OR$^6$, or —ONHC(=NC(O)OR$^6$)H;

b)

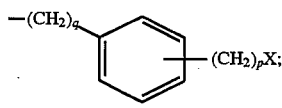

c)

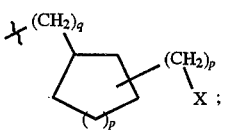

or d)

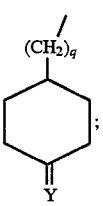

X is
  a) halogen (F, Cl, Br, I)
  b) —CN,
  c) —NO$_2$,
  d) —CF$_3$,
  e) —NH$_2$
  f) —NHC(NH)H,
  g) —NHC(NH)NHOH,
  h) —NHC(NH)NHCN,
  i) —NHC(NH)NHR$^6$,
  j) —NHC(NH)NHCOR$^6$,
  k) —C(NH)NHR$^6$,
  l) —(NH)NHCOR$^6$,
  m) —C(O)NHR$^2$,
  n) —CO$_2$R$^2$,
  o) —OR$^2$,
  p) —OCF$_3$,
  q) —SC(NH)NHR$^6$,
  r) —NHS(O)$_r$R$^4$,
  s) —NHC(O)NHR$^4$,
  t) —NHC(O)R$^4$,
  u) —NHC(O)CH(OH) R$^4$,
  v) —NHC(=NCN)—SR$^6$,
  w) —NHC(=NCN)NHR$^6$,
  x) —NHC(=NR$^6$)H,
  y) —ONHR$^6$,
  z) —ONHC(=NCN)NHR$^6$,
  aa) —ONHC(=NH)NHR$^6$,
  ab) —ONHC(=NH)H,
  ac) —ONHC(=NR$^6$)H, or
  ad) —ONHC(=NH)NHOH;

Y is =O, =NOH, or =N—NHC(=O)H;

R$^2$ is
  a) H,
  b) optionally substituted C1–C12-alkyl,
  c) optionally substituted cycloalkyl,
  d) optionally substituted aryl, where aryl is phenyl or napthyl, or
  e) optionally substituted -C1–C4-alkylaryl, where aryl is defined above;
  where the groups C1–C12-alkyl, cycloalkyl, and -C1–C4-alkylaryl optionally contain in-chain heteroatoms (O, N, S) and the groups C1–C12-alkyl, cycloalkyl, aryl, and -C1–C4-alkylaryl are optionally substituted with one or two substituents selected from the group consisting of:
    halo (F, Cl, Br, I), C1–C4-alkyl, C1–C4-alkoxy, —NO$_2$, —CF$_3$, —S(O)$_r$-C1–C4-alkyl, —OH, —NH$_2$, —NH (C1-C4-alkyl), —N (C1–C4-alkyl)$_2$, or —CO$_2$R$^4$;

R$^3$ is H, alkyl, aryl, alkylaryl, —S(O)$_r$—R$^7$, —C(=O)R$^7$, —C(=O)OR$^7$, —P(O)$_2$OR$^7$ or any other NH$_2$ blocking group comprised of 1–20 carbon atoms;

R$^4$ and R$^5$ are independently:
  a) hydrogen,
  b) C$_1$–C$_4$ alkyl,
  c) -(C$_1$–C$_4$ alkyl)-aryl, or
  d) C$_5$–C$_7$ cycloalkyl;

R$^6$ is
  a) H,
  b) C1–C4-alkyl,
  c) aryl, wherein aryl is phenyl or napthyl optionally substituted with one or two substituents selected from the group consisting of:
    halo (F, Cl, Br, I), C1–C4-alkyl, C1–C7-alkoxy, —NO$_2$, —CF3, —S(O)$_r$-C1–C4-alkyl, —OH, —NH$_2$, —NH (C1-C4-alkyl), —N (C1–C4-alkyl)$_2$, and —CO$_2$R$^4$: or
  d) -C1–C4-alkylaryl, where aryl is as defined above;

R$^7$ is
  a) H,
  b) C1–C4-alkyl,
  c) aryl, wherein aryl is phenyl or napthyl optionally substituted with one or two substituents selected from the group consisting of:
    halo, C1–C4-alkyl, C1–C7-alkoxy, —NO$_2$, —CF$_3$, —S (O)$_r$-C1–C4-alkyl, —OH, —NH$_2$, —NH (C1–C4-alkyl, -N (C1–C4-alkyl)$_2$, and —CO$_2$R$^4$: or
  d) -C1–C4-alkylaryl, where aryl is as defined above;

R$^{13}$ is:
  a) hydrogen
  b) halogen,
  c) C$_1$–C$_4$ alkyl,
  d) C$_1$–C$_4$ alkoxy,
  e) methylenedioxy,
  f) —NO$_2$,
  g) —CF$_3$,
  h) -SH,
  i) —S(O)$_r$—(C$_1$–C$_4$ alkyl),
  j) —CN,
  k) —OH,
  l) —NH$_2$,
  m) —NH (C$_1$–C$_4$ alkyl),
  n) -N(C$_1$–C$_4$ alkyl)$_2$,
  o) —NHC(=O)R$^4$, or
  p) —(CH$_2$)$_p$—CO$_2$R$^4$;

R$^{14}$ is:
  a) —CF$_3$,
  b) —CHF$_2$,
  c) —CH$_2$F,
  d) —CH$_2$Cl,
  e) —C(=O)OR$^4$,
  f) —C(=O)NR$^{15}$R$^{16}$,
  g) —C(=O)R$^4$,
  h) —C(=O)COOR$^4$,
  i) —C(=O)C(=O)NR$^{15}$R$^{16}$,
  j) —C(=O)C(=O)R$^4$, k) -CY³Y⁴COOR⁴,
l) -CY³Y⁴C(=O)NR¹⁵R¹⁶,
m) -CY³Y⁴C(=O)R⁴,
n) -CH₂Br,
o)

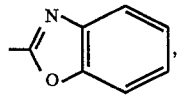

p)

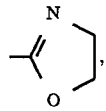

or q) heterocycle;

R¹⁵ and R¹⁶ are independently:
a) hydrogen,
b) $C_1$–$C_4$ alkyl,
c) -($C_1$–$C_4$ alkyl)-aryl,
d) $C_5$–$C_7$ cycloalkyl, or
e) phenyl, optionally substituted by R¹³;

R¹⁵ and R¹⁶ can be taken together to form a ring:
a)

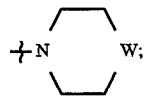

W is
a) —O—,
b) —S(O)$_r$—,
c) -(CH₂)$_n$-,
d) —NR⁴—,
e) a bond, or
f) —NC(=O)R⁴—;

A is an amino acid residue or a peptide comprised of 2–20 amino acid residues;

n is 0 or 1;

p is 0 to 3;

q is 0 to 4;

r is 0 to 2;

and pharmaceutically acceptable salts thereof, with the proviso that when R¹ is aliphatic, the R⁶ substituent on —NHC(NH)NHR⁶ cannot be H.

Preferred are those compounds of the formula (I) where:

R¹ is
a) C1–C12-alkyl is optionally substituted with —OR², —C(NH)NHR⁶, —NHC(NH)H, —NHC(NH)NHR⁶, —NHC(NH)NHOH, —NHS(O)$_r$R⁴, —NHC(O)NHR⁴, —NHC(O)R⁴, —NHC(O)CH(OH)R⁴, —NHC(=NCN)—SR⁶, —NHC(=NCN)NHR⁶, —ONHR6, —NHC(=NR⁶)H, —ONHC(=NCN)NHR⁶, —ONHC(=NH)NHR⁶, —ONHC(=NH)H, —ONHC(=NR⁶)H, or —ONHC(=NH)NHOH;

b)

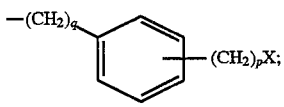

c)

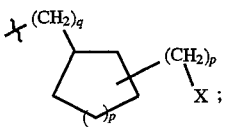

or d)

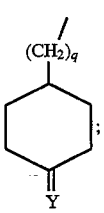

X is
a) halogen (F, Cl, Br, I)
b) —CN,
c) —NO₂,
d) —CF₃,
e) —NH₂
f) —NHC(NH)H,
g) —NHC(NH)NHOH,
h) —NHC(NH)NHCN,
i) —NHC(NH)NHR⁶,
j) —C(NH)NHR⁶,
k) —C(O)NHR²,
l) —CO₂R²,
m) —OR²,
n) —OCF₃,
o) -SC(NH)NHR⁶,
p) —NHS(O)$_r$R⁴,
q) —NHC(O)NHR⁴,
r) —NHC(O)R⁴,
s) —NHC(O)CH(OH)R⁴,
t) —NHC(=NCN)NHR⁶,
u) —NHC(=NR⁶)H,
v) —ONHR6,
w) —ONHC(=NCN)NHR⁶,
x) —ONHC(=NH)NHR⁶,
y) —ONHC(=NH)H,
z) —ONHC(=NR⁶)H, or
aa) —ONHC(=NH)NHOH;

R¹⁴ is:
a) —CF₃,
b) —CHF₂,
c) —CH₂F,
d) —C(=O)OR⁴,
e) —C(=O)NR¹⁵R¹⁶,
f) —C(=O)R⁴, g)

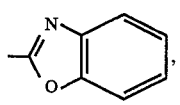

h)

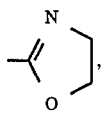

or i) heterocycle;
and all other substituents are as defined above.

More preferred are those compounds of the formula (I) where:

$Y^3$ and $Y^4$ are —OH;

$R^1$ is
  a) C1–C12-alkyl is optionally substituted with —$OR^2$, —C(NH)$NHR^6$, —NHC(NH)H, —NHC(NH)$NHR^6$, —NHS(O)$_r R^4$, —NHC(O)$NHR^4$, —NHC(O)$R^4$, —NHC(O)CH(OH)$R^4$, —NHC(=NCN)—$SR^6$, —NHC(=NCN)$NHR^6$, —ONHR6, or —ONHC(=NH)$NHR^6$;

b)

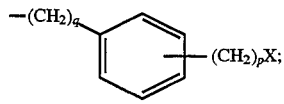

c)

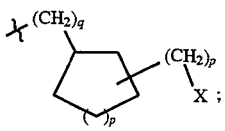

or d)

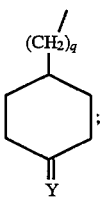

X is
  a) halogen (Br)
  b) —CN,
  c) —$NH_2$
  d) —NHC(NH)H,
  e) —NHC(NH)$NHR^6$,
  f) —C(NH)$NHR^6$,
  g) —C(O)$NHR^2$,
  h) —$CO_2 R^2$,
  i) —$OR^2$, or
  j) —NHC(=$NR^6$)H;

$R^{14}$ is:
  a) —$CF_3$,
  b) —$CHF_2$,
  c) —$CH_2F$, d) —C(=O)$OR^4$,
  e) —C(=O)$NR^{15}R^{16}$,
  f)

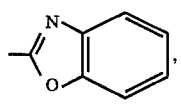

g)

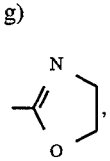

or h) heterocycle;
and all other substituents are as defined above.

Most preferred are those compounds of the formula (I) where:

E is -$BY^1Y^2$;

$Y^1$ and $Y^2$ are
  a) —OH,
  when taken together $Y^1$ and $Y^2$ form:
  b) a cyclic boron ester where said chain or ring contains from 2 to 20 carbon atoms and, optionally, 1–3 heteroatoms which can be N, S, or O;

$Y^3$ and $Y^4$ are —OH;

$R^1$ is
  a) C1–C12-alkyl is optionally substituted with —C(NH)$NHR^6$, —NHC(NH)H, —NHC(NH)$NHR^6$, —$ONHR^6$, or —ONHC(=NH)$NHR^6$;

b)

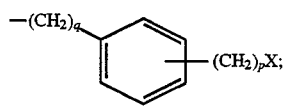

c)

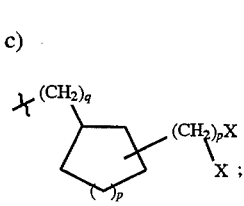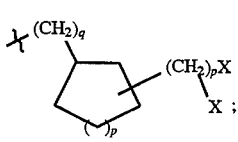

or d)

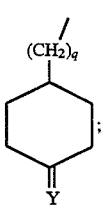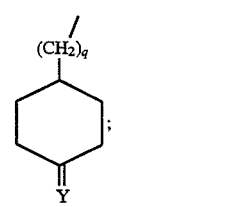

X is
  a) —CN,
  c) —$NH_2$
  d) —NHC(NH)H,
  e) —NHC(NH)$NHR^6$,
  f) —C(NH)$NHR^6$,
  g) —C(O)$NHR^2$,
  h) —$CO_2R^2$, i) —OR², or
j) —NHC(=NR⁶)H;

Y is =O;

and all other substituents are as defined above.

Specifically preferred compounds of this invention are the following:

Ac-(D)Phe-Pro-NH-CH[(CH₂)₄CN]BO₂-C₁₀H₁₆
Ac-(D)Phe-Pro-NHCH[(CH₂)₄C(NH)NH₂]BO₂-C₁₀H₁₆
Ac-(D)Phe-Pro-NHCH[(CH₂)₃-NHC(NH)H]B(OH)₂
Boc-(D)Phe-Pro-NHCH[(CH₂)₃-NHC(NH)H]B(OH)₂
Ac-(D)Phe-Pro-boroPhe[m-C(NH)NH₂]-C₁₀H₁₆
Ac-(D)Phe-Pro-boroPhe(m-CH₂NH₂)-C₁₀H₁₆
Ac-(D)Phe-Pro-boroPhe(m-Br)-C₁₀H₁₆
Ac-(D)Phe-Pro-boroPhe(p-CN)-C₁₀H₁₆
Boc-(D)Phe-Pro-boroPhe(m-CN)-C₁₀H₁₆
Ac-(D)Phe-Pro-boroArg(CN)-C₁₀H₁₆
N,N-(CH₃)₂-(D)Phe-Pro-boroPhe(m-CN)—OH·HCl
Ac-(D)Phe-Pro-boroPhe(m-CN)—OH·HCl
Ms-(D)Phe-Pro-boroPhe(m-CN)—OH·HCl
Boc-(D)Thiazolylalanine-Pro-boroPhe(m-CN)-C₁₀H₁₆
Boc-(D)3-Pyridylalanine-Pro-boroPhe(m-CN)-C₁₀H₁₆
Ms-(D)3-Pyridylalanine-Pro-boroPhe(m-CN)-C₁₀H₁₆
Boc-(D)2-Pyridylalanine-Pro-boroPhe(m-CN)-C₁₀H₁₆
Boc-(D)2-Thienylalanine-Pro-boroPhe(m-CN)-C₁₀H₁₆
Ms-(D)2-Thienylalanine-Pro-boroPhe(m-CN)-C₁₀H₁₆
Boc-(D)Phe-Aze-boroPhe(m-CN)C₁₀H₁₆
Hydrocinnamoyl-Pro-boroIrg(CH₃)—OH·HBr
Ac-(D)Phe-Pro-boroArg(CH₃)—OH·HCl
PhCH₂SO₂-(D)Phe-Pro-boroOrn(CH=NH )—OH·HCl
CH₃CH₂CH₂SO₂-(D)Phe-Pro-boroOrn(CH=NH)—OH·HCl
CH₃CH₂CH₂SO₂-(D)Phe-Pro-boroArg(CH₃)—OH·HCl
Ac-(D)Phe-Sar-boroOrn(CH=NH)—OH·HCl
Boc-(D)Phe-Sar-boroPhe(mCN)-C₁₀H₁₆
Boc-(D)Phe-Aze-boroOrn(CH=NH)—OH·HCl
4-(Phenyl)benzoyl-boroOrn(CH=NH)-C₁₀H₁₆·HCl
Ac-(D)Phe-Pro-boroOrn(CH=NH)]-C₁₀H₁₆·HCl
Boc-Pro-boroOrn(CH=NH)-C₁₀H₁₆·HCl
Boc-(D)Phe-Pro-boroOrn(CH=NH)]-C₁₀H₁₆·0.5 HCl·0.5 BSA
H-(D)Phe-Pro-boroOrn(CH=NH)]-C₁₀H₁₆·0.5 HCl·0.5 BSA
H-(D)Phe-Pro-boroOrn(CH=NH)]—OH·0.65 HCl·0.35 BSA
H-boroPhe(mCN)-C₁₀H₁₆·HCl
Ac-(D)Phe-Pro-boroPhe-(m-CN)-C₁₀H₁₆
H-(D)Phe-Pro-boroPhe-(m-CN)-C₁₀H₁₆·HCl
H-(D)Phe-Pro-boroPhe-(m-CN)—OH·HCl
N,N-(CH₃)₂-(D)Phe-Pro-boroPhe-(m-CN)—OH·HCl (ISOMER I)
Ac-(D)Phe-Pro-boroPhe-(p-CH₂NH₂)-C₁₀H₁₆·BSA
Ac-(D)Phe-Pro-boroPhe-(p-C(NH)NH₂)-C₁₀H₁₆·BSA
N-CH₃-(D)Phe-Pro-boroPhe-(m-CN)-C₁₀H₁₆·HCl
H-Pro-boroPhe-(m-CN)-C₁₀H₁₆·HCl
H-(D)Thiazolylalanine-Pro-boroPhe-(m-CN)-C₁₀H₁₆·HCl
H-(D)3-Pyridylalanine-Pro-boroPhe-(m-CN)-C₁₀H₁₆·HCl
Ms-(D)Thiazolylalanine-Pro-boroPhe-(m-CN)-C₁₀H₁₆
N-Boc-N-CH₃-(D)Phe-Pro-boroPhe-(m-CN)-C₁₀H₁₆
Ac-Pro-boroPhe-(m-CN)-C₁₀H₁₆
H-(D)2-Pyridylalanine-Pro-boroPhe-(m-CN)-C₁₀H₁₆·HCl
H-(D)2-Thienylalanine-Pro-boroPhe-(m-CN)-C₁₀H₁₆·HCl
Ms-(D)2-Pyridylalanine-Pro-boroPhe-(m-CN)-C₁₀H₁₆
(2-Pyrimidylthio)acetyl-Pro-boroPhe-(m-CN)-C₁₀H₁₆
trans-3-(3-pyridyl)acryl-Pro-boroPhe-(m-CN)-C₁₀H₁₆
(4-Pyridylthio)acetyl-Pro-boroPhe-(m-CN)-C₁₀H₁₆
Succinyl-(D)Phe-Pro-boroPhe-(m-CN)—OH
3-Pyridylpropionyl-Pro-boroPhe-(m-CN)-C₁₀H₁₆
Boc-(D)Phe-Aze-boroPhe-(m-CN)-C₁₀H₁₆
H-(D)Phe-Aze-boroPhe-(m-CN)-C₁₀H₁₆·HCl
Hydrocinnamoyl-Pro-boroOrn(CH=NH)]OH·BSA
Hydrocinnamoyl-Pro-boroIrg(CH₂CH=CH₂)—OH·HBr
Hydrocinnamoyl-ProboroGly[(CH₂)4-NH-Acetyl]C₁₀H₁₆
Cbz(D)Phe-Pro-boroIrg(CH₃)-C₁₀H₁₆·HBr
Ac-(D)Phe-Pro-boroIrg(CH₃)—OH·HBr
Hydrocinnamoyl-Pro-boroIrg(CH₂CH₃)—OH·HBr
Ac-(D)Phe-Pro-boroArg(CH₃)—OH·HCl
Hydrocinnamoyl-Pro-boroArg(CH₃)—OH·HCl
Ms-(D)Phe-Pro-boroArg(CH₃)—OH·HCl
Ms-(D)Phe-Pro-boroOrn(CH=NH)—OH·HCl
PhSO₂-(D)Phe-Pro-boroArg(CH₃)—OH·HCl
PhSO₂-(D)Phe-Pro-boroOrn(CH=NH)—OH·HCl
Ms-(D)Phe(4-fluoro)-Pro-boroOrn(CH=NH)—OH·HCl
PhCH₂SO₂-(D)Phe-Pro-boroArg(CH₃)—OH·HCl
PhCH₂SO₂-(D)Phe-Pro-boroOrn(CH=NH)—OH·HCl
CH₃CH₂CH₂SO₂-(D)Phe-Pro-boroOrn(CH=NH)—OH·HCl
CH₃CH₂CH₂SO₂-(D)Phe-Pro-boroArg(CH₃)—OH·HCl
CH₃(CH₂)₃SO₂-(D)Phe-Pro-boroArg(CH₃)—OH·HCl
CH₃(CH₂)₃SO₂-(D)Phe-Pro-boroOrn(CH=NH)—OH·HCl
Z-(D)Phe-Pro-boroOrn(CH=NH)—OH·HCl
Boc-(D)Phe-Pro-boroGly[(CH₂)₃—ONH₂]—OH·HCl
PhCH₂SO₂-(D)Phe-Pro-boroGly[(CH₂)₃—ONH₂]-C₁₀H₁₆·HCl
Boc-(D)Phe-Pro-boroGly[(CH₂)₃—ONHC(=NH)NH₂]-C₁₀H₁₆·HCl
Boc-(D)Phe-Pro-boroOrn-[C(NCN)NHCH₃]-C₁₀H₁₆
HOOCCH₂-(D)Phe-Pro-boroOrn[C(NCN)NHCH₃]-C₁₀H₁₆·HCl
Boc-(D)Phe-Pro-boroOrn[C(NCN)SCH₃]-C₁₀H₁₆
BoC-(D)Phe-Pro-boroOrn(CONH₂)-C₁₀H₁₆
H-(D)Phe-Pro-boroOrn(CONH₂)-C₁₀H₁₆·HCl
PhCH₂SO₂-(D)Phe-Pro-boroOrn(CONH₂)-C₁₀H₁₆
HOOCCH₂-(D)Phe-Pro-boroOrn(CONH₂)-C₁₀H₁₆·HCl
BoC-(D)Phe-Pro-boroOrn(COCH₂OH)-C₁₀H₁₆
BoC-(D)Phe-Pro-boroOrn(N-Methanesulfonyl)-C₁₀H₁₆
H-(D)Phe-Pro-boroOrn(N-Methanesulfonyl)-C₁₀H₁₆·HCl
4-(N-Acetyl)Anilinesulfonyl-(D)Phe-Pro-boroOrn(N-Methanesulfonyl)-C₁₀H₁₆ Methanesulfonyl-(D)Phe-Pro-boroOrn(N-Methanesufonyl)-C₁₀H₁₆
N,N-dimethyl-(D)Phe-Pro-boroOrn-(N-Methanesulfonyl)-C₁₀H₁₆·HCl
Ac-Gly-(D)Phe-Pro-boroOrn (N-Methanesulfonyl)-C₁₀H₁₆
HOOCCH₂-(D)Phe-Pro-boroOrn(N-Methanesulfonyl)-C₁₀H₁₆·HCl
PhCH₂SO₂-(D)Phe-Pro-boroOrn (N-Methanesulfonyl)-C₁₀H₁₆
Boc-(D)Phe-Pro-boroGly[(CH₂)₃-OCH₂CH₃]-C₁₀H₁₆
Boc-(D)Phe-Pro-boroGly[(CH₂)₃-CN]-C₁₀H₁₆
Boc-(D)Phe-Pro-boroOrn(COCH₃)-C₁₀H₁₆
Ac-(D)Phe-Pro-NH-CH[CH₂(4-amino-cyclohexyl)]BO₂-C₁₀H₁₆
Boc-(D)Phe-Pro-NH-CH[CH₂(4-amino-cyclohexyl)]BO₂-C₁₀H₁₆
Boc-(D)Phe-Pro-NH-CH[4-amino-cyclohexyl]BO₂-C₁₀H₁₆
Boc-(D)Phe-Pro-NH-CH[CH₂(4-hydoxy-cyclohexyl)]BO₂-C₁₀H₁₆
Boc-(D)Phe-Pro-NH-CH[CH₂(4-guanidino-cyclohexyl)]BO₂-C₁₀H₁₆
Boc-(D)Phe-Pro-(R)Phe(mCN)-OMe
Boc-(D)Phe-Pro-(S)Phe(mCN)-OMe
Boc-Pro-(S)Phe(mCN)-OMe
Boc-Pro-Phe(mCN)—OH
Boc-Pro-Phe(mCN)-N(Me)-OMe
Boc-Pro-Phe(mCN)-C(OEt)=CH₂

H-(D)Phe-Pro-boroPhe(mCOOMe)-$C_{10}H_{16}$·HCl

Further illustrative of the compounds of this invention are:

H-(D)Phe-Pro-Phe(mCN)—C(O)H
H-(D)Phe-Pro-Phe(mCN)—C(O)OEt
H-(D)Phe-Pro-Phe(mCN)—C(O)OH
H-(D)Phe-Pro-Phe(mCN)—C(O)NH$_2$
H-(D)Phe-Pro-Phe(mCN)—C(O)NHCH$_3$
H-(D)Phe-Pro-Phe(mCN)—C(O)C(O)OEt
H-(D)Phe-Pro-Phe(mCN)—C(O)—(oxazolin-2-yl)
H-(D)Phe-Pro-Phe(mCN)—C(O)—(benzoxazolin-2-yl)
H-(D)Phe-Pro-Phe(mCN)—C(O)CH$_2$F
H-(D)Phe-Pro-Phe(mCN)—C(O)CH$_2$Br
H-(D)Phe-Pro-Phe(mCN)—C(O)CH$_2$Cl
H-(D)Phe-Pro-Phe(mCN)—C(O)CF$_3$
H-(D)Phe-Pro-Phe(mCN)—C(O)CHF$_2$
Ac-(D)Phe-Pro-Phe(mCN)—C(O)H
Ac-(D)Phe-Pro-Phe(mCN)—C(O)OEt
Ac-(D)Phe-Pro-Phe (mCN)—C(O)OH
Ac-(D)Phe-Pro-Phe (mCN)—C(O)NH$_2$
Ac-(D)Phe-Pro-Phe (mCN)—C(O)NHCH$_3$
Ac-(D)Phe-Pro-Phe (mCN)—C(O)C(O)OEt
Ac-(D)Phe-Pro-Phe (mCN)—C(O)—(oxazolin-2-yl)
Ac-(D)Phe-Pro-Phe (mCN)—C(O)—(benzoxazolin-2-yl)
Ac-(D)Phe-Pro-Phe (mCN)—C(O)CH$_2$F
Ac-(D)Phe-Pro-Phe (mCN)—C(O)CH$_2$Br
Ac-(D)Phe-Pro-Phe (meN)—C(O)CH$_2$Cl
Ac-(D)Phe-Pro-Phe (mCN)—C(O)CF$_3$
Ac-(D)Phe-Pro-Phe (mCN)—C(O)CHF$_2$
Ac-(D)Phe-Pro-NH-CH[CH$_2$(4-amino-cyclohexyl)]—C(O)H
Ac-(D)Phe-Pro-NH-CH[CH$_2$(4-amino-cyclohexyl)]—C(O)OEt
Ac-(D)Phe-Pro-NH-CH[CH$_2$(4-amino-cyclohexyl)]—C(O)OH
Ac-(D)Phe-Pro-NH-CH[CH$_2$(4-amino-cyclohexyl)]—C(O)NH$_2$
Ac-(D)Phe-Pro-NH-CH[CH$_2$(4-amino-cyclohexyl)]—C(O)NHCH$_3$
Ac-(D)Phe-Pro-NH-CH[CH$_2$(4-amino-cyclohexyl)]—C(O)C(O)OEt
Ac-(D)Phe-Pro-NH-CH[CH$_2$(4-amino-cyclohexyl)]—C(O)—(oxazolin-2-yl)
Ac-(D)Phe-Pro-NH-CH[CH$_2$(4-amino-cyclohexyl)]—C(O)—(benzoxazolin-2-yl)
Ac-(D)Phe-Pro-NH-CH[CH$_2$(4-amino-cyclohexyl)]—C(O)CH$_2$F
Ac-(D)Phe-Pro-NH-CH[CH$_2$(4-amino-cyclohexyl)]—C(O)CH$_2$Br
Ac-(D)Phe-Pro-NH-CH[CH$_2$(4-amino-cyclohexyl)]—C(O)CH$_2$Cl
Ac-(D)Phe-Pro-NH-CH[CH$_2$(4-amIno-cyclohexyl)]—C(O)CF$_3$
Ac-(D)Phe-Pro-NH-CH[CH$_2$(4-amino-cyclohexyl)]- C(O)CHF$_2$
Boc-(D)Phe-Pro-NH-CH[(CH$_2$)$_3$—ONH$_2$]—C(O)H
Boc-(D)Phe-Pro-NH-CH[(CH$_2$)$_3$—ONH$_2$]—C(O)OEt
Boc-(D)Phe-Pro-NH-CH[(CH$_2$)$_3$—ONH$_2$]—C(O)OH
Boc-(D)Phe-Pro-NH-CH[(CH$_2$)$_3$—ONH$_2$]—C(O)NH$_2$
Boc-(D)Phe-Pro-NH-CH[(CH$_2$)$_3$—ONH$_2$]—C(O)NHCH$_3$
Boc-(D)Phe-Pro-NH-CH[(CH$_2$)$_3$—ONH$_2$]—C(O)C(O)OEt
Boc-(D)Phe-Pro-NH-CH[(CH$_2$)$_3$—ONH$_2$]—C(O)—(oxazolin-2-yl)
Boc-(D)Phe-Pro-NH-CH[(CH$_2$)$_3$—ONH$_2$]—C(O)—(benzoxazolin-2-yl)
Boc-(D)Phe-Pro-NH-CH[(CH$_2$)$_3$—ONH$_2$]—C(O)CH$_2$F
Boc-(D)Phe-Pro-NH-CH[(CH$_2$)$_3$—ONH$_2$]—C(O)CH$_2$Br
Boc-(D)Phe-Pro-NH-CH[(CH$_2$)$_3$—ONH$_2$]—C(O)CH$_2$Cl
Boc-(D)Phe-Pro-NH-CH[(CH$_2$)$_3$—ONH$_2$]—C(O)CF$_3$
Boc-(D)Phe-Pro-NH-CH[(CH$_2$)$_3$—ONH$_2$]—C$_{(o)}$CHF$_2$
Boc-(D)Phe-Pro-NH-CH[(CH$_2$)$_3$—ONHC(=NH)NH$_2$]—C(O)H
Boc-(D)Phe-Pro-NH-CH[(CH$_2$)$_3$—ONHC(=NH)NH$_2$]—C(O)OEt
Boc-(D)Phe-Pro-NH-CH[(CH$_2$)$_3$—ONHC(=NH)NH$_2$]—C(O)OH
Boc-(D)Phe-Pro-NH-CH[(CH$_2$)$_3$—ONHC(=NH)NH$_2$]—C(O)NH$_2$
Boc-(D)Phe-Pro-NH-CH[(CH$_2$)$_3$—ONHC(=NH)NH$_2$]—C(O)NHCH$_3$
Boc-(D)Phe-Pro-NH-CH[(CH$_2$)$_3$—ONHC(=NH)NH$_2$]—C(O)C(O)OEt
Boc-(D)Phe-Pro-NH-CH[(CH$_2$)$_3$—ONHC(=NH)NH$_2$]—C(O)—(oxazolin-2-yl)
Boc-(D)Phe-Pro-NH-CH[(CH$_2$)$_3$—ONHC(=NH)NH$_2$]—C(O)—(benzoxazolin-2-yl)
Boc-(D)Phe-Pro-NH-CH[(CH$_2$)$_3$—ONHC(=NH)NH$_2$]—C(O)CH$_2$F
Boc-(D)Phe-Pro-NH-CH[(CH$_2$)$_3$—ONHC(=NH)NH$_2$]—C(O)CH$_2$Br
Boc-(D)Phe-Pro-NH-CH[(CH$_2$)$_3$—ONHC(=NH)NH$_2$]—C(O)CH$_2$Cl
Boc-(D)Phe-Pro-NH-CH[(CH$_2$)$_3$—ONHC(=NH)NH$_2$]—C(O)CF$_3$
Boc-(D)Phe-Pro-NH-CH[(CH$_2$)$_3$—ONHC(=NH)NH$_2$]—C(O)CHF$_2$ This invention also provides compositions comprising one or more of the foregoing compounds and methods of using such compositions in the treatment of aberrant proteolysis such as thrombosis in mammals or as reagents used as anticoagulants in the processing of blood to plasma for diagnostic and other commercial purposes.

DETAILED DESCRIPTION OF THE INVENTION

As used throughout the specifications, the following abbreviations for amino acid residues or amino acids apply:
Ala=L-alanine
Arg=L-arginine
Asn=L-asparagine
Asp=L-aspartic acid
Aze=azedine-2-carboxlic acid
Cys=L-cysteine
Gln=L-glutamine
Glu=L-glutamic acid
Gly=glycine
His=L-histidine
HomoLys=L-homolysine
Ile=L-isoleucine
Irg=isothiouronium analog of L-Arg
Leu=L-leucine
Lys=L-lysine
Met=L-methionine
Orn=L-ornithine
Phe=L-phenylalanine
Pro=L-proline
Ser=L-serine
Thr=L-threonine
Trp=L-tryptophan
Tyr=L-tyrosine
Val=L-valine
Sat=L-sarcosine
Phe(4-fluoro)=para-fluorophenylalanine The "D" prefix for the foregoing abbreviations indicates the amino acid is in the D-configuration. "D,L" indicates the amino is present in mixture of the D- and the L-configuration. The prefix "boro" indicates amino acid residues where the carboxyl is replaced by a boronic acid or a boronic acid ester. For example, if $R^1$ is isopropyl and $Y^1$ and $Y^2$ are OH, the C-terminal residue is abbreviated "boroVal—OH" where "—OH" indicates the boronic acid is in the form of the free acid. The pinanediol boronic acid ester and the pinacol boronic acid ester are abbreviated "-$C_{10}H_{16}$" and "-$C_6H_{12}$", respectively. Examples of other useful diols for esterification with the boronic acids are 1,2-ethanediol, 1,3-propanediol, 1,2-propanediol, 2,3-butanediol, 1,2-diisopropylethanediol, 5,6-decanediol, and 1,2-dicyclohexylethanediol. The formamidino modified amino group is abbreviated (CH=NH). For example, the formamidino analog of -boroOrn—OH {—NH—CH [($CH_2$)$_3$—NH—CH(NH)H]B(OH)$_2$}is —boroOrn(CH=NH)—OH. Analogs containing sidechain substituents are described by indicating the substituent in parenthesis following the name of the parent residue. For example the analog of boroPhenylalanine containing a meta cyano group is -boroPhe(mCN)-. N-alkyl substituents on the guanidino group of boroArg- or on the isothiouronium analogs (boroIrg)are also put in parenthesis in a similar manner. Other abbreviations are: Z, benzyloxycarbonyl; BSA, benzene sulfonic acid; THF, tetrahydrofuran; Boc-, t-butoxycarbonyl-; Ac-, acetyl; pNA, p-nitro-aniline; DMAP, 4-N,N-dimethylaminopyridine; Tris, Tris (hydroxymethyl)aminomethane; MS, mass spectrometry; FAB/MS, fast atom bombardment mass spectrometry. LRMS($NH_3$-CI)and HRMS($NH_3$-CI)are low and high resolution mass spectrometry, respectively, using $NH_3$ as an ion source.

The following abbreviations may also be used herein and are defined as follows. The abbreviation "DIBAl" means diisobutylaluminum hydride. The abbreviation "RaNi" means Raney nickel. The abbreviation "LAH" means lithium aluminum hydride. The abbreviation "1,1'-CDI" means 1,1'-carbonyldiimidazole. The abbreviation "Bn" means benzyl. The abbreviation "BOC" means t-butyl carbamate. The abbreviation "CBZ" means benzyl carbamate.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out. A given reaction may be carried out in one solvent or a mixture of more than one solvent. Depending on the particular reaction step, suitable solvents for a particular reaction step may be selected.

When any variable (for example, $R^{11}$, $R^{12}$, $R^{13}$, $R^{14}$, m, etc.) occurs more than one time in any constituent or formula for a compound, its definition on each occurrence is independent of its definition at every other occurrence. Thus, for example, if a group is shown to be substituted with 0–3 $R^{11}$, then said group may optionally be substituted with up to three $R^{11}$ and $R^{11}$ at each occurrence is selected independently from the defined list of possible $R^{11}$. Also, combinations of substituents and/or variables are permissible only if such combinations result in stable compounds. By stable compound or stable structure it is meant herein a compound that is sufficiently robust to survive isolation to a useful degree of purity from a reaction mixture. Similarly, by way of example, for the group -C($R^{11}$)$_2$-, each of the two $R^{11}$ substituents on C is independently selected from the defined list of possible $R^{11}$.

When a bond to a substituent is shown to cross the bond connecting two atoms in a ring, then such substituent may be bonded to any atom on the ring when a substituent is listed without indicating the atom via which such substituent is bonded to the rest of the compound of a given formula, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of a given formula via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

"$NH_2$-blocking group" as used herein, refers to various acyl, thioacyl, alkyl, sulfonyl, phosphoryl, and phosphinyl groups comprised of 1 to 20 carbon atoms. Substitutes on these groups maybe either alkyl, aryl, alkylaryl which may contain the heteroatoms, O, S, and N as a substituent or in-chain component. A number of $NH_2$-blocking groups are recognized by those skilled in the art of organic synthesis. By definition, an $NH_2$-blocking group may be removable or may remain permanently bound to the $NH_2$. Examples of suitable groups include formyl, acetyl, benzoyl, trifluoroacetyl, and methoxysuccinyl; aromatic urethane protecting groups, such as, benzyloxycarbonyl; and aliphatic urethane protecting groups, such as t-butoxycarbonyl or adamantyloxycarbonyl. Gross and Meinhoffer, eds., *The Peptides*, Vol 3; 3–88 (1981), Academic Press, New York, and Greene and Wuts *Protective Groups in Organic Synthesis*, 315–405 (1991), J. Wiley and Sons, Inc., New York disclose numerous suitable amine protecting groups and they are incorporated herein by reference for that purpose. Amine protecting groups may include, but are not limited to the following: 2,7-di-t-butyl-[9-(10,10-dioxo-10,10,10,10-tetrahydrothio-xanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl) ethyloxycarbonyl; benzyloxycarbonyl; p-nitrobenzyloxycarbonyl; 2-(p-toluenesulfonyl) ethyloxycarbonyl; m-chloro-p-acyloxybenzyloxycarbonyl; 5-benzyisoxazolylmethyloxycarbonyl; p-(dihydroxyboryl) benzyloxycarbonyl; m-nitrophenyloxycarbonyl; o-nitrobenzyloxycarbonyl; 3,5- dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; or methanesulfonamide.

"Amino acid residues" as used herein, refers to natural, modified or unnatural amino acids of either D- or L-configuration and means an organic compound containing both a basic amino group and an acidic carboxyl group. Natural amino acids residues are Ala, Arg, Asn, Asp, Aze, Cys, Gln, Glu, Gly, His, Ile, Irg Leu, Lys, Met, Orn, Phe, Phe(4-fluoro), Pro, Sar, Ser, Thr, Trp, Tyr, and Val. Roberts and Vellaccio, The Peptides, Vol 5; 341–449 (1983), Academic Press, New York, discloses numerous suitable unnatural amino acids and is incorporated herein by reference for that purpose. Additionally, said reference describes, but does not extensively list, acylic N-alkyl and acyclic α,α-disubstituted amino acids. Included in the scope of the present invention are N-alkyl, aryl, and alkylaryl analogs of both in chain and N-terminal amino acid residues. Similarly, alkyl, aryl, and alkylaryl maybe substituted for the alpha hydrogen. Illustrated below are examples of N-alkyl and alpha alkyl amino acid residues, respectively.

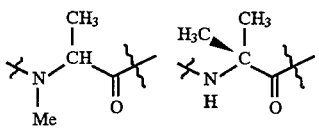

Unnatural amino acids that fall within the scope of this invention are by way of example and without limitation: 2-aminobutanoic acid, 2-aminopentanoic acid, 2-aminohexanoic acid, 2-aminoheptanoic acid, 2-aminooctanoic acid, 2-aminononanoic acid, 2-aminodecanoic acid, 2-aminoundecanoic acid, 2-amino-3,3-dimethylbutanoic acid, 2-amino-4,4-dimethylpentanoic acid, 2-amino-3-methylhexanoic acid, 2-amino-3-methylheptanoic acid, 2-amino-3-methyloctanoic acid, 2-amino-3-methylnonanoic acid, 2-amino-4-methylhexanoic acid, 2-amino-3-ethylpentanoic acid, 2-amino-3,4-dimethylpentanoic acid, 2-amino-3,5-dimethylhexanoic acid, 2-amino-3,3-dimethylpentanoic acid, 2-amino-3-ethyl-3-methylpentanoic acid, 2-amino-3,3-diethylpentanoic acid, 2-amino-5-methylhexanoic acid, 2-amino-6-methylheptanoic, 2-amino-7-methyloctanoic, 2-amino-2-cyclopentylacetic , 2-amino-2-cylcohexylacetic acid, 2-amino-2-(1-methylcylcohexyl)acetic acid, 2-amino-2-(2-methyl-1-methylcylcohexyl)acetic acid, 2-amino-2-(3-methyl-1-methylcylcohexyl)acetic acid, 2-amino-2-(4-methyl-1-methylcylcohexyl)acetic acid, 2-amino-2-(1-ethylcycolhexyl)acetic acid, 2-amino-3-(cyclohexyl) propanoic acid, 2-amino-4-(cyclohexyl)butanoic acid, 2-amino-3-(1-adamanthyl) propanoic acid, 2-amino-3-butenoic acid, 2-amino-3-methyl-3-butenoic acid, 2-amino-4-pentenoic acid, 2-amino-4-hexenoic acid, 2-amino-5-heptenoic acid, 2-amino-4-methyl-4-hexenoic acid, 2-amino-5-methyl-4-hexenoic acid, 2-amino-4-methy-5-hexenoic acid, 2-amino-6-heptenoic acid, 2-amino-3,3,4-trimethyl-4-pentenoic acid, 2-amino-4-chloro-4-pentenoic, 2-amino-4,4-dichloro-3-butenoic acid, 2-amino-3-(2-methylenecyclopropyl)-propanoic acid, 2-amino-2-(2-cyclopentenyl)acetic acid, 2-amino-2-(cyclohexenyl)acetic acid, 2-amino-3-(2-cyclopentenyl)propanoic acid, 2-amino-3-(3-cyclopentenyl)propanoic acid, 2-amino-3-(1-cyclohexyl )propanoic acid, 2-amino-2-(1-cyclopentenyl) acetic acid, 2-amino-2-(1-cylcohexyl)acetic acid, 2-amino-2-(1-cylcoheptenyl)acetic acid, 2-amino-2-(1-cyclooctenyl) acetic acid, 2-amino-3-(1-cycloheptenyl)propanoic acid, 2-amino-3-(1,4-cyclohexadienyl)propanoic acid, 2-amino-3-(2,5-cyclohexadienyl)propanoic acid, 2-amino-2-(7-cycloheptatrienyl)acetic acid, 2-amino-4,5-hexadienoic acid, 2-amino-3-butynoic acid, 2-amino-4-pentyoic acid, 2-amino-4-hexynoic acid, 2-amino-4-hepten-6-ynoic acid, 2-amino-3-fluoropropanoic acid, 2-amino-3,3,3-trifluoropropanoic acid, 2-amino-3-fluorobutanoic acid, 2-amino-3-fluoropentanoic acid, 2-amino-3-fluorohexanoic acid, 2-amino-3,3-difluorobutanoic acid, 2-amino-3,3-difluoro-3-phenylpropanoic acid, 2-amino-3-perfluoroethylpropanoic acid, 2-amino-3-perfluoropropylpropanoic acid, 2-amino-3-fluoro-3-methylbutanoic acid, 2-amino-5,5,5-trifluoropentanoic acid, 2-amino-3-methyl-4,4,4-trifluorobutanoic acid, 2-amino-3-trifluoromethyl-4,4,4-trifluorobutanoic acid, 2-amino-3,3,4, 4,5,5-heptafluoropentanoic acid, 2-amino-3-methyl-5-fluoropentanoic acid, 2-amino-3-methyl-4-fluoropentanoic acid, 2-amino-5,5-difluorohexanoic acid, 2-amino-4-(fluoromethyl)-5-fluoropentanoic acid, 2-amino-4-trifluoromethyl-5,5,5-trifluoropentanoic acid, 2-amino-3-fluoro-3-methylbutanoic acid, 2-amino-3-fluoro-3-phenylpentanoic acid, 2-amino-2-(1-fluorocyclopentyl) acetic acid, 2-amino-2-(1-fluorocyclohexyl)acetic acid, 2-amino-3-chloropropanoic acid acid, 2-amino-3-chlorobutanoic acid acid, 2-amino-4,4-dichlorobutanoic acid acid, 2-amino-4,4,4-trichlorobutanoic acid, 2-amino-3, 4,4-trichlorobutanoic acid, 2-amino-6-chlorohexanoic acid, 2-amino-4-bromobutanoic acid, 2-amino-3-bromobutanoic acid, 2-amino-3-mercaptobutanoic acid, 2-amino-4-mercaptobutanoic acid, 2-amino-3-mercapto-3,3-dimethylpropanoic acid, 2-amino-3-mercapto-3-methylpentanoic acid, 2-amino-3-mercaptopentanoic acid, 2-amino-3-mercapto-4-methylpentanoic acid, 2-amino-3-methyl-4-mercaptopentanoic acid, 2-amino-5-mercapto-5-methylhexanoic acid, 2-amino-2-(1-mercaptocyclobutyl) acetic acid, 2-amino-2-(1-mercaptocyclopentyl)acetic acid, 2-amino-2-(1-mercaptocyclohexyl)acetic acid, 2-amino-5-(methylthio)pentanoic acid, 2-amino-6-(methylthio) hexanoic acid, 2-amino-4-methylthio-3-phenylbutanoic acid, 2-amino-5-ethylthio-5-methylpentanoic acid, 2-amino-5-ethylthio-3,5,5-trimethylpentanoic acid, 2-amino-5-ethylthio-5-phenylpentanoic acid, 2-amino-5-ethylthio-5-pentanoic acid, 2-amino-5-butylthio-5-methylpentanoic acid, 2-amino-5-butylthio-3,5,5-trimethylpentanoic acid, 2-amino-5-butylthio-5-phenylpentanoic acid, 2-amino-5-(butylthio)pentanoic acid, 2-amino-3-methyl-4-hydroselenopentanoic acid, 2-amino-4-methylselenobutanoic acid, 2-amino-4-ethylselenobutanoic acid, 2-amino-4-benzylselenobutanoic acid, 2-amino-3-methyl-4-(methylseleno)butanoic acid, 2-amino-3-(aminomethylseleno)propanoic acid, 2-amino-3-(3-aminopropylseleno)propanoic acid, 2-amino-4-methyltellurobutanoic acid, 2-amino-4-hydroxybutanoic acid, 2-amino-4-hydroxyhexanoic acid, 2-amino-3-hydroxypentanoic acid, 2-amino-3-hydroxyhexanoic acid, 2-amino-3methyl-4-hydroxybutanoic acid, 2-amino-3-hydroxy-3-methylbutanoic acid, 2-amino-6-hydroxyhexanoic acid, 2-amino-4-hydroxyhexanoic acid, 2-amino-3-hydroxy-4-methylpentanoic acid, 2-amino-3-hydroxy-3-5 methylpentanoic acid, 2-amino-4-hydroxy-3,3-dimethylbutanoic acid, 2-amino-3-hyroxy-4-methylpentanoic acid, 2-amino-3-hydroybutanedioic acid, 2-amino-3-hydroxy-3-phenyl-propanoic acid, 2-amino-3- hydroxy-3-(4-nitrophenyl)propanoic acid, 2-amino-3-hydroxy-3-(3-pyridyl)propanoic acid, 2-amino-2-(1-hydroxycyclopropyl)acetic acid, 2-amino-3-(1-hydroxycyclohexyl)propanoic acid, 2-amino-3-hydroxy-3-phenylpropanoic acid, 2-amino-3-hydroxy-3-[3-bis (2-chloroethyl)aminophenyl]propanoic acid, 2-amino-3-hydroxy-3-(3,4-dihydroxyphenyl)propanoic acid, 2-amino-3-hydroxy-3-(3,4-methylenedioxyphenyl)propanoic acid, 2-amino-4-fluoro-3-hydroxybutanoic acid, 2-amino-4,4,4-trichloro-3-hydroxybutanoic acid, 2-amino-3-hydroxy-4-hexynoic acid, 2-amino-3,4-dihydroxybutanoic acid, 2-amino-3,4,5,6-tetrahydroxyhexanoic acid, 2-amino-4,5-dihydroxy-3-methylpentanoic acid, 2-amino-5,6-dihydroxyhexanoic acid, 2-amino-5-hydroxy-4-(hydroxymethyl)pentanoic acid, 2-amino-4,5-dihydroxy-4-(hydroxymethyl)pentanoic acid, 2-amino-3-hydroxy-5-benzyloxypentanoic acid, 2-amino-3-(2-amino, ethoxy)propanoic acid, 2-amino-4-(2-aminoethoxy)butanoic acid, 2-amino-4-oxobutanoic acid, 2-amino-3-oxobutanoic acid, 2-amino-4-methyl-3-oxopentanoic acid, 2-amino-3-phenyl-3-oxopropanoic acid, 2-amino-4-phenyl-3-oxobutanoic acid, 2-amino-3-methyl-4-oxopentanoic acid, 2-amino-4-oxo-4-(4-hydroxyphenyl)butanoic acid, 2-amino-4-oxo-4-(2-furyl)butanoic acid, 2-amino-4-oxo-4-(2-nitrophenyl) butanoic acid, 2-amino-4-oxo-4-(2-amino-4-chlorophenyl) butanoic acid, 2-amino-3-(4-oxo-1-cyclohexenyl)propanoic acid, 2-amino-3-(4-oxocyclohexanyl)propanoic acid, 2-amino-3-(2,5-dimethyl-3,6-dioxo-1,4-cyclohexadienyl) propanoic acid, 2-amino-3-(1-hydroxy-5-methyl-7-oxo-cyclohepta-1,3,5-trien-2-yl) propanoic acid, 2-amino-3-(1-hydroxy-7-oxo-cyclohepta-1,3,5-trien-3-yl) propanoic acid, 2-amino-3-(1-hydroxy-7-oxo-cyclohepta-1,3,5-trien-4-yl) propanoic acid, 2-amino-4-methoxy-3-butenoic acid, 2-amino-4-(2-aminoethoxy)-3-butenoic acid, 2-amino-4-(2-amino-3-hydroxypropyl)-3-butenoic acid, 2-amino-2-(4-methoxy-1,4-cyclohexadienyl)acetic acid, 2-amino-3,3-diethoxypropanoic acid, 2-amino-4,4-dimethylbutanoic acid, 2-amino-2-(2,3-epoxycyclohexyl)acetic acid, 2-amino-3-(2,3-epoxycyclohexy)propanoic acid, 2-amino-8-oxo-9,10-epoxydecanoic acid, 2-amino-propanedioic acid, 2-amino-3-methylbutanedioic acid, 2-amino-3,3-dimethylbutanedioic acid, 2-amino-4-methylpentanedioic acid, 2-amino-3-methylpentanedioic acid, 2-amino-3-phenylpentanedioic acid, 2-amino-3-hydroxypentanedioic acid, 2-amino-3-carboxypentanedioic acid, 2-amino-4-ethylpentanedioic acid, 2-amino-4-propylpentanedioic acid, 2-amino-4-isoamylpentanedioic acid, 2-amino-4-phenylpentanedioic acid, 2-amino-hexanedioic acid, 2-amino-heptanedioic acid, 2-amino-decanedioic acid, 2-amino-octanedioic acid, 2-amino-dodecanedioic acid, 2-amino-3-methylenebutanedioic acid, 2-amino-4-methylenepentanedioic acid, 2-amino-3-fluorobutanedioic acid, 2-amino-4-fluoropentanedioic acid, 2-amino-3,3-difluorobutanedioic acid, 2-amino-3-chloropentanedioic acid, 2-amino-3-hydroxybutanedioic acid, 2-amino-4-hydroxypentanedioic acid, 2-amino-4-hydroxyhexanedioic acid, 2-amino-3,4-dihydroxypentanedioic acid, 2-amino-3-(3-hydroxypropyl)butanedioic acid, 2-amino-3-(1-carboxy-4-hydroxy-2-cyclodienyl)propanoic acid, 2-amino-3-(aceto) butanedioic acid, 2-amino-3-cyanobutanedioic acid, 2-amino-3-(2-carboxy-6-oxo-6H-pyranyl)propanoic acid, 2-amino-3-carboxybutanedioic acid, 2-amino-4-carboxypentanedioic acid, 3-amido-2-amino-3-hydroxypropanoic acid, 3-amido-2-amino-3-methylpropanoic acid, 3-amido-2-amino-3-phenylpropanoic acid, 3-amido-2,3-diaminopropanoic acid, 3-amido-2-amino-3-[N-(4-hydroxyphenyl)amino]propanoic acid, 2,3-diaminopropanoic acid, 2,3-diaminobutanoic acid, 2,4-diaminobutanoic acid, 2,4-diamino-3-methylbutanoic acid, 2,4-diamino-3-phenylbutanoic acid, 2-amino-3-(methylamino)butanoic acid, 2,5-diamino-3-methylpentanoic acid, 2,7-diaminoheptanoic acid, 2,4-diaminoheptanoic acid, 2-amino-2-(2-piperidyl)acetic acid, 2-amino-2-(1-aminocyclohexyl)acetic acid, 2,3-diamino-3-phenylpropanoic acid, 2,3-diamino-3-(4-hydroxyphenyl) propanoic acid, 2,3-diamino-3-(4-methoxyphenyl) propanoic acid, 2,3-diamino-3-[4-(N,N'-dimethyamino) phenyl]propanoic acid, 2,3-diamino-3-(3,4-dimethoxyphenyl)propanoic acid, 2,3-diamino-3-(3,4-methylenedioxyphenyl)propanoic acid, 2,3-diamino-3-(4-hydroxy-3-methoxyphenyl)propanoic acid, 2,3-diamino-3-(2-phenylethyl)propanoic acid, 2,3-diamino-3-propylpropanoic acid, 2,6-diamino-4-hexenoic acid, 2,5-diamino-4-fluoropentanoic acid, 2,6-diamino-5-fluorohexanoic acid, 2,6-diamino-4-hexynoic acid, 2,6-diamino-5,5-difluorohexanoic acid, 2,6-diamino-5,5-dimethylhexanoic acid, 2,5-diamino-3-hydroxypentanoic acid, 2,6-diamino-3-hydroxyhexanoic acid, 2,5-diamino-4-hydroxypentanoic acid, 2,6-diamino-4-hydroxyhexanoic acid, 2,6-diamino-4-oxohexanoic acid, 2,7-diaminooctanedioic acid, 2,6-diamino-3-carboxyhexanoic acid, 2,5-diamino-4-carboxypentanoic acid, 2-amino-4-[2-(N,N'-diethylamino)ethyl]pentandioic acid, 2-amino-4-(N,N'-diethylamino)pentandioic acid, 2-amino-4-(N-morpholino)pentandioic acid, 2-amino-4-[N,N'-bis (2-chloroethyl)amino]pentandioic acid, 2-amino-4-[N,N'-bis(2-hydroxyethyl)amino]pentandioic acid, 2,3,5-triaminopentanoic acid, 2-amino-3-[N-(2-aminethyl)amino] propanoic acid, 2-amino-3-[(2-aminoethyl)seleno] propanoic acid, 2-amino-3-[(2-aminoethyl)thio]propanoic acid, 2-amino-4-aminooxybutanoic acid, 2-amino-5-hydroxyaminopentanoic acid, 2-amino-5-[N-(5-nitro-2-pyrimidinyl)amino]pentanoic acid, 2-amino-4-[(7-nitro-2,1,3-benzoxadiazol-4-yl)amino]butanoic acid, 2-amino-3-guanidinopropanoic acid, 2-amino-3-guanidinobutanoic acid, 2-amino-4-guanidobutanoic acid, 2-amino-6-guanidohexanoic acid, 2-amino-6-ureidohexanoic acid, 2-amino-3-(2-iminoimidazolin-4-yl)propanoic acid, 2-amino-2-(2-iminohexahydropyrimidin-4-yl)acetic acid, 2-amino-3-(2-iminohexahydropyrimidiny-4-yl)propanoic acid, 2-amino-4-fluoro-5-guanidopentanoic acid, 2-amino-4-hydroxy-5-guanidopentanoic acid, 2-amino-4-guanidooxybutanoic acid, 2-amino-6-amidinohexanoic acid, 2-amino-5-(N-acetimidoylamino)pentanoic acid, 1-aminocyclopropanecarboxylic acid, 1-amino-2-ethylcyclpropanecarboxylic acid, 1-aminocyclopentanecarboxylic acid, 1-aminocyclopentanecarboxylic acid, 1-amino-2,2,5,5-tetramethyl-cyclohexanecarboxylic acid, 1-aminocycloheptanecarboxylic acid, 1-aminocyclononanecarboxylic acid, 2-aminoindan-2-carboxylic acid, 2-aminonorbornane-2-carboxylic acid, 2-amino-3-phenylnorbornane-2-carboxylic acid, 3-aminotetrahydrothiophene-3-carboxylic acid, 1-amino-1,3-cyclohexanedicarboxylic acid, 3-aminopyrrolidine-3-carboxylic acid, 1,4-diaminocyclohexanecarboxylic acid, 6-alkoxy-3-amino-1,2,3,4-tetrahydrocarbazole-3-carboxylic acid, 2-aminobenzobicyclo[2,2,2]octane-2-carboxylic acid, 2-aminoindan-2-carboxylic acid, 1-amino-2-(3,4-dhydroxyphenyl)cyclopropanecarboxylic acid, 5,6-dialkoxy-2-aminoindane-2-carboxylic acid, 4,5-dihydroxy-2-aminoindan-2-caroxylic acid, 5,6-dihydroxy-2-aminotetralin-2-carboxylic acid, 2-amino-2-cyanoacetic acid, 2-amino-3-cyanopropanoic acid, 2-amino-4- cyanobutanoic acid, 2-amino-5-nitropentanoic acid, 2-amino-6-nitrohexanoic acid, 2-amino-4-aminooxybutanoic acid, 2-amino-3-(N-nitrosohydroxyamino)propanoic acid, 2-amino-3-ureidopropanoic acid, 2-amino-4-ureidobutanoic acid, 2-amino-3-phosphopropanoic acid, 2-amino-3-thiophosphopropanoic acid, 2-amino-4-methanephosphonylbutanoic acid, 2-amino-3-(trimethylsilyl)propanoic acid, 2-amino-3-(dimethyl (trimethylsilylmethylsilyl)propanoic acid, 2-amino-2-phenylacetic acid, 2-amino-2-(3-chlorophenyl)acetic acid, 2-amino-2-(4-chlorophenyl)acetic acid, 2-amino-2-(3-fluorophenyl)acetic acid, 2-amino-2-(3-methylphenyl)acetic acid, 2-amino-2-(4-fluorophenyl)acetic acid, 2-amino-2-(4-methylphenyl)acetic acid, 2-amino-2-(4-methoxyphenyl) acetic acid, 2-amino-2-(2-fluorophenyl)acetic acid, 2-amino-2-(2-methylphenyl)acetic acid, 2-amino-2-(4-chloromethylphenyl)acetic acid, 2-amino-2-(4-hydroxymethylphenyl)acetic acid, 2-amino-2-[4-(methylthiomethyl)phenyl]acetic acid, 2-amino-2-(4-bromomethylphenyl)acetic acid, 2-amino-2-[4-(methoxymethy)phenyl]acetic acid, 2-amino-2-[4-((N-benzylamino)methyl)phenyl]acetic acid, 2-amino-2-(4-hydroxylphenyl)acetic acid, 2-amino-2-(3-hydroxylphenyl) acetic acid, 2-amino-2-(3-carboxyphenyl)acetic acid, 2-amino-2-(4-aminophenyl)acetic acid, 2-amino-2-(4-azidophenyl)acetic acid, 2-amino-2-(3-t-butyl-4-hydroxyphenyl)acetic acid, 2-amino-2-(3,5-difluoro-4-hydroxyphenyl)acetic acid, 2-amino-2-(3,5-dihydroxyphenyl)acetic acid, 2-amino-2-(3-carboxy-4-hydroxyphenyl)acetic acid, 2-amino-2-(3-di-t-butyl-4-hydroxyphenyl)acetic acid, 2-amino-3-(2-methylphenyl) propanoic acid, 2-amino-3-(4-ethylphenyl)propanoic acid, 2-amino-3-(4-phenylphenyl)propanoic acid, 2-amino-3-(4-benzylphenyl)propanoic acid, 2-amino-3-(3-fluorophenyl) propanoic acid, 2-amino-3-(4-methylphenyl)propanoic acid, 2-amino-3-(4-fluorophenyl)propanoic acid, 2-amino-3-(4-chlorophenyl)propanoic acid, 2-amino-3-(2-chlorophenyl) propanoic acid, 2-amino-3-(4-bromophenyl)propanoic acid, 2-amino-3-(2-bromophenyl)propanoic acid, 2-amino-3-(3-hydroxyphenyl)propanoic acid, 2-amino-3-(2-hydroxyphenyl)propanoic acid, 2-amino-3-(4-mercaptophenyl)propanoic acid, 2-amino-3-(3-trifluoromethylphenyl)propanoic acid, 2-amino-3-(3-hydroxyphenyl)propanoic acid, 2-amino-3-(4-hydroxyphenyl)propanoic acid, 2-amino-3-[4-(hydroxymethy)phenyl]propanoic acid, 2-amino-3-[3-(hydroxymethyl)phenyl]propanoic acid, 2-amino-3-[3-(amlnomethyl)phenyl]propanoic acid, 2-amino-3-(3-carboxyphenyl)propanoic acid, 2-amino-3-(4-nitrophenyl) propanoic acid, 2-amino-3-(4-aminophenyl )propanoic acid, 2-amino-3-(4-azidophenyl)propanoic acid, 2-amino-3-(4-cyanophenyl)propanoic acid, 2-amino-3-(4-acetophenyl) propanoic acid, 2-amino-3-(4-guanidinophenyl)propanoic acid, 2-amino-3-[4-(phenylazo)phenyl]propanoic acid, 2-amino-3-[4-(2-phenylethylenyl)phenyl]propanoic acid, 2-amino-3-(4-trialkylsilylphenyl)propanoic acid, 2-amino-3-(2,4-dimethylphenyl)propanoic acid, 2-amino-3-(2,3-dimethylphenyl)propanoic acid, 2-amino-3-(2,5-dimethylphenyl)propanoic acid, 2-amino-3-(3,5-dimethylphenyl)propanoic acid, 2-amino-3-(2,4,6-trimethylphenyl)propanoic acid, 2-amino-3-(3,4,5-trimethylphenyl)propanoic acid, 2-amino-3-(2,3,4,5,6-pentamethylphenyl)propanoic acid, 2-amino-3-(2,4,-difluorophenyl)propanoic acid, 2-amino-3-(3,4,-difluorophenyl)propanoic acid, 2-amino-3-(2,5,-difluorophenyl)propanoic acid, 2-amino-3-(2,6,-difluorophenyl)propanoic acid, 2-amino-3-(2,3,5,6-tetrafluorophenyl)propanoic acid, 2-amino-3-(3,5-dichloro-2,4,6-trifluorophenyl)propanoic acid, 2-amino-3-(2,3-difluorophenyl)propanoic acid, 2-amino-3-(2,3-bistrifluoromethylphenyl)propanoic acid, 2-amino-3-(2,4-bistrifluoromethylphenyl)propanoic acid, 2-amino-3-(2-chloro-5-trifluoromethylphenyl)propanoic acid, 2-amino-3-(2,5-difluorophenyl)propanoic acid, 2-amino-3-(2,3,4,5,6-pentafluorophenyl)propanoic acid, 2-amino-3-(2,3-dibromophenyl)propanoic acid, 2-amino-3-(2,5-dibromophenyl)propanoic acid, 2-amino-3-(3,4-dibromophenyl)propanoic acid, 2-amino-3-(3,4,5-triiodophenyl)propanoic acid, 2-amino-3-(2,3-dihydroxyphenyl)propanoic acid, 2-amino-3-(2,5-dihydroxyphenyl)propanoic acid, 2-amino-3-(2,6-dihydroxyphenyl)propanoic acid, 2-amino-3-(3-bromo-5-methoxyphenyl)propanoic acid, 2-amino-3-(2,5-dimethoxyphenyl)propanoic acid, 2-amino-3-(2,5-dimethoxy-4-methylphenyl)propanoic acid, 2-amino-3-(4-bromo-2,5-dimethoxyphenyl)propanoic acid, 2-amino-3-(3-carboxy-4-hydroxyphenyl)propanoic acid, 2-amino-3-(3-carboxy-4-aminophenyl)propanoic acid, 2-amino-3-(2-hydroxy-5-nitrophenyl)propanoic acid, 2-amino-3-(2-ethoxy-5-nitrophenyl)propanoic acid, 2-amino-3-(3,4,5-trimethoxyphenyl)propanoic acid, 2-amino-3-(4-azido-2-nitrophenyl)propanoic acid, 2-amino-3-(2-hydroxy-5-nitrophenyl)propanoic acid, 2-amino-3-(2,4-bis-trimethylsilylphenyl)propanoic acid, 2-amino-3-(4-hydroxy-3,5-di-t-butylphenyl)propanoic acid, 2-amino-3-(4-hydroxy-3-benzylphenyl)propanoic acid, 2-amino-3-(4-hydroxy-3-fluorophenyl)propanoic acid, 2-amino-3-(4-hydroxy-2,3,5,6-tetrafluorophenyl)propanoic acid, 2-amino-3-(4-hydroxy-3,5-dichlorophenyl propanoic acid, 2-amino-3-(4-hydroxy-3-iodophenyl)propanoic acid, 2-amino-3-(4-hydroxy-3,5-diiodophenyl)propanoic acid, 2-amino-3-(4-hydroxy-2-hydroxyphenyl)propanoic acid, 2-amino-3-(4-hydroxy-3-hydroxymethylphenyl)propanoic acid, 2-amino-3-5(4-hydroxy-2-hydroxy-6-methylphenyl)propanoic acid, 2-amino-3-(4-hydroxy-3-carboxyphenyl)propanoic acid, 2-amino-3-(4-hydroxy-3,5-dinitrophenyl)propanoic acid, substituted thyronines, 2-amino-3-(3,4-dihydroxy-2-chlorophenyl)propanoic acid, 2-amino-3-(3,4-dihydroxy-2-bromophenyl)propanoic acid, 2-amino-3-(3,4-dihydroxy-2-fluorophenyl)propanoic acid, 2-amino-3-(3,4-dihydroxy-2-nitrophenyl)propanoic acid, 2-amino-3-(3,4-dihydroxy-2-methylphenyl)propanoic acid, 2-amino-3-(3,4-dihydroxy-2-ethylphenyl)propanoic acid, 2-amino-3-(3,4-dihydroxy-2-isopropylphenyl)propanoic acid, 2-amino-3-(2-t-butyl-4,5-dihydroxyphenyl)propanoic acid, 2-amino-3-(3-fluoro-4,5-dihydroxyphenyl)propanoic acid, 2-amino-3-(2-fluoro-4,5-dihydroxyphenyl)propanoic acid, 2-amino-3-(2,5,6-trifluoro-3,4-dihydroxyphenyl)propanoic acid, 2-amino-3-(2,6-dibromo-3,4-dihydroxyphenyl)propanoic acid, 2-amino-3-(5,6-dibromo-3,4-dihydroxyphenyl)propanoic acid, 2-amino-3-(2,4,5-trihydroxyphenyl)propanoic acid, 2-amino-3-(2,3,4-trihydroxyphenyl)propanoic acid, 2-amino-3-(3,4-dihydroxy-5-methoxyphenyl)propanoic acid, 2-amino-3-methyl-3-phenylpropanoic acid, 2-amino-3-ethyl-3-phenylpropanoic acid, 2-amino-isopropyl-3-phenylpropanoic acid, 2-amino-3-butyl-3-phenylpropanoic acid, 2-amino-3-benzyl-3-phenylpropanoic acid, 2-amino-3-phenylethyl-3-phenylpropanoic acid, 2-amino-3-(4-chlorophenyl)-3-phenylpropanoic acid, 2-amino-3-(4-methoxyphenyl)-3-phenylpropanoic acid, 2-amino-3,3-diphenylpropanoic acid, 2-amino-3-[4-(N,N-diethylamino) phenyl]heptanoic acid, 2-amino-3-[4-(N,N-diethylamino) phenyl]pentanoic acid, 2-amino-3-(3,4-dimethoxyphenyl)

pentanoic acid, 2-amino-3-(3,4-dihydroxyphenyl)pentanoic acid, 2-amino-3-methyl-3-phenylbutanoic acid, 2-amino-3-ethyl-3-phenylpentanoic acid, 2-amino-3-methyl-3-phenylpentanoic acid, 2-amino-3,3-diphenylbutanoic acid, 2-amino-3-fluoro-3-phenylpropanoic acid, 2-amino-3-methylene-3-5 phenylpropanoic acid, 2-amino-3-methylmercapto-3-phenylpropanoic acid, 2-amino-4-methylmercapto-4-phenylbutanoic acid, 2-amino-4-(3,4-dihydroxyphenyl)butanoic acid, 2-amino-5-(4-methoxyphenyl)pentanoic acid, 2-amino-4-phenylbutanoic acid, 2-amino-5-phenylpentanoic acid, 2-amino-3,3-dimethyl-5-phenylpentanoic acid, 2-amino-4-phenyl-3-butenoic acid, 2-amino-4-phenoxybutanoic acid, 2-amino-5-phenoxypentanoic acid, 2-amino-2-(indanyl)acetic acid, 2-amino-2-(1-tetralyl)acetic acid, 2-amino-4,4-diphenylbutanoic acid, 2-amino-2-(2-naphthyl)acetic acid, 2-amino-3-(1-naphthyl)propanoic acid, 2-amino-3-(1-naphthyl) pentanoic acid, 2-amino-3-(2-naphthyl)propanoic acid, 2-amino-3-(1-chloro-2-naphthyl)propanoic acid, 2-amino-3-(1-bromo-2-naphthyl)propanoic acid, 2-amino-3-(4-hydroxy-1-naphthyl)propanoic acid, 2-amino-3-(4-methoxy-1-naphthyl)propanoic acid, 2-amino-3-(4-hydroxy-2-chloro-1-naphthyl)propanoic acid, 2-amino-3-(2-chloro-4-methoxy-1-naphthyl)propanoic acid, 2-amino-2-(2-anthryl)acetic acid, 2-amino-3-(9-anthryl)propanoic acid, 2-amino-3-(2-fluorenyl)propanoic acid, 2-amino-3-(4-fluorenyl)propanoic acid, 2-amino-3-(carboranyl)propanoic acid, 3-methylproline, 4-methylproline, 5-methylproline, 4,4-dimethylproline, 4-fluoroproline, 4,4-difluoroproline, 4-bromoproline, 4-chloroproline, 4-aminoproline, 3,4-dehydroproline, 4-methylproline, 4-methyleneproline, 4-mercaptoproline, 4-(4-methoxybenzylmercapto)proline, 4-hydroxymethylproline, 3-hydroxyproline, 3-hydroxy-5-methylproline, 3,4-dihydroxyproline, 3-phenoxyproline, 2-aminoproline, 5-aminoproline, 3-carbamylalkylproline, 4-cyano-5-methyl-5-carboxyproline, 4,5-dicarboxyl-5-methylproline, 2-aziridinecarboxylic acid, 2-azetidinecarboxylic acid, 4-methyl-2-azetidinecarboxylic acid, pipecolic acid, 1,2,3,6-tetrahydropicolinic acid, 3,4-methyleneproline, 2,4-methyleneproline, 4-aminopipecolic acid, 5-hydroxypipecolic acid, 4,5-dihydroxypipecolic acid, 5,6-dihydroxy-2,3-dihydroindole-2-carboxylic acid, 1,2,3,4-tetrahydroquinoline-2-carboxylic acid, 6,7-dihydroxy-1,2,3,4-tetrahydroisoquinoline-3-carboxylic acid, 6-hydroxy-1-methyl-1,2,3,4-tetrahydroisoquinoline-3-carboxylic acid, 6,7-dihydroxy-1-methyl-1,2,3,4-tetrahydroisoquinoline-3-carboxylic acid, 1,3-oxazolidine-4-carboxylic acid, 1,2-oxazolidine-3-carboxylic acid, perhydro-1,4-thiazine-3-carboxylic acid, 2,2-dimethylthiazolidine-4-carboxylic acid, perhydro-1,3-thiazine-2-carboxylic acid, selenazolidine-4-carboxylic acid, 2-phenylthiazolidine-4-carboxylic acid, 2-(4-methylphenyl)thiazolidine-4-carboxylic acid, 1,2,3,4,4a,9a-hexahydro-beta-carboline-3-carboxylic acid, 2,3,3a,8a-tetrahydropyrrolo(2,3b) indole-2-carboxylic acid, 2-amino-3-(2-pyridyl)propanoic acid, 2-amino-3-(3-pyridyl)propanoic acid, 2-amino-3-(4-pyridyl)propanoic acid, 2-amino-3-(2-bromo-3-pyridyl)propanoic acid, 2-amino-3-(2-bromo-4-pyridyl)propanoic acid, 2-amino-3-(2-bromo-5-pyridyl)propanoic acid, 2-amino-3-(2-bromo-6-pyridyl)propanoic acid, 2-amino-3-(2-chloro-3-pyridyl)propanoic acid, 2-amino-3-(2-chloro-4-pyridyl)propanoic acid, 2-amino-3-(2-chloro-5-pyridyl)propanoic acid, 2-amino-3-(2-chloro-6-pyridyl)propanoic acid, 2-amino-3-(2-fluoro-3-pyridyl)propanoic acid, 2-amino-3-(2-fluoro-4-pyridyl)propanoic acid, 2-amino-3-(2-fluoro-5-pyridyl)propanoic acid, 2-amino-3-(2-fluoro-6-pyridyl)propanoic acid, 2-amino-3-(1,2-dihydro-2-oxo-3-pyridyl)propanoic acid, 2-amino-3-(1,2-dihydro-2-oxo-4-pyridyl)propanoic acid, 2-amino-3-(1,2-dihydro-2-oxo-5-pyridyl)propanoic acid, 2-amino-3-(1,2-dihydro-2-oxo-6-pyridyl)propanoic acid, 2-amino-3-(5-hydroxy-2-5 pyridyl)propanoic acid, 2-amino-3-(5-hydroxy-6-iodo-2-pyridyl)propanoic acid, 2-amino-3-(3-hydroxy-4-oxo-1,4dihydro-1-pyridyl) propanoic acid, N-(5-caroxyl-5-aminopentyl)pyridinium chloride, 1,2,5-trimethyl-4-(2-amino-2-carboxy-1-hydroxyethyl)pyridinium chloride, 2-amino-2-(5-chloro-2-pyridyl)acetic acid, N-(3-amino-3-carboxypropyl) pyridinium chloride, 2-amino-3-(2-pyrryl)propanoic acid, 2-amino-3-(1-pyrryl)propanoic acid, 2-amino-4-(1-pyrryl) butanoic acid, 2-amino-5-(1-pyrryl)pentanoic acid, 2-amino-3-(5-imidazolyl)-3-methylpropanoic acid, 2-amino-3-(5-imidazolyl)-3-ethylpropanoic acid, 2-amino-3-hexyl-3-(5-imidazolyl)propanoic acid, 2-amino-3-hydroxy-3-(5-imidazolyl)propanoic acid, 2-amino-3-(4-nitro-5-imidazolyl)propanoic acid, 2-amino-3-(4-methyl-5-imidazolyl)propanoic acid, 2-amino-3-(2-methyl-5-imidazolyl)propanoic acid, 2-amino-3-(4-fluoro-5-imidazolyl)propanoic acid, 2-amino-3-(2-fluoro-5-imidazolyl)propanoic acid, 2-amino-3-(2-amino-5-imidazolyl)propanoic acid, 2-amino-3-(2-phenylaza-5-imidazolyl)propanoic acid, 2-amino-3-(1-methyl-2-nitro-5-imidazolyl)propanoic acid, 2-amino-3-(1-methyl-4-nitro-5-imidazolyl)propanoic acid, 2-amino-3-(1-methyl-5-nitro-5-imidazolyl)propanoic acid, 2-amino-3-(2-mercapto-5-imidazolyl)propanoic acid, 2-amino-4-(5-imidazolyl) butanoic acid, 2-amino-3-(1-imidazolyl)propanoic acid, 2-amino-3-(2-imidazolyl)propanoic acid, 2-amino-(1-pyrazolyl)propanoic acid, 2-amino-(3-pyrazolyl)propanoic acid, 2-amino-(3, 5-dialkyl-4-pyrazolyl)propanoic acid, 2-amino-3-(3-amino-1,2, 4-triazol-1-yl)propanoic acid, amino-3-(tetrazol-5-yl)propanoic acid, 2-amino-4-(5-tetrazolyl)butanoic acid, 2-amino-3-(6-methyl-3-indolyl) propanoic acid, 2-amino-3-(4-fluoro-3-indolyl)propanoic acid, 2-amino-3-(5-fluoro-3-indolyl)propanoic acid, 2-amino-3-(6-fluoro-3-indolyl)propanoic acid, 2-amino-3-(4,5,6,7-tetrafluoro-3-indolyl)propanoic acid, 2-amino-3-(5-chloro-3-indolyl)propanoic acid, 2-amino-3-(6-chloro-3-indolyl)propanoic acid, 2-amino-3-(7-chloro-3-indolyl) propanoic acid, 2-amino-3-(5-bromo-3-indolyl)propanoic acid, 2-amino-3-(7-bromo-3-indolyl)propanoic acid, 2-amino-3-(2-hydroxy-3-indolyl)propanoic acid, 2-amino-3-(5-hydroxy-3-indolyl)propanoic acid, 2-amino-3-(7-hydroxy-3-indolyl)propanoic acid, 2-amino-3-(2-alkylmercapto-3-indolyl)propanoic acid, 2-amino-3-(7-amino-3-indolyl)propanoic acid, 2-amino-3-(4-nitro-3-indolyl)propanoic acid, 2-amino-3-(7-nitro-3-indolyl) propanoic acid, 2-amino-3-(4-carboxy-3-indolyl)propanoic acid, 2-amino-3-(3-indolyl)butanoic acid, 2-amino-3-(2,3-dihydro-3-indolyl)propanoic acid, 2-amino-3-(2,3-dihydro-2-oxo-3-indolyl)propanoic acid, 2-amino-3-alkylmercapto-3-(3-indolyl)propanoic acid, 2-amino-3-(4-aza-3-indolyl) propanoic acid, 2-amino-3-(7-aza-3-indolyl)propanoic acid, 2-amino-3-(7-aza-6-chloro-4-methyl-3-indolyl)propanoic acid, 2-amino-3-(2,3-dihydrobenzofuran-3-yl)propanoic acid, 2-amino-3-(3-methyl-5-7-dialkylbenzofuran-2-yl) propanoic acid, 2-amino-3-(benzothiophen-3-yl)propanoic acid, 2-amino-3-(5-hydroxybenzothiophen-3-yl)propanoic acid, 2-amino-3-(benzoselenol-3yl)propanoic acid, 2-amino-3-quinolylpropanoic acid, 2-amino-3-(8-hydroxy-5-quinolyl)propanoic acid, 2-amino-2-(5,6,7,8-tetrahydroquinol-5-yl)acetic acid, 2-amino-3-(3-coumarinyl)propanoic acid, 2-amino-2-(benzisoxazol-3-yl) acetic acid, 2-amino-2-(5-methylbenzisoxazol-3-yl)acetic acid, 2-amino-2-(6-methylbenzisoxazol-3-yl)acetic acid, 2-amino-2-(7-methylbenzisoxazol-3-yl)acetic acid, 2-amino-2-(5-bromobenzisoxazol-3-yl)acetic acid, 2-amino-3-(benzimidazol-2-yl)propanoic acid, 2-amino-3-(5, 6-dichlorobenzimidazol-2-yl)propanoic acid, 2-amino-3-(5, 6-dimethylbenzimidazol-2-yl)propanoic acid, 2-amino-3-(4,5, 6, 7-hydrobenzimidazol-2-yl)propanoic acid, 2-amino-2-(benzimidazol-5-yl)acetic acid, 2-amino-2-(1, 3-dihydro-2,2-dioxoisobenzothiophen-5-yl) acetic acid, 2-amino-2-(1,3-dihydro-2,2-dioxo-2,1,3-benzothiadiazol-5-yl)acetic acid, 2-amino-2-(2-oxobenzimidazol-5-yl)acetic acid, 2-amino-3-(4-hydroxybenzothiazol-6-yl)propanoic acid, 2-amino-3-(benzoxazol-2-yl)propanoic acid, 2-amino-3-(benzothiazol-2-yl)propanoic acid, 2-amino-3-(9-adeninyl)propanoic acid, 2-amino-2-(6-chloro-9-purinyl)acetic acid, 2-amino-2-(6-amino-9-purinyl)acetic acid, 2-amino-3-(6-purinyl)propanoic acid, 2-amino-3-(8-theobrominyl)propanoic acid, 2-amino-2-(1-uracilyl)acetic acid, 2-amino-2-(1-cytosinyl)acetic acid, 2-amino-3-(1-uracilyl)propanoic acid, 2-amino-3-(1-cytosinyl)propanoic acid, 2-amino-4-(1-pyrimidinyl)butanoic acid, 2-amino-4-(4-amino-1-pyrimidinyl)butanoic acid, 2-amino-4-(4-hydroxy-1-pyrimidinyl)butanoic acid, 2-amino-5-(1-pyrimidinyl)pentanoic acid, 2-amino-5-(4-amino-1-pyrimidinyl)pentanoic acid, 2-amino-5-(4-hydroxy-1-pyrimidinyl)pentanoic acid, 2-amino-3-(5-pyrimidinyl) propanoic acid, 2-amino-3-(6-uracilyl)propanoic acid, 2-amino-3-(2-pyrimidinyl)propanoic acid, 2-amino-3-(6-amino-4-chloro-2-pyrimidinyl)propanoic acid, 2-amino-3-(4-hydroxy-2-pyrimidinyl)propanoic acid, 2-amino-3-(2-amino-4-pyrimidinyl)propanoic acid, 2-amino-3-(4,5-dihydroxypyrimidin-2-yl)propanoic acid, 2-amino-3-(2-thiouracil-6-yl)propanoic acid, 2-amino-2-(5-alkyl-2-tetrahydrofuryl)acetic acid, 2-amino-2-(5-methyl-2,5-dihydro-2-furyl)acetic acid, 2-amino-2-(5-alkyl-2-furyl) acetic acid, 2-amino-2-(2-furyl)acetic acid, 2-amino-2-(3-hydroxy-5-methyl-4-isoxazolyl)acetic acid, 2-amino-2-(4-bromo-3-hydroxy-5-isoxazolyl)propanoic acid, 2-amino-3-(4-methyl-3-hydroxy-5-isoxazolyl)propanoic acid, 2-amino-3-(3-hydroxy-5-isoxazolyl)propanoic acid, 2-amino-2-(3-chloro-D$^2$-isoxazolin-5-yl)acetic acid, 2-amino-2-(3-oxo-5-isoxazolidinyl)acetic acid, 2-amino-3-(3,5-dioxo-1,2,4-oxadiazolin-2-yl)propanoic acid, 2-amino-3-(3-phenyl-5-isoxazolyl)propanoic acid, 2-amino-3-[3-(4-hydroxyphenyl)-1,2,4-oxadiazol-5-yl]propanoic acid, 2-amino-3-(2-thienyl)propanoic acid, 2-amino-2-(2-furyl) acetic acid, 2-amino-2-(2-thienyl)acetic acid, 2-amino-2-(2-thiazolyl)acetic acid, 2-amino-3-(2-thiazolyl)propanoic acid, 2-amino-4-(4-carboxy-2-thiazolyl)butanoic acid, 2-amino-3-(4-thiazolyl)propanoic acid, 2-amino-3-(2-selenolyl)propanoic acid, 2-amino-3-(2-amino-4-selenolyl) propanoic acid, 2-amino-3-(β-ribofuranosyl)propanoic acid, "Amino acids residues" also refers to various amino acids where sidechain functional groups are coupled with appropriate protecting groups known to those skilled in the art. "The Peptides", Vol 3, 3–88 (1981)discloses numerous suitable protecting groups and is incorporated herein by reference for that purpose.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example -C$_v$F$_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl, adamantyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like.

The terms "-(alkyl)-", "-(alkyenyl)-", "-(phenyl)-", and the like, refer to alkyl, alkenyl, and phenyl groups, respectively, which are connected by two bonds to the rest of the structure of Formula (II). Such groups may alternatively and equivalently be denoted as "alkylene", "alkenylene", "phenylene", and the like, respectively.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "C$_7$–C$_{10}$ arylalkyl" is intended to refer to an aryl group attached through a C$_1$–C$_4$ alkyl bridge to the residue of the indicated compound; the term "(C$_1$–C$_3$ alkyl) aryl" is intended to refer to a C$_1$–C$_3$ alkyl group which is attached through an aryl ring to the residue of the indicated compound; the term "aryl(C$_1$–C$_3$ alkyl)" is intended to refer to an aryl group attached through a C$_1$–C$_3$ alkyl group to the residue of the indicated compound.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7- membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl., oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl.

The term "substituted", as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

The term "peptide" as used herein means a compound that consists of two or more amino acids (as defined herein)that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Synthesis

Novel peptide boronic acids containing aliphatic sidechains were prepared by the series of reactions outlined in Scheme I. First, the precursor, $NH_2\text{-}CH[(CH_2)_n Br]BO_2\text{-}C_{10}H_{16}$, n=3 or 4, was prepared and coupled with an N-terminal protecting group or with an N-terminal and sidechain protected peptide by the procedure we have described previously [Kettner et al. *J. Biol. Chem.* 265 18289–18297 (1990)]. An example of this product is 1 where the above intermediate is coupled to Ac-(D)Phe-Pro—OH. 1 was converted to the corresponding alkyl cyanide 2 by treatment with tetrabutyl ammonium cyanide in THF at 55° C. for 2 hours. This appears to be a general method for introducing the cyano group. In contrast, other common methods of introducing this group can be applied only with limited success. For example, the reaction of Ac-(D)Phe-Pro-NH-CH[$(CH_2)_4$-Br]BO$_2$-C$_{10}$H$_{16}$ with KCN in N,N-dimethylformamide failed to yield a detectable product. Our data are consistent with the formation of a cyclic product arising from the nucleophilic displacement of the sidechain bromide by the adjacent amide NH. Treatment of Z-NH-CH[$(CH_2)_4$-Br]BO$_2$-C$_{10}$H$_{16}$ with NaCN in N,N-dimethylformamide gave the cyano compound, but only in low yield, indicating that cyclization does not occur quite so readily when the urethane protecting group (Z) is present. Typically, 2 was purified by standard techniques such as silica gel chromatography. The corresponding amidine, 3, was prepared by treating the nitrile with a saturated solution of a mineral acid such as HCl in methanol. Excess solvent and acid were removed by evaporation and the residue was allowed to react with anhydrous ammonia to yield the desired product.

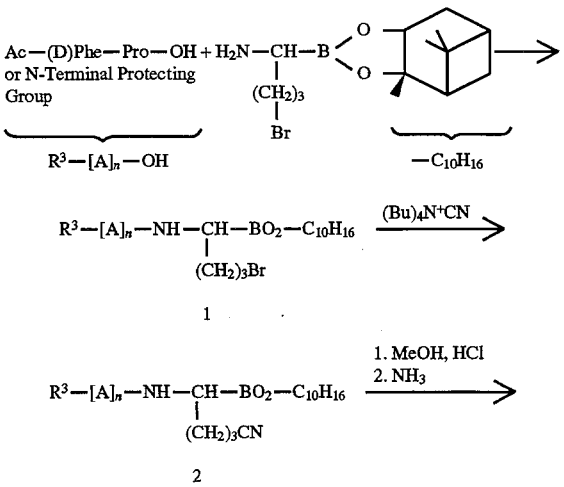

Scheme 1 -continued

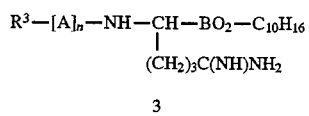

3

The formamidino substituted boronic acid, 5, was prepared by the synthesis of the corresponding alkyl amine such as Ac-(D)Phe-Pro-boroOrn-$C_{10}H_{16}$4, Scheme 2. This in turn was prepared by treating 1 with sodium azide followed by hydrogenation (Kettner et al., 1990). The amine, 4, was treated with ethyl formimidate to yield the formamidino compound, 5.

Scheme 2

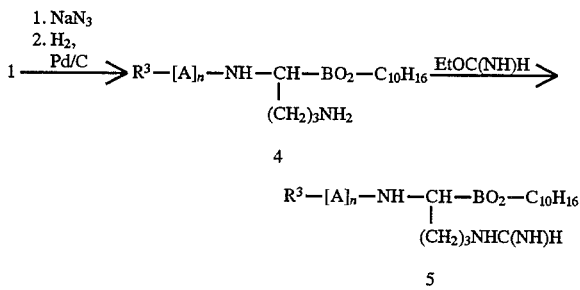

N-substituted isothiouronium derivatives and N-substituted guanidines are readily prepared as shown in Scheme 2a. Treatment of bromide 1 with a thiourea produces directly the isothiouronium 21. Alternatively 1 can be converted to the amine 4 as shown in Scheme 2. Employing a method originally described by Kim et al., *Tetrahedron Lett.* 29, 3183 (1988), the amine 4 then is heated with a formamidinesulfonic acid in the presence of 4-DMAP to afford the guanidine 22. The required formamidinesulfonic acids can be prepared by oxidation of the corresponding thioureas, see: Walter and Randau, *Liebigs Ann. Chem.* 722, 98 (1969).

nia in either THF or alcohol to yield the desired product.

Scheme 3

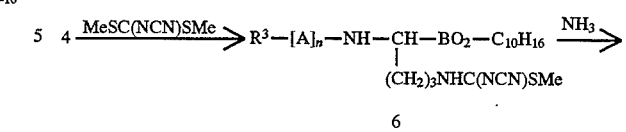

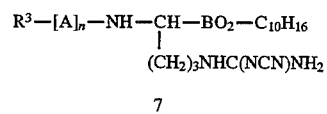

7

Hydroxyguanidino inhibitors are prepared by treating 4 with cyanogen bromide or cyanogen chloride followed by hydroxylamine to yield 8, Scheme 4. These are known chemical transformations, Nakahara et. al. *Tetrahedron,* 33, 1591 (1977)and Belzecki et al. *J. Chem. Soc. Chem. Commun.,* 806 (1970).

Scheme 4.

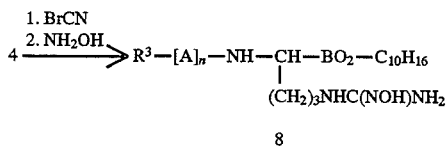

8

The preparation of new aromatic boronic acids are shown in Scheme 5. Functionalized benzylic anions containing either a halogen or cyano substituent (the cyano group is shown for illustration)are obtained by treatment with activated Zn metal in THF or other inert solvent and then with CuCN·2LiCl [Berk et al. *Organometallics* 9, 3053–3064 (1990)]. Dichloromethyl boronic acid pinanediol was prepared by the method described by Tsai et al. *Organometallics* 2, 1543–1545 (1983). It was allowed to react with the transmetalated anion to yield 9. This was the only acceptable method of preparing these functionalized benzylic anions. For example, treatment of p-nitrobenzyl chloride with

Scheme 2a

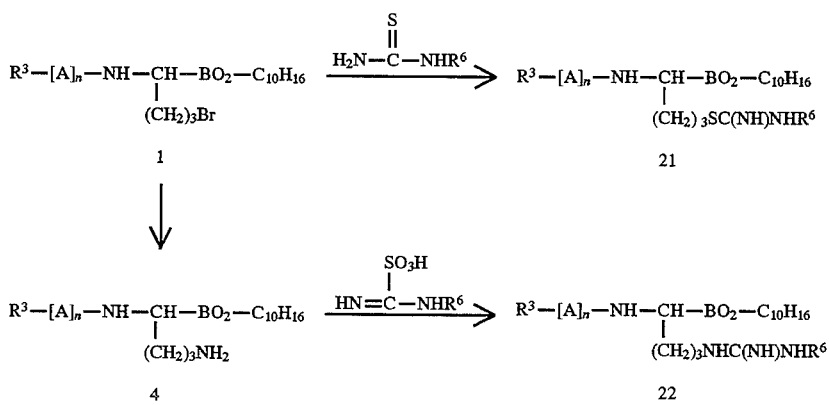

The substituted boronic acid, 7, is prepared by treating 4 with dimethyl cyanodithioiminocarbonate or diphenyl cyanodicarbonimiate to yield the S-methyl isourea (6) or O-phenyl isourea, respectively, using a procedure similar to that reported by Barpill et al. *J. Hereocyclic Chem.* 25, 1698 (1988), Scheme 3. This intermediate is treated with ammolithium metal using the method of Michel et al. *J. Organometallic Chem.* 204, 1–12 (1981) failed to yield an identifiable product. Similarly, treatment of p-cyanobenzyl chloride with lithium naphthalenide in the presence of $ZnCl_2$ using the conditions of Zhu et al. *J. Org. Chem.* 56, 1445–1453 (1991)did not give the desired product.

The α-aminoboronic acid, 10, was obtained by treating 9 with the lithium salt of hexamethyldisilazane and removing the trimethylsilanyl groups by treatment with anhydrous HCl. 10 was coupled to either an N-terminal protecting group or to a peptide using known techniques.

The aromatic substituted cyanides, 11, were converted to the corresponding amidino compound, 12, using the same sequence of reactions described for preparation of the aliphatic amidino compound, 3.

Scheme 5

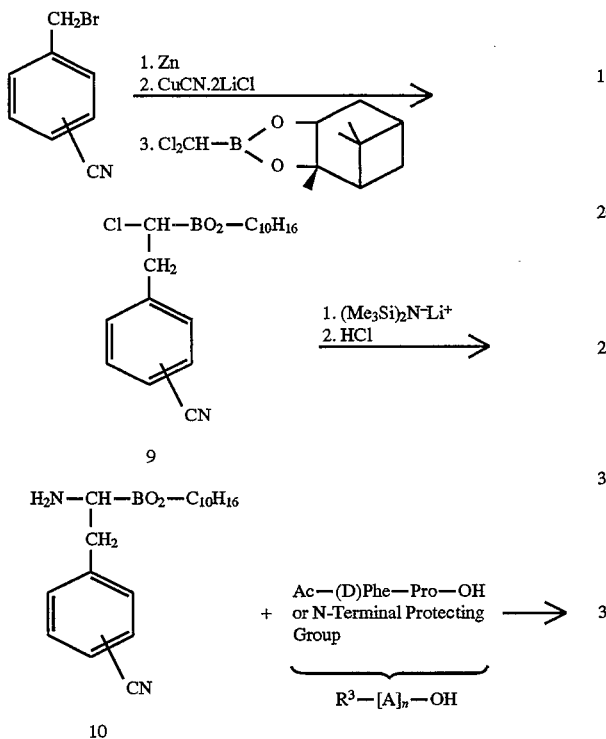

-continued
Scheme 5

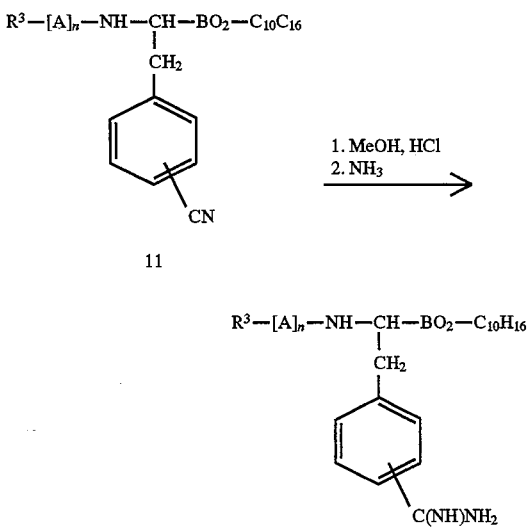

11 can be hydrogenated to yield the corresponding aminomethyl group as an aromatic substituent 13, Scheme 6. The corresponding formamidino, cyanoguanidino, hydroxyguanidino and guanidino compounds, 14, 15, 16, and 17, respectively, are prepared by the procedures described for the aliphatic series, Scheme 1.

Scheme 6

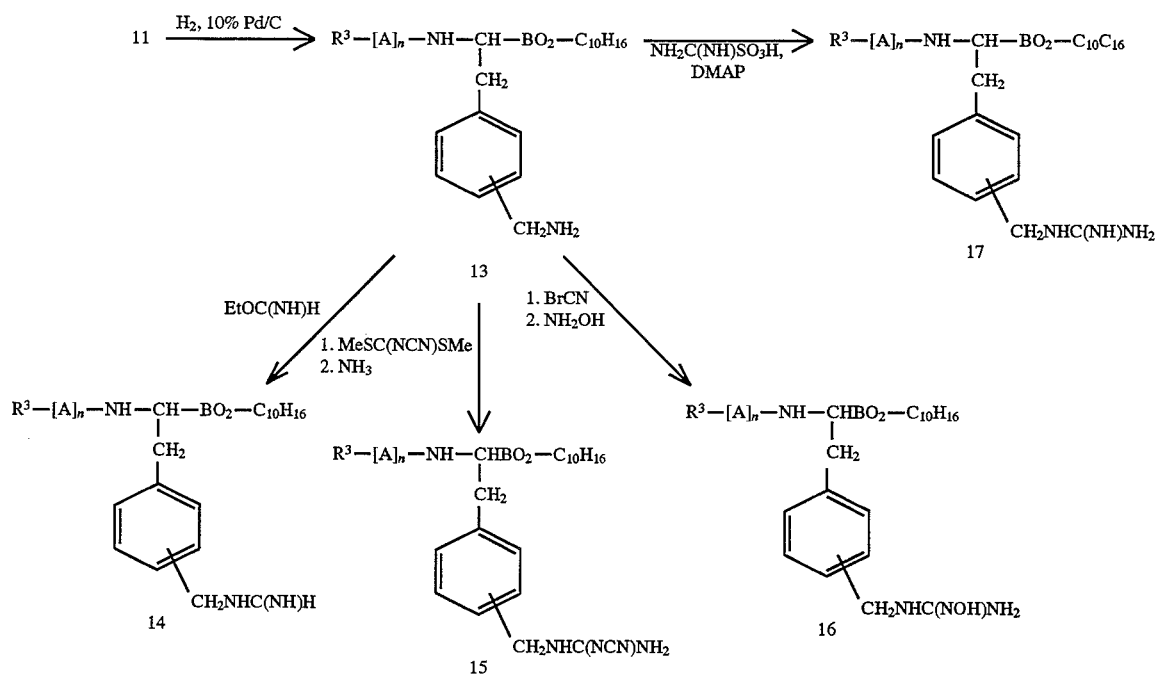

Aromatic guanidino inhibitors, 20, were prepared from precursor R-boroPhe-$C_{10}H_{16}$, Scheme 7. The aromatic ring was nitrated by reaction with $NO^+BF_4^-$ to yield 18 which was reduced to the corresponding amine, 19. The amine is converted to the guanidine by reaction with aminoiminomethane sulfonic acid [Mosher et al. *Tetrahedral Lett.* 29 3183 (1988)] or cyanamide (Kettner et al. 1990).

Scheme 7

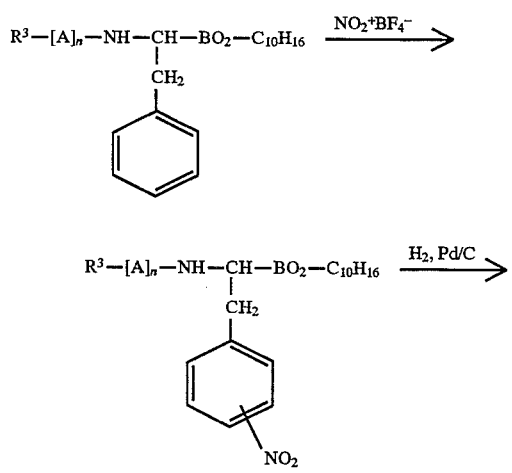

-continued
Scheme 7

Scheme 8 illustrates the preparation of thrombin inhibitors where the $P_1$ side chain is substituted with an alkoxy group, and where the N-terminus is derivatized with novel N-blocking groups. Treatment of $R^3$-$[A]_n$-NH-CH[$(CH_2)_3$—Br]$BO_2$-$C_{10}H_{16}$ with an alkoxide yielded the ether 20 in the $P_1$ site, as shown for Boc-(D) Phe-Pro-NH-CH[$(CH_2)_3$-Br]$BO_2$-$C_{10}H_{16}$ 1. Removal of the Boc protecting group yielded the free amine 23 which was further modified to give inhibitors with unique properties. The inhibitor 23 was obtained by reductive amination with glyoxylic acid and sodium cyanoborohydride using a procedure similar to the general described by Rosowsky J. Med.

Chem. 34, 1447, 1991. Similarly, reductive amination with formaldehyde yielded the N,N-dimethyl analog 24.

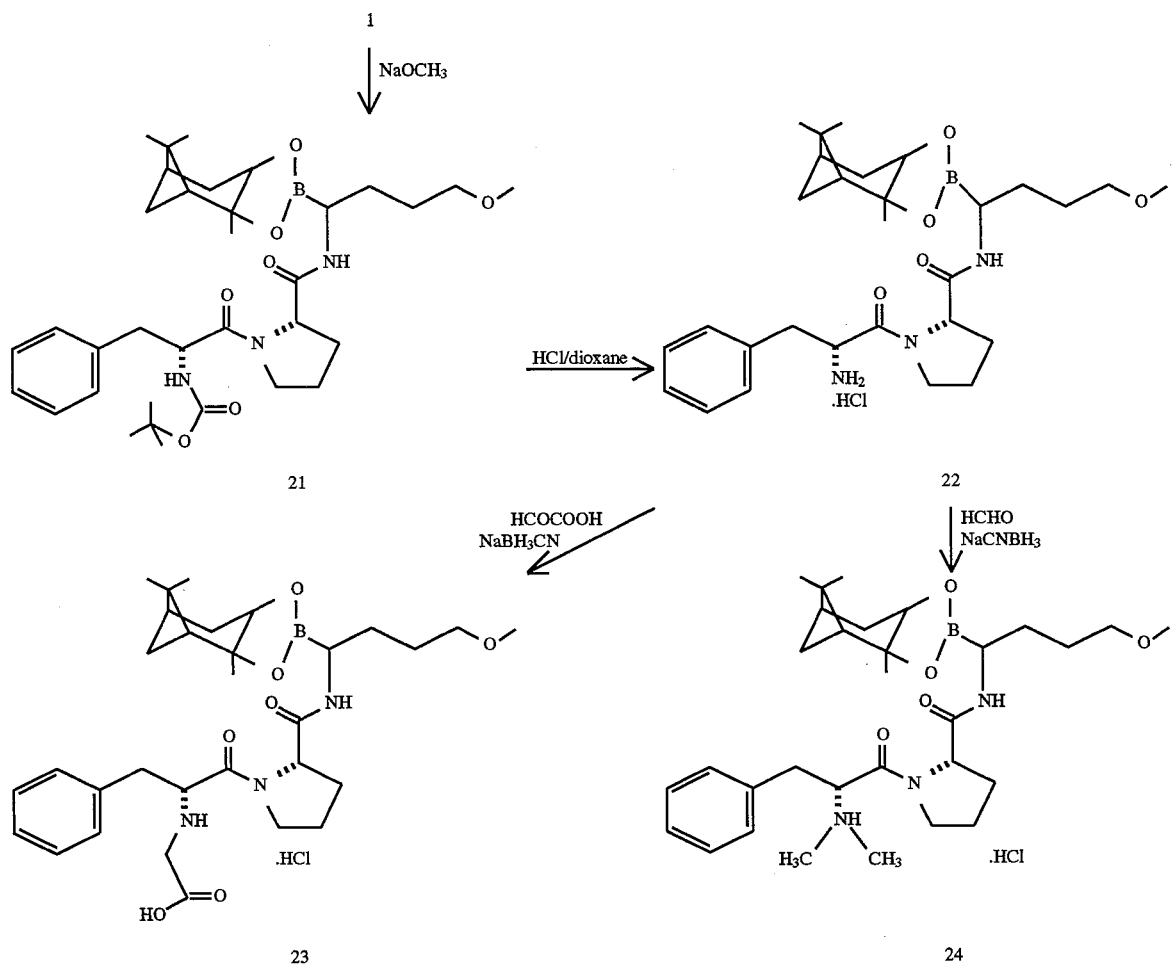

Scheme 8.

The boroOrn ester 4 was the starting material inhibitors with side chain amides (26), sulfonamides (27), α-hydroxyamides (28) and ureas (29) at the $P_1$ side chain (Scheme 9). The latter compounds were obtained by treatment of 4 with potassium cyanate in alcohol using conditions similar to those described by Frimpong-Manso et al. J. Heterocyclic Chem. 29, 221, 1992.

Scheme 9.

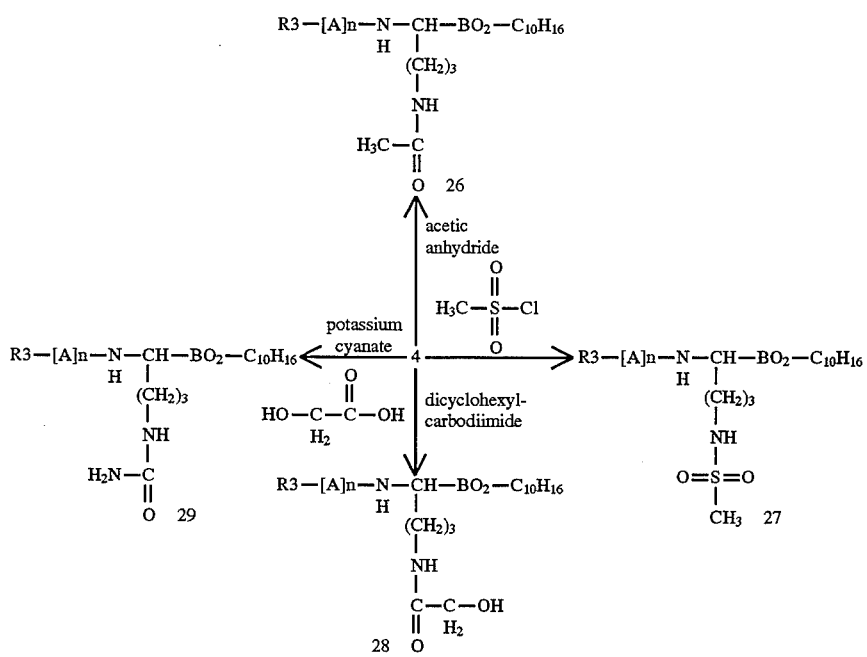

Inhibitors of this invention with modified guanidino groups at $P_1$ were prepared using procedures described previously for the preparation of Cimetidine (Durant et al. J. Med. Chem. 20 901, 1977)(Scheme 10). 4 was reacted with dimethylcyanodithio-imidocarbonate to give 31. Treatment of 31 with either ammonia, an alkyl amine, or an N,N-dialkyl amine yielded the corresponding cyanoguanidine (32a), N-alkyl cyanoguanidine (32b), and N,N-dialkyl cyanoguanidine (32c), respectively. The peptide portion of the molecule was modified to yield a variety of inhibitors. For example, when $R^3$ of 32 was Boc, treatment with anhydrous HCl gave a free amino group which was carboxymethylated with HCOCOOH and NaCNBH$_3$ according to the general procedure described by Martin et al J. Med. Chem. 8, 456, 1965. The alkyl halide 1 was allowed to react with N-hydroxyphthalimide in DMF in the presence of triethylamine at 100° C. to yield 34. The phthalamido group was removed by treatment with hydrazine in methylene chloride and methanol to give the aminooxy compound 35. The aminooxy group of 35 was converted to the guanidinooxy group of 36 by heating with cyanamide in toluene. Other methods of guanidation described in the present case can also applied here to form the desired compound 36.

Scheme 10.

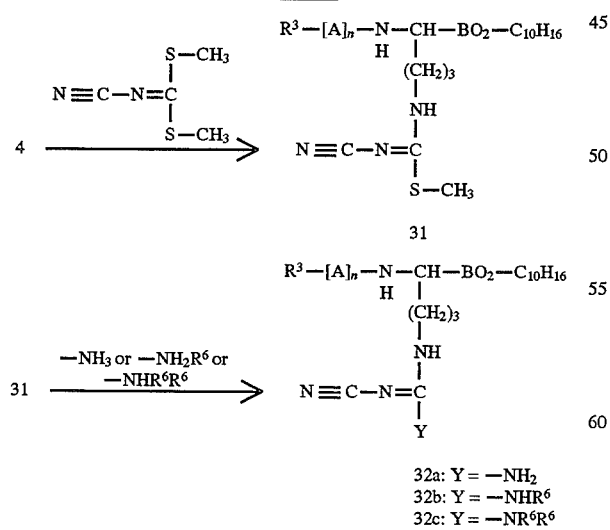

Scheme 11.

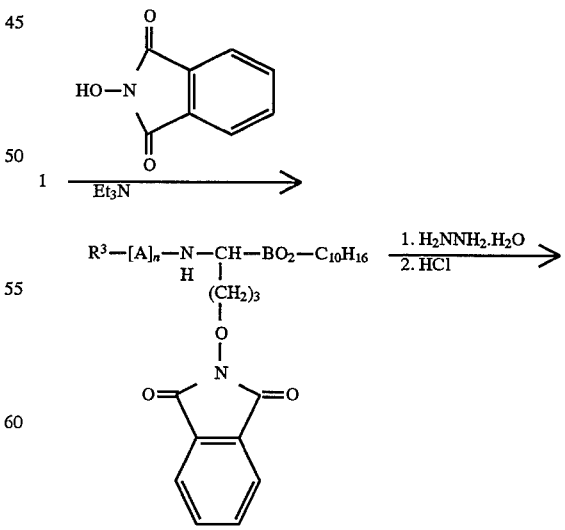

Scheme 11 shows the preparation of inhibitors wherein X is an aminooxy or guanidinooxy group. These were prepared -continued
Scheme 11.

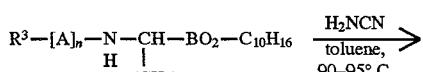

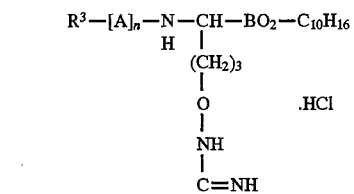

-continued
Scheme 12.

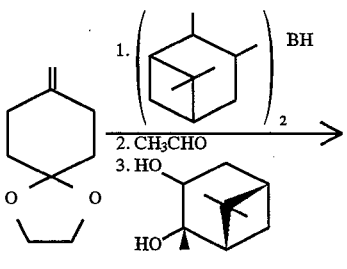

39

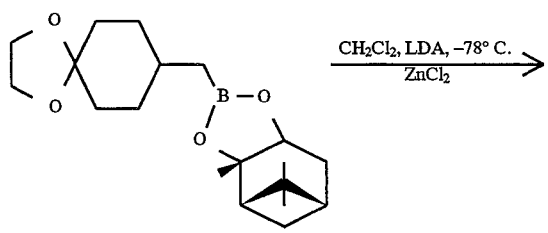

40

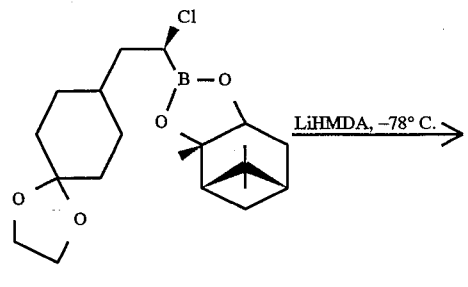

41

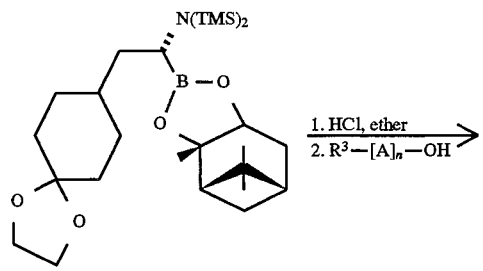

42

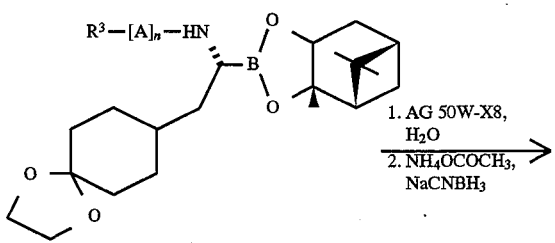

43

Scheme 12 illustrates the preparation of boronic acid analogs containing a substituted cyclohexyl ring in the $P_1$ site. Cyclohexadione monoethylene ketone 38 was converted to the alkene 39 using a Wittig reaction. 39 was hydroboronated using diiisopinocamphyl borane and converted to the boronic acid ethyl ester using the general procedure described by Brown et al. J. Org. Chem. 47, 5065, 1982. Transesterification with pinanediol gave 40. The α-chloro compound 41 was prepared by the homologation reaction of 40 with the anion of methylene chloride using the procedure of Matteson et al. J. Am. Chem. Soc. 105, 2077, 1983. Nucleophillic displacement of the α-chloride with the lithium salt of hexamethyldisilazane gave the bis-silyl protected amine 42. The trimethylsilyl protecting groups were removed by treatment with anhydrous HCl. The α-amino group was coupled to either an acyl group or N-protected peptide or amino acid using the mixed anhydride or other standard peptide coupling reaction conditions. The peptide 43 was treated with an aqueous suspension of a sulfonic acid substituted ion exchange resin to yield the side chain ketone which was converted to the amino cyclohexylpeptide 44 by reductive amination using ammonium acetate and sodium cyanoborohydride.

Scheme 12.

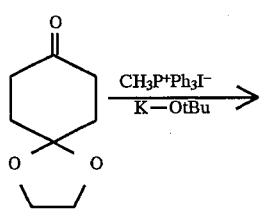

38

-continued
Scheme 12.

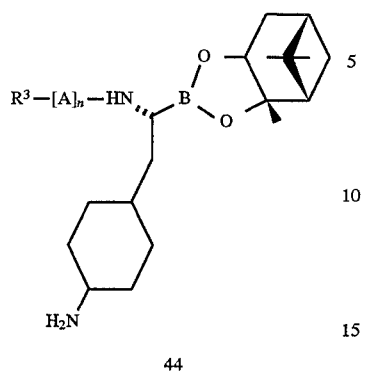

44

Scheme 13 shows the preparation of boronic acid peptides containing a cyclohexyl residue in the $P_1$ site by a modified procedure for the preparation of 44. The ketal, 47, was prepared by the procedure of Laronze Synthetic Communications 21 881, 1991. Hydroboration and transesterifcation with R-pinanediol yielded both the 1,4- (48)and 1,3- disubstituted (49) boronic acid esters. 48 was converted to the corresponding amine 50 using the reaction pathway described for 44.

Scheme 13.

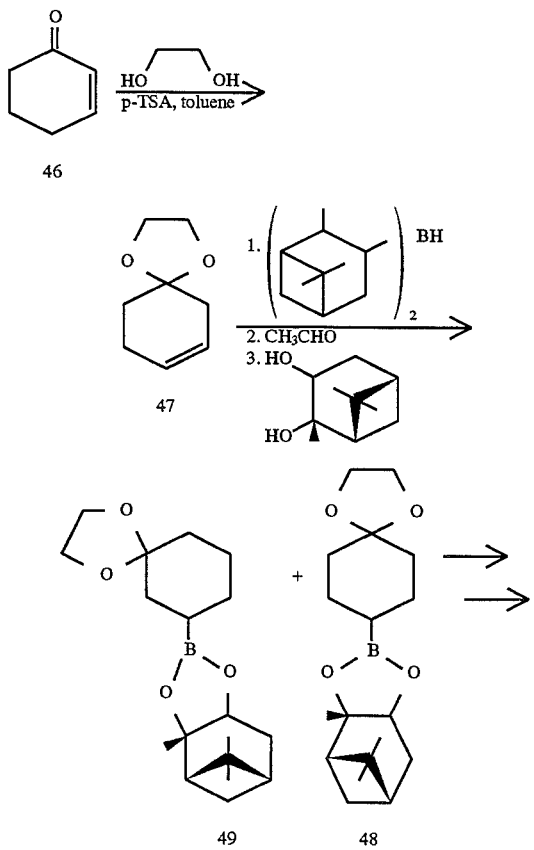

-continued
Scheme 13.

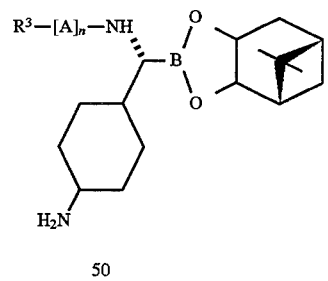

50

Compounds of the invention where R1 is an alkylcyclohexyl group and X is a hydroxide, formamidine, or guanidine were prepared according to Scheme 14. Compound 52 was prepared from 43 by treatment of 43 with a sulfonic acid substituted ion exchange resin. 52 was converted to 53 by reduction with $NaBH_4$. To form the guanidino substituted compound 55, 50 was treated with aminoiminomethane sulfonic acid according to Scheme 7. The formamidino analog 56 was prepared by treatment of 50 with ethyl formimidate according to Scheme 6.

Scheme 14.

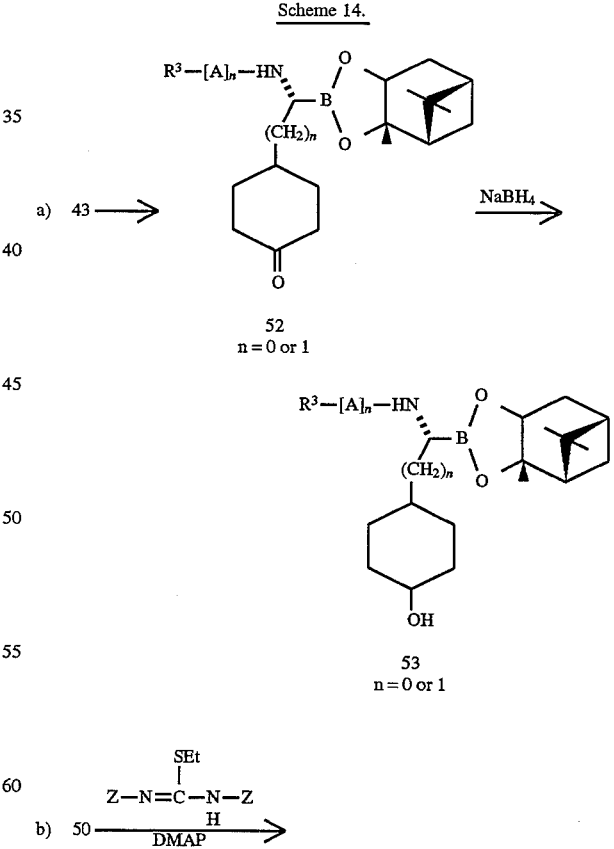

Scheme 14. (continued)

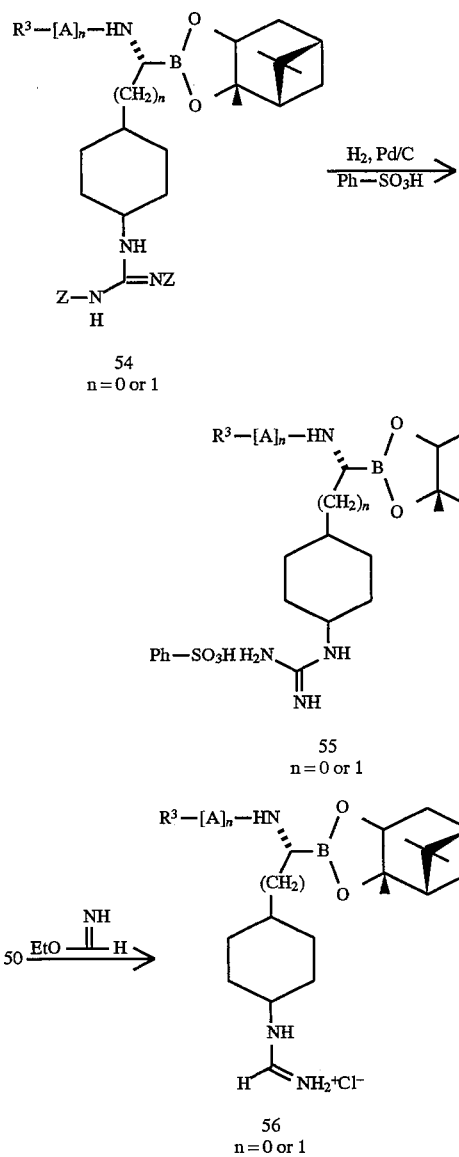

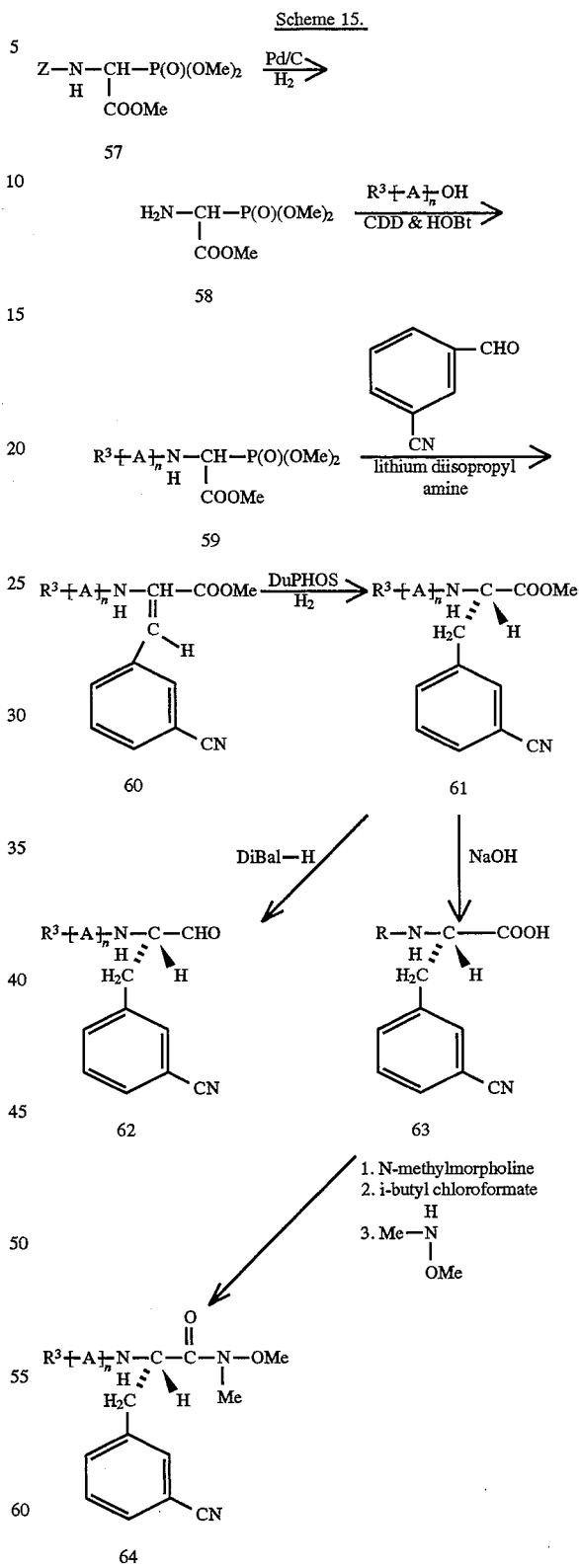

aldehyde 62 according to the procedure of Nahm and Weinreb Tetrahedron Lett 22, 3815, 1981.

Compounds of the present invention where $R^1$ is a substituted benzyl group and E is a nonboronic acid/ester electrophilic group, such as —$CO_2CH_3$, —CHO, —$CO_2H$, and —$CON(CH_3)OCH_3$, were prepared according to Scheme 15 from the corresponding substituted phenylalanine ester 61 by following the procedure described by Schmidt et al Synthesis 53, 1984. Accordingly, 57 was catalytically hydrogenated with Pd/C to 58 which was coupled to $R^3$-[A]n—OH, under standard peptide forming conditions, to form 59. Treatment of 59 with the substituted aldehyde 65 in the presence of lithium diisopropylamine yielded 60. Hydrogenation of 60 in the presence of a chiral catalyst, such as DuPhos™, gave 61. Either the R or S isomer could be obtained by the stereo specific hydrogenation of 60 according to the procedure of Burk et al J. Am. Chem. Soc. 115, 10125, 1993. 61 was then converted to the aldehyde 62 by treatment with diisobutyl aluminum hydride. The acid 63 was made from 61 by treatment with aqueous base. 63 was then converted to 64 by treatment of the mixed anhydride of 63 with N-methoxy-N-methylamine. 63 can also be readily reduced with $LiAlH_4$ to give the corresponding peptide Inhibitors of the invention wherein E is —COC(=$CH_2$)OEt, —COCOOEt, —COCOOH, —COCOCH$_3$, OR —COCONR15R16 are prepared according to Scheme 16 by following the procedure of Angelastro et al. J. org. Chem.

54, 3913, 1988. Thus 64 was converted to the corresponding vinyl ketone 67 by treatment with the lithium salt of ethyl vinyl either. The ketone ethyl ester 68 is obtained by ozonolysis of the double bond. The corresponding carboxylic acid 69 is obtained by base hydrolysis of 68. Acid hydrolysis of 70 gives the diketone 70. The corresponding amides are prepared using the procedure described by Li et al. J. Med. Chem. 36 3472, 1993. The keto function of the keto ethyl ester 71 is protected as the 1,3-dithiolane 72 and treated with either ammonia, a primary, or secondary amine to give corresponding keto amides 73. The bisketo-carboxylic acid esters of this invention are prepared by the procedure of Wasserman Vu Tetrahedron Lett. 31, 5205 1990.

Scheme 16.

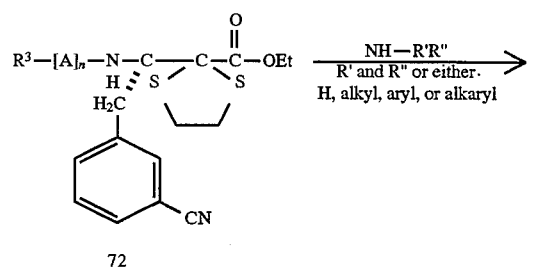

Scheme 17 shows the preparation of nonboronic acid inhibitors wherein E is an α-ketobenzoxazoline 75, oxazoline 76, α-diazoketone 77, α-monohaloketone 78, and α-trihalomethylketone 79. Thus according to the procedure of Edwards et al J. Am. Chem. Soc. 114, 1855, 1992, 75 and 76 are prepared from 62. 77 is prepared by treatment of the mixed anhydride of 63 with diazomethane using the general procedure of Kettner and Shaw Methods Enzymol. 80, 826, 1981. 77 is then converted to 78 by reaction with an acid halide using the procedure described by Angliker et al. Biochem J. 241, 871, 1987. 79 is prepared from 63 by a modification of the Dakin-West reaction (Dakin and West J. Biol. Chem. 78, 91, 1928) described by Kolb et al Tetrahedron Lett. 27 1579, 1986.

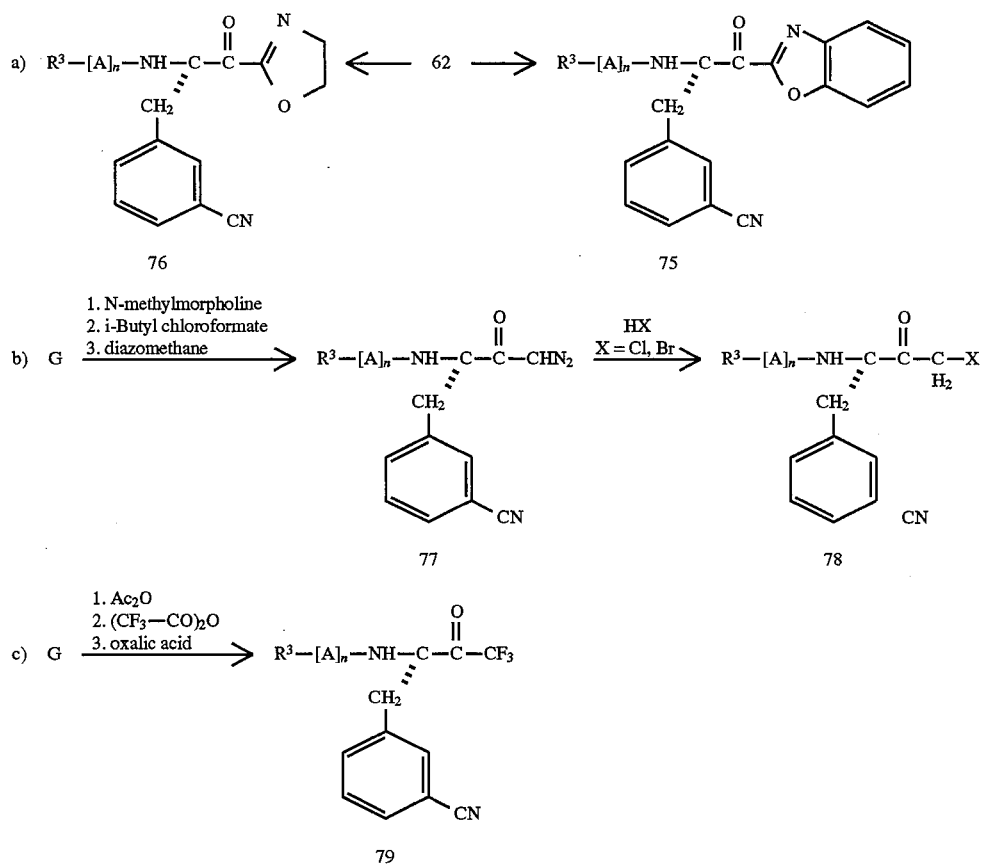

In an alternate synthesis, the trifluoromethyl ketone analog 85 was prepared using a procedure similar to that described by Imperial and Abeles Tetrahedron Lett. 27, 135, 1986. (Scheme 18) mCyanobenzaldehyde was condensed with nitromethane to give the nitrostyrene 81 which was reduced with NaBH$_4$ using the method Bhattachariya et al. Synthesis 886, 1985. The anion of the nitroalkane was added to the ethyl hemiacetal of trifluoroacetaldehyde to yield 82. The nitro group of 82 was selectively reduced to give the α-amino alcohol 83 using Na$_2$S$_2$O$_3$. 83 is then coupled to an N-protected amino acid or peptide to give 84 which was then oxidized to the trifluoromethyl ketone 85.

Scheme 18.

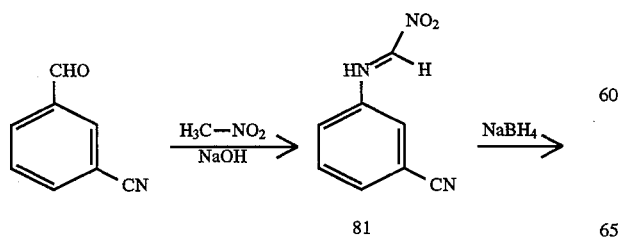

-continued
Scheme 18.

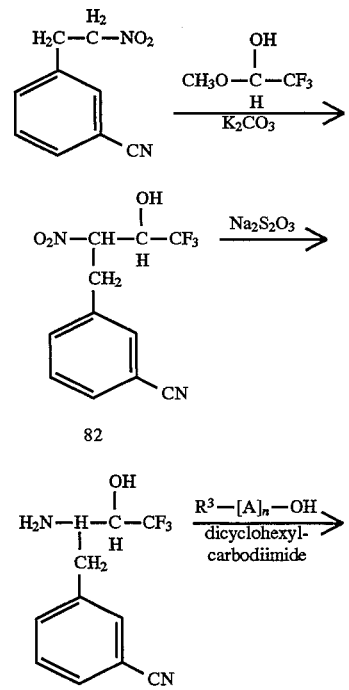

-continued
Scheme 18.

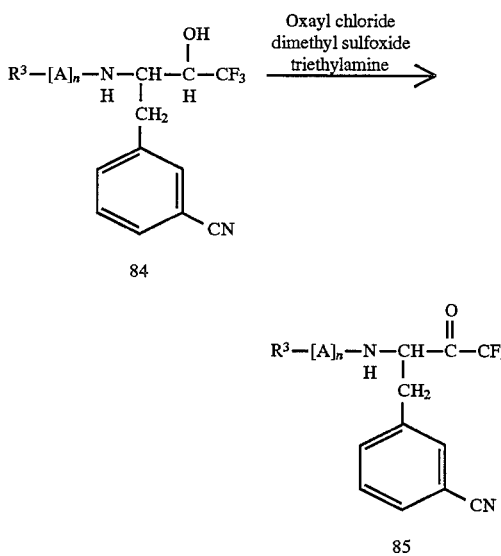

84

85

NMR, proton nuclear magnetic resonance, chemical shifts are reported in δ units, parts per million downfield from the internal tetramethylsilane standard. Elemental analyses were conducted by Galbraith Laboratories Inc., Knoxville, Tenn. and Microanalysis Inc., Wilmington, Del. FAB/MS samples of free boronic acids did not give consistent results making it difficult to monitor the removal of ester protecting groups by this means. However, the presence of the pinanediol and the pinacol groups are readily observed in NMR spectra. For the pinanediol ester, a methyl group is observed at δ 0.9 and the methyl groups of the pinacol groups are observed as singlet at δ 1.1. Following the removal of pinanediol protecting group, MS were run by treating the sample with ~2 equivalents of pinacol in methanol for 5 minutes and evaporating the solvent. Similarly, MS samples of free boronic acid, obtained by removal of the pinacol, were prepared by treating with pinanediol. In some cases, ethylene glycol was used as a matrix for mass spectroscopy to yield the boronic acid-ethyleneglycol ester (designated EG ester). For the subsequent Example see Table 1 for analytical data.

EXAMPLE 1

Synthesis of Ac-(D)Phe-Pro-NH-CH[(CH$_2$)$_4$CN]BO$_2$-C$_{10}$H$_{16}$

The intermediate, Ac-(D)Phe-Pro-NH-CH[(CH$_2$)$_4$Br]BO$_2$-C$_{10}$H$_{16}$, was prepared using the mixed anhydride procedure. Ac-(D)Phe-Pro—OH (3.04 g, 10 mmol) was dissolved in 50 mL of THF and N-methylmorpholine (1.1 mL, 10 mmol) was added. The solution was cooled to −20° C. using a CCl$_4$ dry ice bath and isobutyl chloroformate (1.30 mL, 10 mmol) was added. After 5 min at −20° C., the mixture was added to NH$_2$-CH[(CH$_2$)$_4$Br]BO$_2$-C$_{10}$H$_{16}$·HCl (3.81 g, 10 mmol) which was dissolved in 20 mL of THF and precooled to −20° C. Triethylamine (1.39 mL, 10 mmol) was added and the mixture was allowed to stir for 1 h at −20° C. and 2 h at room temperature. Insoluble material was removed by filtration and the filtrate was evaporated under a reduced pressure. The residue was dissolved in 50 mL of ethyl acetate and washed subsequently with 75 mL of 0.2N HCl, 5% NaHCO$_3$, and saturated aqueous sodium chloride. The organic phase was dried over Na$_2$SO$_4$ and concentrated in vacuo to give Ac-(D)Phe-Pro-NHCH[(CH$_2$)$_4$Br]BO$_2$-C$_{10}$H$_{16}$ (6.01 g, 95% yield).

The bromide (1.89 g, 3.0 mmol) and tetra-n-butyl ammonium cyanide (3.2 g, 11.8 mmol, 4 eq) were dissolved in 50 mL of acetonitrile. This solution was heated at 90° C. for 3 h and solvent was removed under reduced pressure. The residue was dissolved in 50 mL of ethyl acetate and was washed with three 50 mL portions of saturated aqueous NaCl. The ethyl acetate solution was dried over anhydrous Na$_2$SO$_4$ and evaporated to give 2.5 g of crude product. It was purified by silica gel chromatography using 5% MeOH in CHCl$_3$ as an eluent to yield the desired product (0.50 g, 29% yield).

LRMS (NH$_3$-CI) m/e calcd. for M (C$_{32}$H$_{45}$N$_4$O$_5$B)+NH$_4^+$: 594.4. Found: 594. HRMS (NH$_3$-CI) m/e calcd. for M (C$_{32}$H$_{45}$N$_4$O$_5$B)+H$^+$: 577.3561. Found: 577.3555.

EXAMPLE 2

Synthesis of AC-(D)Phe-Pro-NHCH[(CH$_2$)$_4$C(NH)NH$_2$]-BO$_2$-C$_{10}$H$_{16}$·benzene sulfonic acid The nitrile, (Example 1, 0.40 g, 0.70 mmol), was dissolved in 50 mL of a cold solution of saturated HCl in methanol and the solution was stirred overnight at 4° C. The solution was then concentrated under reduced pressure. The residue was dissolved in anhydrous methanol (50 mL), gaseous NH$_3$ was bubbled through the solution for 1 h, and the solution was heated at 50° C. for 3 h. Solvent was evaporated, the residue was suspended in minimum volume of methanol, and 0.11 g of benzenesulfonic acid (1 eq) was added. Methanol was evaporated and the residue was triturated with hexane to yield the desired product as a pale yellow powder (0.52 g, 99% yield).

FABMS: m/e calculated for M (C$_{32}$H$_{48}$N$_5$O$_5$B)+H$^+$: 594.38. Found: 594.14. HRMS(NH$_3$-CI) m/e calcd for M (C$_{32}$H$_{48}$N$_5$O$_5$B)+H$^+$: 594.3827. Found: 594.3824.

EXAMPLE 3

Synthesis of Ac-(D)Phe-Pro-NHCH[(CH$_2$)$_3$NHC(NH)H]BO$_2$-C$_{10}$H$_{16}$ or Ac-(D) Phe-Pro-boroOrn (CH=NH)-C$_{10}$H$_{16}$ Ethyl formimidate·HCl was prepared by the procedure of Ohme and Schmitz Angew. Chem. Internat. Edit. 6 566 (1967) and Ac-(D)Phe-Pro-boroOrn-C$_{10}$H$_{16}$ was prepared by the procedure of Kettner et al. (1990). The formimidate (1.29 g, 11.7 mmol) and 4-N,N-dimethylaminopyridine (1.44 g) were added to a solution of Ac-(D)Phe-Pro-boroOrn-C10H16·BSA (2.78 g, 3.92 mmol) dissolved in 40 mL of ethanol. The resulting solution was refluxed for 8 h. After removal of solvent, the residue was purified by chromatography using a column of Sephedex™LH 20 and methanol as a solvent to give pure product (1.28 g, 56% yield).

HRMS(NH$_3$-CI) m/e calcd. for M (C$_{31}$H$_{46}$BN$_5$O$_5$)+H$^+$: 580.3670. Found: 580.3679.

EXAMPLE 4

Synthesis of Ac-(D)Phe-Pro-NHCH[(CH$_2$)$_3$-NHC(NH)H]B(OH)$_2$

The pinanediol protecting group on the boronic acid portion of Ac-(D)Phe-Pro-NHCH[(CH$_2$)$_3$-NHC(NH)H]-BO$_2$-C$_{10}$H$_{16}$·HCl (Example 3) was removed by transesterification using the procedure we have described previously in U.S. application Ser. No. 08/010731. The pinanediol ester (0.30 g, 0.51 mmol) and phenyl boronic acid (0.31 g, 2.6 mmol) were suspended in 10 mL of a 1:1 mixture of ether and water and was allowed to stir for 2.5 h at room temperature. The phases were separated and the aqueous phase was extensively washed with ether. The aqueous phase was evaporated to yield a solid. This material was triturated with ether to give the desired product as an amorphous white solid, 0.20 g (83% yield). LRMS (NH3-CI) m/e calcd. for the pinacol ester M ($C_{27}H_{42}N_5O_5B$)+$H^+$: 528.3. Found: 528. HRMS ($NH_3$-CI) m/e calcd. for the pinacol ester M ($C_{27}H_{42}N_5O_5B$)+$H^+$: 528.3357. Found: 528.3347.

EXAMPLE 5

Synthesis of Boc-Pro-NHCH[($CH_2$)$_3$NHC(NH)H]$BO_2$-$C_{10}H_{16}$

Boc-Pro-boroOrn-$C_{10}H_{16}$·BSA was also prepared by the procedure described previously (Kettner et al. 1990). This peptide (3.0 g, 6.5 mmol) was dissolved in 25 mL of absolute ethanol, 4-N,N-dimethylaminopyridine (1.6 g, 12.9 mmol) and ethyl formimidate·HCl (1.4 g, 12.9 mmol) were added. The solution was heated on a 85° C. oil bath for 1 h. Solvent was evaporated and the residue was dissolved in methanol and was chromatogramed on a 2.5×100 cm column of LH20 in methanol to yield 1.3 g of the desired product.

LRMS ($NH_3$-CI) m/e calcd. for M ($C_{25}H_{43}N_4O_5B$)+$H^+$: 491.5. Found: 491.

EXAMPLE 6

Synthesis of Boc-(D)Phe-Pro-NHCH[($CH_2$)$_3$-NHC(NH)H]$BO_2$-$C_{10}H_{16}$

The reaction was run using the procedure described for Example 3. Boc-(D)Phe-Pro-boroOrn-$C_{10}H_{16}$·BSA (3.7 g, 4.78 mmol), 4-N,N-dimethylaminopyridine (1.71 g, 13.8 mmol), and ethyl formimidate·HCl (1.54 g, 13.8 mmol) were dissolved in 50 mL of absolute ethanol and was heated at 85° C. for 7 h. The desired product was obtained by chromatography on a column of LH 20 in a yield of 1.56 g.

HRMS ($NH_3$-CI) m/e calcd for M ($C_{34}H_{52}N_5O_6B$)+$H^+$: 638.4089. Found: 638.4082.

EXAMPLE 7

Synthesis of Boc-(D)Phe-Pro-NHCH[($CH_2$)$_3$-NHC(NH)H]B(OH)$_2$

Boc-(D)Phe-Pro-NHCH[($CH_2$)$_3$-NHC(NH)H]$BO_2$-$C_{10}H_{16}$·0.40 BSA, 0.60 HCl (Example 6, 0.16 g, 0.22 mmol) and phenyl boronic acid (0.13 g, 1.1 mmol) were placed in mixture of 5 mL of ether and 5 mL of water and was allowed to stir for 4 h at room temperature. The phases were separated and the organic phase was washed with 5 mL of water. The combined aqueous phases were extensively washed with ether. The aqueous phase was evaporated and the residue triturated with ether to yield the desired product as a white solid, 0.10 g. LRMS ($NH_3$-CI) m/e calcd. for the pinacol ester M ($C_{30}H_{48}N_5O_6B$)+$H^+$: 586.4. Found: 586. HRMS ($NH_3$-CI) m/e calcd. for the pinacol ester M ($C_{30}H_{48}N_5O_6B$)+$H^+$: 586.3776. Found: 586.3772.

EXAMPLE 8

Synthesis of H-(D)Phe-Pro-NHCH[($CH_2$)$_3$-NHC(NH)H]$BO_2$-$C_{10}H_{16}$·2HCl

Boc-(D)Phe-Pro-NHCH[($CH_2$)$_3$-NHC(NH)H]$BO_2$-$C_{10}H_{16}$·0.40 BSA, 0.60 HCl (Example 6, 0.20 g, 0.25 mmol) was dissolved in 2 mL of 4N HCl: dioxane and was allowed to stir for 1 h at room temperature. Solvent was evaporated and the residue was triturated with ether to yield 0.18 g of the desired product.

HRMS (NH3-CI) m/e calcd for M ($C_{29}H_{44}N_5O_4B$)+$H^+$: 538.3565. Found: 538.3569.

EXAMPLE 9

Synthesis of H-(D)Phe-Pro-NHCH[($CH_2$)$_3$-NHC(NH)H]B(OH)$_2$

H-(D)Phe-Pro-NH-CH[($CH_2$)$_3$-NH-C(NH)H]$BO_2$-$C_{10}H_{16}$·0.35 BSA, 0.65 HCl (Example 8, 0.10 g, 0.16 mmol) was allowed to react with phenyl boronic acid according to the procedure in Example 4 to yield the desired product, 0.053 g. LRMS ($NH_3$-CI) m/e calcd. for the pinacol ester M ($C_{25}H_{40}N_5O_4B$)+$H^+$: 486.3. Found: 486. HRMS ($NH_3$-CI) m/e calcd for pinacol ester M ($C_{25}H_{40}N_5O_4B$)+$H^+$: 486.3251. Found: 486.3255.

EXAMPLE 10

Synthesis of $H_2$NCH[$CH_2C_6H_4$-m-CN] $BO_2C_{10}H_{16}$·HCl or H-boroPhe(m-CN)-$C_{10}H_{16}$·HCl The first intermediate, Cl-CH[$CH_2$-(m-cyanophenyl)]$BO_2$-$C_{10}H_{16}$, was prepared from m-cyanobenzyl bromide and dichloromethyl boronate pinanediol. Zinc dust (1.0 g) in 1 mL of THF was cooled to 0°–5° C. and a solution of m-cyanobenzyl bromide (1.37 g, 7.0 mmol) in 7 mL of THF was added dropwise (5 sec/drop). The reaction mixture was allowed to stir at 5° C. for 2 h. A mixture consisting of LiBr (1.22 g, 14 mmol), CuCN (0.63 g, 7.0 mmol), and 6 mL of THF was placed in a 50 ml flask and cooled to –40° C.; then the benzylic organozinc reagent was added by cannulation. The mixture was allowed to warm to –20° C. and stir for 5 min. It was cooled to –78° C. and neat dichloromethyl boronic acid pinanediol (1.47 g, 5.6 mmol) was added dropwise. The resulting mixture was stirred at –78° C. for 2 h and at room temperature for 2 days. Saturated aqueous $NH_4Cl$ (20 mL) was added to the mixture and the aqueous solution was extracted with three 20 ml portions of ether. The combined organic layers was dried over anhydrous $MgSO_4$ and evaporated in vacuo to give crude compound (1.8 g). It was purified by silica gel chromatography where the column was stepwise eluted with hexane (100 mL) and then 15% ether in hexane (200 mL) to give the desired product 0.53 g (27% yield). LRMS($NH_3$-CI) m/e calcd. for M ($C_{19}H_{23}NO_2BCl$)+$NH_4^+$: 361.2. Found: 361.1.

To a solution of hexamethyldisilazane (0.21 mL, 0.98 mmol) in 2 mL of THF at –78° C. was added n-butyllithium (1.45M, 0.67 mL, 0.98 mmol). The solution was allowed to slowly warm to room temperature to ensure the anion generation was complete. The resulting solution was then cooled to –78° C. and Cl—CH[$CH_2$-(m—cyanophenyl)]BO2-$C_{10}H_{16}$ (0.33 g, 0.98 mmol) in 2 mL of THF was added. The mixture was allowed to warm to room temperature and to stir overnight. Solvent was evaporated and 8 mL of hexane was added to give a suspension. HCl in dioxane (4.1N, 1.5 mL, 6.0 mmol) was added at –78° C. The mixture was slowly warmed to room temperature and stirred for 2 h. Additional hexane (6 mL) was added and crude product was isolated as a precipitate. This product was dissolved in chloroform and insoluble material was removed by filtration. The flitrate was evaporated at a reduced pressure to give an oil (~0.2 g). Final purification was achieved by chromatography on a column of Sephedex™ LH 20 column using methanol as a solvent. H-boroPhe(m-CN)-$C_{10}H_{16}$·HCl was obtained as an oil (0.12 g, 34% yield). HRMS(NH$_3$-CI) m/e calcd. for M $(C_{19}H_{26}BN_2O_2)$+H$^+$: 325.2087. Found: 325.2094.

EXAMPLE 11

Synthesis of Ac-(D)Phe-Pro-boroPhe(m-CN)-$C_{10}H_{16}$

Ac-(D)Phe-Pro—OH (0.10 g, 0.33 mmol) and N-methylmorpholine (0.037 mL, 0.33 mmol) were allowed to react with isobutyl chloroformate (0.043 mL, 0.33 mmol) in 5 mL of THF at −20° C. After 5 rain, H-boroPhe(m-CN)-$C_{10}H_{16}$·HCl, (Example 10, 0.12 g, 0.33 mmol) dissolved in 3 mL of cold THF and triethylamine (0.046 mL, 0.33 mmol) were added. The mixture was allowed to stir at −20° C. for 1 h and to stir at room temperature for an additional hour. Insoluble material was removed by filtration and solvent was evaporated. The residue was dissolved in ethyl acetate and was washed with 0.20N HCl, 5% NaHCO$_3$, and saturated aqueous NaCl. The organic layer was dried over anhydrous Na$_2$SO$_4$ and was evaporated in vacuo to give 0.2 g of an oil. It was purified by chromatography on a column of Sephedex™ LH 20 yielding 0.13 g of desired product (65% yield). HRMS(NH$_3$-CI) m/e calcd. for M $(C_{35}H_{43}BN_4O_5)$+H$^+$: 611.3405. Found: 611.3416.

EXAMPLE 12

Synthesis of AC-(D)Phe-Pro-boroPhe[m-C(NH)NH$_2$]-$C_{10}H_{16}$

Ac-(D)Phe-Pro-boroPhe(m-CN)-$C_{10}H_{16}$, Example 11, (50 mg) was dissolved in 5 mL of saturated solution of HCl in methanol. The solution was allowed to stir overnight at 4° C. After removal of solvent, the residue was resuspended in 5 mL of anhydrous methanol, cooled to 0° C., and anhydrous NH$_3$ was bubbled through the solution for 0.5 h. It was heated at 60° C. for 6.2 h. Solvent was evaporated and one equivalent of benzene sulfonic acid (13 mg) and 1 mL of methanol were added. Solvent was evaporated under N$_2$ and the product was triturated with ether to give the desired product as a pale brown powder (65 mg, 100% yield). HRMS(NH$_3$-CI) m/e calcd. for M $(C_{35}H_{47}BN_5O_5)$+H$^+$: 628.3670. Found: 628.3688.

EXAMPLE 13

Synthesis of Ac-(D)Phe-Pro-boroPhe(m-CH$_2$NH$_2$)-$C_{10}H_{16}$

Ac-(D)Phe-Pro-boroPhe(m-CN)-$C_{10}H_{16}$ was placed in 5 mL of methanol, 10% Pd/C(25 mg) and 0.1N HCl (0.41 mL) were added, and the mixture was stir under H$_2$ at room temperature for 2.5 h. The solution was filtered through Celite and washed with 20 mL of methanol. The filtrate was concentrated under a reduced pressure and the residue was triturated with ether to give pure product as white powder (15.6 mg, 59% yield). HRMS(NH$_3$-CI) m/e calcd. for M $(C_{35}H_{47}N_4O_5B)$+H$^+$: 615.3718. Found: 615.3700.

EXAMPLE 14

Synthesis of Ac-(D)Phe-Pro-boroPhe(m-Br)-$C_{10}H_{16}$

Cl-CH[CH$_2$-(m-bromo-phenyl)]BO$_2$-$C_{10}H_{16}$ was prepared making the anion of m-bromobenzyl bromide and coupling it to dichloromethyl boronic acid pinanediol. This intermediate and the corresponding amine were prepared using the procedure described for Example 10. The amine was coupled to Ac-(D)Phe-Pro—OH using the method described in Example 11.

LRMS(NH$_3$-CI) m/e calcd. for M $(C_{34}H_{43}N_3O_5BrB)$+H$^+$: 666.3. Found: 666.2.

EXAMPLE 15

Synthesis of Ac-(D)Phe-Pro-boroArg(CN)-$C_{10}H_{16}$

Ac-(D)Phe-Pro-boroOrn-$C_{10}H_{16}$·HCl (0.15 g, 0.25 mmol), triethylamine (0.035 mL, 0.25 mmol), and diphenyl cyanocarbonimidate (Aldrich, 0.060 g, 0.25 mmol) were heated at a gentle reflux for 5 h in THF and then stirred overnight at room temperature. The sample was diluted with chloroform and washed with water and saturated aqueous NaCl. It was dried over K$_2$CO$_3$ and purified by silica gel chromatgraphy using methanol: chloroform (1:9) as a solvent to yield 80 mg of Ac-(D)Phe-Pro-NH-CH[(CH$_2$)$_3$-NH-C(N-CN)O-Ph]BO$_2$-$C_{10}H_{16}$. LRMS(NH$_3$-CI) m/e calcd. for M $(C_{38}H_{49}N_6O_6B)$+H$^+$: 697.7. Found: 697.

The above product (0.060 g, 0.080 mmol) was dissolved in 0.5 mL of THF and was allowed to react with 1 equivalent of 30% aqueous ammonia for 30 min at room temperature. Four additional equivalent of ammonia were added and the solution was allowed to stir overnight at room temperature. A large excess of ammonia was added and the reaction mixture was allowed to stir 2 days at room temperature. The reaction mixture was diluted with methylene chloride and was washed with water and saturated aqueous NaCl. It was dried over K$_2$CO$_3$ and purified by chromatography on a silica gel column using methanol and chloroform (1:9) as a solvent to yield 15 mg of the desired product. LRMS(NH$_3$-CI) m/e calcd. for M $(C_{32}H_{46}N_7O_5B)$+H$^+$: 619.5. Found: 620.

EXAMPLE 16

Synthesis of Ac-(D)Phe-Pho-boroPhe(p-CN)-$C_{10}H_{16}$

ClCH[CH$_2$C$_6$H$_4$-p-CN]BO$_2$$C_{10}H_{16}$ was prepared by making the anion of p-cyanobenzyl bromide and coupling it to dichloromethyl boronate pinanediol. This intermediate and the corresponding amine were prepared using the procedure described for Example 10. NH$_2$CH[CH$_2$C$_6$H$_4$-p-CN]BO$_2$C$_{10}$H$_{16}$ (Example 78) was coupled to Ac-(D)Phe-Pro—OH using the method described in Example 11.

HRMS (NH$_3$—Cl) m/e calcd. for M $(C_{35}H_{43}N_4O_5B)$+H$^+$: 611. 3405. Found: 611.3408.

EXAMPLE 17

Synthesis of Boc-(D)Phe-Pro-boroPhe(mCN)-$C_{10}H_{16}$

Boc-(D)Phe-Pro-boroPhe(mCN)-$C_{10}H_{16}$ was prepared by reacting Boc-(D)Phe-Pro—OH (0.43 g, 1.2 mmol), H-borophe(mCN)-$C_{10}H_{16}$·HCl (0.42 g, 1.2 mmol), N-methylmorpholine (0.26 mL, 2.4 mmol), hydroxybenzotriazole ·H$_2$O (0.36 g, 2.4 mmol), and dicyclohexylcarbodiimide (0.25 g, 1.2 mmol) in 20 mL of dichloromethane overnight at room temperature. The reaction mixture was filtered and the filtrate was chromatogramed on a 2.5×100 cm column of Sephedex LH-20 in methanol to yield 0.36 g of the desired product.

EXAMPLE 18

Synthesis of H-(D)Phe-Pro-boroPhe(mCN)-$C_{10}H_{16}$·HCl.

Boc-(D)Phe-Pro-boroPhe(mCN)-$C_{10}H_{16}$ (0.21 g) was allowed to react with 2 mL of 4N HCl dioxane for 2 h at room temperature. Solvent was removed by evaporation and the residue was triturated with ether to yield 0.11 g of the desired product as a white solid.

EXAMPLE 19

Synthesis of H-(D)Phe-Pro-boroPhe(mCN)—OH·HCl

H-(D)Phe-Pro-boroPhe(mCN)-$C_{10}H_{16}$·HCl (0.63 g, 1.0 mmol) was allowed to react with 5 equivalents of phenylboronic acid using the procedure described for Example 7 to yield 0.46 g of product.

EXAMPLE 20

Synthesis of N,N Dimethyl-(D)Phe-Pro-boroPhe (mCN)—OH·HCl

H-(D)Phe-Pro-boroPhe(mCN)—OH·HCl(0.20 g, 0.42 mmol), 37% aqueous formaldehyde (0.34 mL, 4.2 mmol) were dissolved in 2 mL of acetonitrile. Sodium cyanoborohydride (0.080 g, 1.3 mmol) was added and after 5 min glacial acetic acid (20 μL) were added. The reaction pH was ~7. After 5 h, additional acetic acid (20 μL) were added and the mixture was stirred for 1 h. The reaction mixture was poured into 20 mL of ethyl acetate and the organic phase was washed with 10 mL of saturated aqueous sodium chloride and dried over anhydrous sodium sulfate. Evaporation of solvent yielded 0.16 g of an oil which was triturated with ether to give a white solid.

EXAMPLE 52

Synthesis of Ac-(D)Phe-Pro-NH-CH[$(CH_2)_3$SC(NH)NHCH$_3$]B(OH)$_2$

The intermediate, Ac-(D)Phe-Pro-NH-CH[$(CH_2)_3$Br]BO$_2$C$_{10}$H$_{16}$, was prepared using the mixed anhydride procedure of example 1. A solution of this bromide (0.35 g, 0.57 mmol) and 1-methyl-2-thiourea (0.077 g, 0.85 mmol) in 10 mL of absolute ethanol was refluxed for 18 hours. After cooling the solvent was removed under vacuum, and the product was separated from excess thiourea employing chromatography (elution: methanol) on Sephadex® LH-20 gel to provide 0.31 g (77%) of the isothiouronium product. This boronic acid ester (0.28 g) was then deprotected as described in example 4 to afford 0.13 g (57%) of the desired product. LRMS (ESI) m/e calcd. for M ($C_{22}H_{34}BN_5O_5S$)+H$^+$: 492. Found: 492. HRMS (NH$_3$-CI) m/e calcd. for ethylene glycol ester M ($C_{24}H_{36}BN_5O_5S$)+H$^+$: 518.260847. Found: 518.261656.

EXAMPLE 54

Synthesis of Ac-(D)Phe-Pro-NH-CH[$(CH_2)_3$NHC(NH)NHCH$_3$]-B(OH)$_2$

A solution of Ac-(D)Phe-Pro-boroOrn-BO$_2$C10H16·HCl [0.50 g, 0.85 mmol, prepared by the procedure of Kettner et al. (1990)], 4-methylaminopyridine (0.21 g, 1.7 mmol), N-methylamino-iminomethanesulfonic acid (0.24 g, 1.7 mmol), and 10 mL of absolute ethanol was refluxed for 18 hours. After cooling the mixture was filtered and the precipitate was washed with chloroform. The combined filtrates were concentrated under vacuum, and the residue was dissolved in 10 mL of chloroform. The chloroform solution was washed with ice-cold 0.1N hydrochloric acid (2×3 mL), ice-cold water (2×3 mL), and brine. The resulting organic solution was then dried over anhydrous magnesium sulfate, filtered, and concentrated. The product was purified employing chromatography (elution: methanol) on Sephadex® LH-20 gel to provide 0.30 g (55%) of the guanidine. This boronic acid ester was then deprotected as described in example 4 to afford 0.14 g (59%) of the desired product. LRMS (NH$_3$-CI) m/e calcd. for ethylene glycol ester M ($C_{24}H_{37}BN_6O_5$)+H$^+$: 501. Found: 501. HRMS (NH$_3$-CI) m/e calcd. for ethylene glycol ester M ($C_{24}H_{37}BN_6O_5$)+H$^+$: 501.299674. Found: 501.300760.

EXAMPLE 102

Synthesis of Boc-(D)Phe-Pro-NH-CH[$(CH_2)_3$-O-NH$_2$]-BO$_{2\text{-}C_{10}H_{16}}$ Part A.

Boc-(D)Phe-Pro-NH-CH[$(CH_2)_3$-O-phthalimide]-BO$_2$-C$_{10}$H$_{16}$ (3.0 g, 4.5 moles), triethylamine (1.9, 13 mmoles), and N-hydroxyphthalimide [0.80 g, 4.9 moles] were dissolved in 10 ml of DMF and heated at 100° C. for 3 hrs. The solution was cooled to room temperature and 200 ml of cold water were added to yield a thick oil. Liquid was removed and the residue was dissolved in absolute ethanol and evaporated. The residue was dissolved in methanol and chromatographed on a column of Sephedex LH$_{20}$™ to yield 1.5 g of the desired product. Anal. Calcd for M ($C_{41}H_{53}N_4O_9B$)+NH4+: 774.4. Found: 774.

Part B.

The phthalimido protected amine (0.30 g, 0.40 mmoles) was dissolved in 3 ml of CH$_2$Cl$_2$ and hydrazine hydrate (0.024 ml, 0.44 moles) and 0.02 ml of methanol were added and the solution was allowed to stir for 24 hrs. Solids were removed by filtration and the filtrate was evaporated. The residue was dissolved in ethyl acetate and solids again were removed by filtration. The solution was acidfided by the additon of 2N HCl in ether to approximately pH 3. (pH measured on a strip of damp pH paper) and the solvent was evaporated. The residue was chromatographed on an LH-20 column to yield the desired product, 0.13 g. Anal. Calcd. for M ($C_{33}H_{51}N_4O_7B$)+H: 627.4. Found: 627.

EXAMPLE 103

Synthesis of Ph-CH$_2$-SO$_2$(D)Phe-Pro-NH-CH[$(CH_2)_3$-O-NH$_2$]-BO$_2$-C$_{10}$H$_{16}$ Part A.

Boc-(D)Phe-Pro-NH-CH[$(CH_2)_3$-O-phthalimide]-BO$_2$-C$_{10}$H$_{16}$ (0.50 g, 0.66 mmoles) was deblocked by stirring for 1 hr with 4 ml of 4N HCl in dioxane. The solvent was evaporated and the residue triturated with ether to give 0.40 g of product as the HCl salt.

Part B.

H-(D)Phe-Pro-NH-CH[$(CH_2)_3$-O-phthalimide]-BO$_2$-C$_{10}$H$_{16}$·HCl (0.20 g, 0.29 mmoles) was dissolved in 4 ml of 50% dioxane: water. Sodium bicarbonate (0.073 g, 0.86 mmoles), and alpha-toluene sulfonyl chloride (0.060 g, 0.32 mmoles) were added. The mixtue was stirred for 5 hr at room temperature and solvent was removed by evaporation. The residue was dissolved in CH$_2$Cl$_2$ (20 mL) and washed with 0.20N HCl (10 mL), 5% NaHCO$_3$ (10 mL), and saturated aqueous NaCl (10 mL). The organic layer was dried over anhydrous MgSO$_4$, filtered, and evaporated to yield 0.18 g of the phthalimido protected aminooxy product. Anal. Calcd. for (M+NH$_4$)$^+$: 828.4. Found: 828.

Part C.

The final product was obtained by removing the phthalimido protecting group with hydrazine as described previously. Anal. Calcd for M ($C_{35}H_{49}N_4O_7BS$)+H: 681.4. Found: 681.

EXAMPLE 104

Synthesis of Boc-(D)Phe-Pro-NH-CH[(CH$_2$)$_3$-O-NH-C(NH)-NH$_2$]-BO$_2$-C$_{10}$H$_{16}$ Boc-(D)Phe-Pro-NH-CH[(CH$_2$)$_3$-O-NH$_2$]-BO$_2$-C$_{10}$H$_{16}$·HCl (0.20 g, 0.30 mmoles) and cyanamide (15 mg, 0.35 mmoles) were dissolved in 5 ml of toluene and heated at 90°–95° C. for 1 hr; additional cyanamide (10 mg, 0.24 mmoles) was added and heating continued for an additional 1 hr. The mixture was cooled to yield a biphasic mixture. The top layer was discarded and the lower phase was triturated with ether and then with petroleum ether to yield a solid (0.15 g). The crude product was purified by chromatography on a LH-20 column to yield 0.12 g. Anal. Calcd. for M (C$_{34}$H$_{53}$N$_6$O$_7$B)+H: 669.4. Found: 669.

EXAMPLE 124

Synthesis Of Ac-(D)Phe-Pro-NH-[CH2-X]BO2-C10H16 (X=4-amino-cyclohexyl)

Part A.

The protected vinylic cyclohexanone (Scheme 12, 35) was prepared by first dissolving potassium t-butoxide (11 g, 0.10 moles) and methyltriphenyl phosphonium iodide (39 g, 0.10 moles) in 500 ml of anhydrous toluene, heating to reflux, and slowly adding cyclohexadione monoethylene ketal (15 g, 0.10 moles) as a toluene solution. The reaction mixture was refluxed for 3 hrs and then cooled to room temperature. It was poured over ice and the product was extracted into ether. The organic solution was washed with saturated aqueous NaCl (1×250 mL) and dried over anhydrous sodium sulfate. The organic solution was filtered and concentrated and applied to a silica gel column equilibrated with ethyl acetate: hexane (1:5) to yield the desired product, 12 g, as a colorless oil.

Part B.

The product of Part A (8.5 g, 55 moles) was dissolved in 5 ml of anhydrous THF and added dropwise to 50 mmoles of diisopinocamphyl borane in 18 ml of THF, at 0° C. The diisopinocamphyl borane was prepared prior to the reaction by a published procedure (Brown et al. J. Org. Chem 47, 5065, 1982). After stirring for 1 hr at 0° C., anhydrous acetaldehyde (8.8 g, 200 mmoles) was added dropwise and the reaction stirred for 36 hr at room temperature. The solvent and alpha pinene were removed by evaporation and pinanediol (8.5 g, 50 mmoles) dissolved in 40 ml of THF was added. Solvent was evaporated after 3 hrs to yield the desired crude product which was purified by chromatography on silica gel using ethyl acetate: hexane (1:5) to give the purified product in a yield of 96%.

Part C.

The product of Part B (7.9 g, 24 mmoles) and methylene chloride (3.6 g, 42 mmoles), were dissolved in 200 ml of anhydrous THF and cooled to -78° C. Lithium diisopropylamine (38 mmoles), prepared by treating diisopropylamine (3.8 g, 38 mmoles) with 25 mL of 1.5M n-butyl lithium in hexane (38 mmoles) in 20 ml of THF, was added dropwise. Anhydrous ZnCl$_2$ (6.8 g, 50 mmoles) dissolved in 50 ml of THF was added and the reaction mixture was allowed to stir overnight at room temperature. Ether was added and the insoluble material removed. The organic phase was washed with water and dried over anhydrous MgSO$_4$. The crude product was purified by silica gel chromatrography using ethyl acetate: hexane to yield 8 g.

Part D.

The product of Part C(1.3 g, 3.4 mmoles) was dissolved in 25 ml of THF and cooled to -78° C. This solution was added at -78° C. to a solution containing the lithium salt of hexamethyldisilazane, which had been prepared by treating hexamethyldisilazane (2.9 g, 18 mmoles) in 10 ml of THF with n-butyl lithium (1.5N in hexane, 12 ml, 18 mmoles), at -78° C. followed by warming to room temperature. After completion of addition, the mixture was warmed to room temperature and stirred overnight. Solvent was evaporated and the residue dissolved in 100 ml of ether and 100 ml of pentane to yield a precipitate of LiCl. This solid material was filtered and the mother liquor concentrated. The product, approximately 9.0 g (18 mmoles), was dissolved in 40 ml of ether and was treated with 55 ml of anhydrous 1N HCl in ether at -78° C. The mixture was allowed to warm to room temperature and stirred overnight. Solvent was evaporated to yield the desired product, 7.0 g, as a foam.

Part E.

Ac-(D)Phe-Pro—OH (3.1 g, 10 mmoles) in 50 ml of THF, N-methylmorpholine (1.1 ml, 10 mmoles) and isobutylchloroformate (1.3 ml, 10 mmoles) were mixed at -20° C. After 5 min, the product of Part D (4.0 g, 10 mmoles) was added at -20° C. as a 75 ml solution in THF. Triethylamine (1.4 ml, 10 mmoles) was added and the mixture was stirred for 1 hr at -20° C. and 3 hrs at room temperature. Solvent was evaporated and the residue was chromatogramed on LH-20 using methanol as a solvent. Additional purification was achieved by chromatography on silica gel using a stepwise gradient from 1% methanol to 10% methanol in chloroform to yield ~4.5 g of the desired product.

Part F.

The product of Part E (0.10 g, 0.15 mmoles) was converted to the ketone by dissolving it in 5 ml of dioxane and adding it to 5 ml of an aqueous suspension of BioRad AG50-X8 resin (H+ form). The mixture was stirred overnight, filtered, and evaporated. The residue was chromatogramed on silica gel using chloroform: methanol (9:1) as a solvent to yield 75 mg of the desired product. Anal. Calcd for M (C$_{34}$H$_{52}$N$_4$O$_6$B)+NH$_4^+$: 623.4. Found: 623.

Part G.

The ketone, Ac-(D)Phe-Pro-NH[CH$_2$-X]BO$_2$-C$_{10}$H$_{16}$ (X=4-cyclohexanone) (0.10 g, 0.17 mmoles), ammonium acetate (0.13 g, 1.7 mmoles) and sodium cyanoborohydride (10 mg, 0.17 mmoles) were dissolved in 5 ml of methanol and stirred for 48 hrs. Anhydrous HCl (1 equ) was added and the reaction mixture was evaporated. The residue was chromatographed on a column of LH-20 using methanol as a solvent to yield 70 mg of the desired product. Anal.Calcd. for M (C$_{34}$H$_{51}$N$_4$O$_5$B)+H: 607.4. Found: 607.

EXAMPLE 125

Synthesis of Boc-(D)Phe-PrO-NH-CH[CH$_2$-X]-BO$_2$-C$_{10}$H$_{16}$ (X=4-amino-cyclohexyl)

Part A.

Following the procedure of the previous example, Boc-(D)Phe-Pro—OH (2.9 g, 8.0 mmoles) was coupled to the alpha-aminoboronic acid to yield 3.6 g. Anal Calcd. for M (C$_{38}$H$_{56}$N$_3$O$_8$B)+H: 694.5. Found: 694.4.

Part B.

The peptide ketal (Scheme 12, 43) (4.0 g, 5.7 mmoles) was converted to the ketone 44 in a yield of 2.5 g. Anal. Calcd for M (C$_{36}$H$_{52}$N$_3$O$_7$B)+H: 664.5. Found: 664.4.

Part C.

Reductive amination of 44 (1.0 g, 1.5 mmoles) yielded 0.78 g of the desired product. Anal. Calcd. for M (C$_{37}$H$_{57}$N$_4$O$_6$B)+H: 665.5. Found: 665.4.

EXAMPLE 126

Synthesis of Boc-(D)Phe-Pro-NH-CH[X]BO$_2$-C$_{10}$H$_{16}$ (X=4-cyclohexylamine)

Part A.

Cyclo-3-hexenone ketal was prepared by the procedure described by Laronze et al Synthetic Communications 21., 881, 1991. Cyclo-2-hexenone (20 g, 0.21 mol), ethylene glycol (48 g, 0.78 mol), and p-toluene sulfonic acid (3.0 g, 0.016 mol) were dissolved in 750 ml of toluene in a round bottom flask equipped with a Dean Stark trap and a reflux condenser. After refluxing overnight and removing water, the flask was cooled to room temperature and the toluene solution was washed with saturated aqueous NaCl (1×500 mL). The aqueous layer was washed with methylene chloride (1×250 mL) and the combined organic phases were evaporated. The crude product was purified by chromatography on a silica gel column using ethyl acetate: hexane (1:7) to yield 13 g.

Part B.

The product of Part A (1.8 g, 13 mmoles) was hydroborated and converted to the pinanediol ester using the procedure described in earlier examples. Chromatography on silica gel using ethyl acetate: hexane (1:7) and a 1:40 ratio of crude product: silica gel gave a mixture of 1,3- and 1,4-disubstituted boronic acid ester (Scheme 13, 48) in a yield of 3.7 g. Anal. Calcd. for M (C$_{18}$H$_{29}$O$_4$B)+H: 321.3. Found: 321.1.

Part C.

Homologation of the product of Part B (1.2 g, 3.2 mmoles) and purification by silica gel chromatography gave 1.3 g of a mixture of 1,3 and 1,4-disubstituted α-chloro boronic acid isomers. Anal. Calcd. for M (C$_{19}$H$_{30}$O$_4$ClB)+H: 369.3. Found: 369.1.

Part D.

The α-chloro boronic acid (Scheme 9, XI) (1.2 g, 3.3 mmoles) was converted to 1.3 g of the ketal protected amine hydrochloride.

Part E.

Boc-(D)Phe-Pro—OH (1.3 g, 3.3 mmoles) was coupled to 1.2 g of the product of Part D. Following purification using silica gel chromatography with chloroform:methanol (1:9), 0.60 g of the desired product was obtained. Anal. Calcd. for M (C$_{38}$H$_{56}$N$_3$O$_8$B)+H: 694.5. Found: 694.4.

Part F.

The side chain ketone was generated in almost quantitive yield following the procedure outlined above. Anal. Calcd. for M (C$_{36}$H$_{52}$N$_3$O$_7$B)+H: 650.5. Found: 650.4

Part G.

The final product was obtained by reductive amination of the product of Part F (0.20 g, 0.31 mmoles). The desired product was obtained in a yield of 0.15 g. Anal. Calcd. for M (C$_{36}$H$_{55}$N$_4$O$_6$B)+H: 651.5. Found: 651.2.

EXAMPLE 127

Synthesis of Boc-(D)Phe-Pro-NH-CH[CH$_2$-X]BO$_2$-C$_{10}$H$_{16}$ (X=4-hydoxy-cyclohexyl)

Boc-(D)-Phe-Pro-NH-CH[CH$_2$(4-oxocyclohexyl)]BO$_2$-C$_{10}$H$_{16}$ (0.50 g, 0.75 mmoles) was dissolved in 2 ml of anhydrous methanol and sodium borohydride (50 mg, 1.3 mmoles) was added. After 30 min, additional NaBH$_4$ (30 mg) was added. After 30 min, the reaction mixture was concentrated, water was added, and the reaction mixture was concentrated a second time. Silica gel chromatography of the residue yielded 200 mg of the desired product. Anal. Calcd. for M (C$_{37}$H$_{56}$O$_7$N$_3$B)+H: 666.5. Found: 666.4.

EXAMPLE 128

Synthesis of Boc-(D)Phe-Pro-NH-CH[CH$_2$X]BO$_2$-C$_{10}$H$_{16}$ (X=4-guanidino-cyclohexyl)

Part A.

Boc-(D)Phe-Pro-NH-CH[CH$_2$-(4-NH$_2$-cyclohexyl)]BO$_2$-C$_{10}$H$_{16}$ (0.78 g, 1.1 mmoles), N,N-dimethylaminopyridine (0.14 g, 1.1 mmoles) and Z—N=C(S—Et)—NH—Z (0.43, 1.1 moles) were suspended in 7 ml of isopropyl alcohol and heated to 50° C. to give a complete solution. After 5 hrs., the solvent was evaporated and the residue dissolved in 50 ml of ethyl acetate and washed with 5% NaCO$_3$ (50 mL), 0.20N HCl (50 mL), and saturated aqueous NaCl (50 mL). The product was dried over anhydrous Na$_2$SO$_4$, filtered, and evaporated. The residue was purified by silica gel chromatography using 3% methanol in ethyl acetate as a solvent. The bis-carbobenzoxy protected guanidine was isolated as a white foam, 0.95 g. Anal. Calcd. for M (C$_{54}$H$_{71}$N$_6$O$_{10}$B)+H: 975.6. Found: 975.2.

Part B.

The product of Part A (0.79 g, 0.81 mmoles) was dissolved in 20 ml of methanol and hydrogenated in a Parr apparatus at an initial pressure of 50 psi in the presence of benzene sulfonic acid (0.13 g, 0.81 mmoles) and 0.50 g of 10% Pd/C. After 4 hrs, the reaction mixture was filtered. The filtrate was concentrated and applied to a column of LH-20 in methanol. The desired product was obtained in a yield of 0.45 g. Anal. Calcd. for M (C$_{38}$H$_{59}$N$_6$O$_6$B)+H: 707.5. Found: 707.4.

EXAMPLE 129

Synthesis of Boc-(D)Phe-Pro-(R)Phe(mCN)-OMe

Part A.

Z-NH-CH[P(OMe)$_2$]COOMe (5.0 g, 15 mmoles) was dissolved in 50 ml of methanol and hydrogenated in a Parr apparatus (inital pressure 40 psi) in the presence of 0.40 g of 10% Pd/C. After one equivalent of hydrogen was consumed, the catalyst was removed by filtration and the filtrate was evaporated to give the free amine.

Part B.

NH$_2$-CH[P(OMe)$_2$]COOMe (2.5 g, 13 mmoles), Boc-(D) Phe-Pro—OH (4.6 g, 13 mmoles), N-methylmorpholine (1.4 ml, 13 mmoles), and hydroxybenzotriazole ·H$_2$O (3.9 g, 25 mmoles) were dissolved in 150 ml of methylene chloride and dicyclohexylcarbodiimide (2.6 g, 13 mmoles) was added. The mixture was allowed to stir overnight at room temperture. Insoluble material was removed by filtration, and the filtrate was evaporated. The residue was dissolved in ethyl acetate and washed with 5% NaHCO$_3$ (150 mL), 0.20N HCl (150 mL), and saturated aqueous NaCl (150 mL). After drying over anhydrous MgSO$_4$ and evaporating, a white solid (5.7 g) was obtained. Anal. Calcd. for M (C$_{24}$H$_{36}$N$_3$O$_9$P)+H: 542.227. Found: 542.225.

Part C.

Boc-(D)Phe-Pro-NH-CH[P(OMe)2]COOMe (1.4 g, 2.6 mmoles) was dissolved in 7 ml of THF and was added dropwise to a −78° C. solution of lithium diisopropyamine (prepared by dissolving diisopropylamine (0.41 ml, 2.9 mmoles) in 5 ml of THF and adding 1.6N n-butyl lithium in hexane (1.7 ml, 2.6 mmoles at 0° C.). During the addition, a precipitate formed which was dissolved by warming the reaction mixture to 0° C. for 5 min and recooling to −78° C. m-Cyanobenzaldehyde (0.35 g, 2.6 mmoles) was dissolved in 3 ml of THF and added dropwise to the reaction. The reaction was allowed to warm to room temperature and stir for approximately 3 hrs. The solvent was evaporated, and the residue dissolved in 50 ml of ethyl acetate and washed with saturated aqueous NaCl (50 mL) and was dried over anhydrous $MgSO_4$. After evaporation of solvent, the α,β-unsaturated product 1.4 g, was obtained as a foam.

Part D.

The product of Part C was hydrogenated in the presence of (R,R)DuPHOS catalyst according to the procedure of Burke et al. J. Am. Chem. Soc., 115, 10125, 1993. The desired product with the α-carbon in the R configuration was obtained. Anal. Calcd. for M ($C_{30}H_{36}N_4O_6$)+H: 549.271. Found: 549.271.

EXAMPLE 130

Synthesis of Boc-(D)Phe-Pro-(S)Phe(mCN)-OMe

This was prepared according to the procedure of the above example except that the hydrogenation was done using (S,S)DuPHOS to give the desired product. Anal. Calcd. for M (C30H36N4O6)+H: 549.271. Found: 549.271.

EXAMPLE 131

Synthesis of Boc-Pro-(S)PheCmCN)-OMe

Part A.

Boc-Pro—OH was coupled to $NH_2$-CH[P(O)(OMe)$_2$]COOMe by the above procedures to give Boc Pro-NH-CH[P(O)(OMe)$_2$]COOMe. Anal Calcd. for M ($C_{15}H_{27}N_2O_8P$)+$NH_4$+: 412.2. Found: 412.

Part B.

The product of Part A was coupled to m-cyanobenzaldehyde to give the α,β-unsaturated dipeptide analog. Anal. Calcd. for M ($C_{21}H_{25}N_3O_5$)+$NH_4$+: 417.2. Found: 417.

Part C.

The product of Part B was reduced using (S,S)DuPHOS catalyst to yield Boc-(L)Pro-(L)Phe(mCN)-OMe. Anal. Calcd for M ($C_{21}H_{27}N_3O_5$)+$NH_4$+: 419. Found: 419.

EXAMPLE 132

Synthesis of Boc-Pro-Phe(mCN)—OH

Boc-Pro-Phe(mCN)-OMe (3.8 g, 9.5 moles) was dissolved in 16 ml of 50% dioxane: water. NaOH (0.42 g, 10 mmoles) was added and the solution was stirred overnight at room temperature. Dioxane was removed by evaporation, and the solution was diluted to 100 ml with water. After acidifying to pH <2 with HCl, a precipitate was obtained. It was isolated and then recrystallized from ethanol: water to yield 2.3 g (m.p. 183°–185° C.). Anal. Calcd for M ($C_{20}H_{25}N_3O_5$+H 388.2. Found: 388.1.

EXAMPLE 133

Synthesis of Boc-Pro-Phe(mCN)-N(Me)-OMe

Boc-Pro-Phe(mCN)—OH (2.1 g, 5.4 mmoles) and N-methylmorpholine (1.3 ml, 12 mmoles) were dissolved in 35 ml of methylene chloride and cooled to –5° C. Isobutylchloroformate (0.70 ml, 5.4 mmoles) was added, and the solution was stirred for 15 min at –5° C. N-Methyl-N-methoxyamine (0.87 g, 9.0 mmoles) was added and the mixture was stirred 45 min at –5° C. and 3 hrs at room temperature. Water (35 mL) was added and the phases were separated. The aqueous phase was washed with methylene chloride (1×50 mL) and the combined organic phases were dried over $MgSO_4$ and evaporated. The product was purified by chromatography using ethyl acetate:hexane (2:1). The product was recrystallized from ethyl acetate:hexane to yield 2.0 g (mp 130°–132° C.). Anal. Calcd for M($C_{22}H_{30}N_4O_5$)+$NH_4$+: 448.3. Found: 448.

EXAMPLE 134

Synthesis of Boc-Pro-Phe(mCN)-C(OEt)=$CH_2$

Ethyl vinyl ether (1.2 ml, 12 mmoles) was dissolved in 25 ml of THF and cooled to –78° C. t-Butyl lithium (6.8 ml, 12 mmoles) was added and the reaction was warmed to 0° C. and stirred for 30 min. Magnesium bromide etherate (12 mmoles) was added, and the mixture was stirred for an additional 30 min. Boc-Pro-Phe(mCN)-N(Me)-OMe (1.0 g, 2.3 mmoles), dissolved in 5 ml of THF, was added to the reaction mixture. The reaction was warmed to room temperature and stirred for 3 hrs. Saturated aqueous $NH_4Cl$ (10 ml) was added and solvent was evaporated. The residue was dissolved in ethyl acetate (50 mL) and washed with water (50 mL) and saturated aqueous NaCl (50 mL). The organic phase was dried over $MgSO_4$ and evaporated. The product was purified by silica gel chromatography using ethyl acetate:hexane (2:1). The desired product (220 mg) was obtained. Anal. Calcd for M ($C_{24}H_{31}N_3O_5$)+$NH_4$+: 459. Found: 459.

EXAMPLE 135

Synthesis of H-(D)Phe-Pro-boroPhe(mCOOMe)-$C_{10}H_{16}$·HCl

Boc-(D)Phe-Pro-boroPhe(mCN)-$C_{10}H_{16}$ (0.50 g, 0.75 mmoles) was dissolved in 20 ml of anhydrous methanol and cooled to 0° C. Anhydrous HCl was slowly bubbled through the solution for 2 hrs. The reaction was allowed to stand at 4° C. overnight. Ether was added to form a solid. Dioxane (5 ml) and water (25 ml) were added and the mixture was stirred for ~7 hrs at room temperature. The solvent was evaporated and the residue triturated with ether to yield the desired product as a mixture of the free boronic acid an pinanediol ester (0.28 g). This material was treated with 0.19 g of pinanediol in 3 ml of methanol for 5 min and was applied to a column of LH-20 in methanol. The desired product was obtained in a yield of 0.16 g. Anal. Calcd. for M ($C_{34}H_{44}N_3O_6B$)+H: 602.340. Found: 602.339.

EXAMPLE 136

Hydrocinnamoyl-ProboroGly[($CH_2$)$_4$-NH-Acetyl] $C_{10}H_{16}$

To a stirred solution of Hydrocinnamoyl-ProboroLys (1.0 g, 1.8 mmol), $Et_3N$ (501 μL, 3.6 mmol) in THF (50 mL) was added acetylchloride at 0° C. under an $N_2$ atmosphere. After stirring for 3 h at r.t., the mixture was diluted with ethyl acetate (50 mL) and washed with $H_2O$ (1×100 mL), HCl (1N, 1×100 mL), $NaHCO_3$ (sat'd, 1×100 mL), and NaCl (sat'd, 1 x 100 mL). The organic layer was then dried over $Na_2SO_4$ and concentrated in vacuo to afford the desired product (991 mg, 1.8 mmol).(M+H)+ 552.4 HRMS for C31 H47N3O5B calc. 552.360877; found 552.360898.

The examples shown in Table 1 can be prepared by the schemes and procedures described above using the appropriate starting materials.

TABLE 1

| EX # | Compound | Ms Method | LRMS CALC'D | LRMS FOUND |
|---|---|---|---|---|
| 1 | Ac—(D)Phe—Pro—NH—CH[(CH$_2$)$_4$CN]BO$_2$C$_{10}$H$_{16}$ | NH$_3$/CI (M + NH$_4$) | 594.4 | 594 |
| 2 | Ac—(D)Phe—Pro—NH—CH[(CH$_2$)$_4$—C(NH)NH$_2$]BO$_2$C$_{10}$H$_{16}$.BSA | NH$_3$/CI (M + H) | 594.4 | 594 |
| 3 | Ac—(D)Phe—Pro—boroOrn(CH=NH)]—C$_{10}$H$_{16}$.HCl | NH$_3$/CI (M + H) | 580.4 | 580 |
| 4 | Ac—(D)Phe—Pro—boroOrn(CH=NH)]—OH.HCl | NH$_3$/CI pinacol ester + H | 528.3 | 528 |
| 5 | Boc—Pro—boroOrn(CH=NH)—C$_{10}$H$_{16}$.HCl | NH$_3$/CI (M + H) | 491.5 | 491 |
| 6 | Boc—(D)Phe—Pro—boroOrn(CH=NH)]—C$_{10}$H$_{16}$.0.5 HCl.0.5 BSA | NH$_3$/CI (M + H) | 638.4 | 638 |
| 7 | Boc—(D)Phe—Pro—boroOrn(CH=NH)]—OH.0.6 HCl.0.4 BSA | NH$_3$/CI pinacol ester + H | 586.4 | 586 |
| 8 | H—(D)Phe—Pro—boroOrn(CH=NH)]—C$_{10}$H$_{16}$.0.5 HCl.0.5 BSA | NH$_3$/CI (M + H) | 538.4 | 538 |
| 9 | H—(D)Phe—Pro—boroOrn(CH=NH)]—OH.0.65 HCl.0.35 BSA | NH$_3$/CI pinacol ester + H | 486.3 | 486 |
| 10 | H—boroPhe(mCN)—C$_{10}$H$_{16}$.HCl | | | |
| 11 | Ac—(D)Phe—Pro—boroPhe—(m-CN)—C$_{10}$H$_{16}$ | NH$_3$/CI (M + H) | 611.3 | 611 |
| 12 | Ac—(D)Phe—Pro—boroPhe—(m-C(NH)NH$_2$)—C$_{10}$H$_{16}$.BSA | NH$_3$/CI (M + H) | 628.4 | 628 |
| 13 | Ac—(D)Phe—Pro—boroPhe—(m-CH2NH$_2$)—C$_{10}$H$_{16}$.HCl | NH$_3$/CI (M + H) | 615.4 | 615 |
| 14 | Ac—(D)Phe—Pro—boroPhe(m-Br)—C$_{10}$H$_{16}$ | NH$_3$/CI (M + NH$_4$) | 683.4 | 683 |
| 15 | Ac—(D)Phe—Pro—boroArg(CN)—C$_{10}$H$_{16}$.HCl | NH$_3$/CI (M + H) | 619.5 | 620 |
| 16 | Ac—(D)Phe—Pro—boroPhe(p-CN)—C$_{10}$H$_{16}$ | NH$_3$/CI (M + NH$_4$) | 628.4 | 628 |
| 17 | Boc—(D)Phe—Pro—boroPhe(m-CN)—C$_{10}$H$_{16}$ | NH$_3$/CI (M + NH4) | 686.4 | 686 |
| 18 | H—(D)Phe—Pro—boroPhe(m-CN)—C$_{10}$H$_{16}$.HCl | NH$_3$/CI (M + H) | 569.3 | 569 |
| 19 | H—(D)Phe—Pro—boroPhe(m-CN)—OH.HCl | NH$_3$/CI EG ester + H | 461.2 | 461 |
| 20 | N,N-(CH3)$_2$—(D)Phe—Pro—boroPhe—(m-CN)—OH.HCl (ISOMER I) | NH$_3$/CI EG ester + H | 489.3 | 489 |
| 21 | Ac—(D)Phe—Pro—boroPhe(p-CH$_2$NH$_2$)—C$_{10}$H$_{16}$.BSA | NH$_3$/CI (M + H) | 615.4 | 615 |
| 22 | Ac—(D)Phe—Pro—boroPhe(p-C(NH)NH$_2$)—C$_{10}$H$_{16}$.BSA | FAB (M + H) | 628.37 | 628.44 |
| 23 | Ac—(D)Phe—Pro—boroPhe—(m-CN)—OH.HCl | NH$_3$/CI EG ester + NH$_4$ | 520.3 | 520 |
| 24 | Ms—(D)Phe—Pro—boroPhe(m-CN)—OH.HCl | NH$_3$/CI EG ester + NH$_4$ | 556.2 | 556 |
| 25 | N—CH$_3$—(D)Phe—Pro—boroPhe(m-CN)—C$_{10}$H$_{16}$.HCl | NH$_3$/CI (M + H) | 583.4 | 583.3 |
| 26 | H—Pro—boroPhe(m-CN)—C$_{10}$H$_{16}$.HCl | NH$_3$/CI (M + H) | 422.3 | 422 |
| 27 | Boc—(D)Thiazolylalanine-Pro—boroPhe(m-CN)—C$_{10}$H$_{16}$ | NH$_3$/CI (M + H) | 676.4 | 676.4 |
| 28 | Boc—(D)3-Pyridylalanine-Pro—boroPhe—(m-CN)-C$_{10}$H$_{16}$ | NH$_3$/CI (M + H) | 670.4 | 670.4 |
| 29 | H—(D)Thiazolylalanine-Pro—boroPhe(m-CN)—C$_{10}$H$_{16}$.HCl | NH$_3$/CI (M + H) | 576.3 | 576 |
| 30 | H—(D)3-Pyridylalanine-Pro—boroPhe(m-CN)—C$_{10}$H$_{16}$.HCl | NH$_3$/CI (M + H) | 570.3 | 570 |
| 31 | Ms—(D)Thiazolylalanine-Pro—boroPhe(m-CN)—C$_{10}$H$_{16}$ | NH$_3$/CI (M + H) | 654.3 | 654 |
| 32 | Ms—(D)3-Pyridylalanine-Pro—boroPhe(m-CN)—C$_{10}$H$_{16}$ | NH$_3$/CI (M + H) | 648.3 | 648 |
| 33 | N—Boc—N—CH$_3$—(D)Phe—Pro—boroPhe(m-CN)—C$_{10}$H$_{16}$ | NH$_3$/CI (M + NH$_4$) | 700.4 | 700 |

TABLE 1-continued

| EX # | Compound | Ms Method | LRMS CALC'D | LRMS FOUND |
|---|---|---|---|---|
| 34 | Boc—(D)2-Pyridylalanine-Pro—boroPhe(m-CN)—$C_{10}H_{16}$ | $NH_3$/CI (M + H) | 670.4 | 670 |
| 35 | Ac—Pro—boroPhe(m-CN)—$C_{10}H_{16}$ | $NH_3$/CI (M + $NH_4$) | 481.3 | 481 |
| 36 | Boc—(D)2-Thienylalanine-Pro—boroPhe(m-CN)—$C_{10}H_{16}$ | $NH_3$/CI (M + $NH_4$) | 692.4 | 692 |
| 37 | H—(D)2-Pyridylalanine-Pro—boroPhe(m-CN)—$C_{10}H_{16}$.HCl | $NH_3$/CI (M + H) | 570.3 | 570 |
| 38 | H—(D)2-Thienylalanine-Pro—boroPhe(m-CN)—$C_{10}H_{16}$.HCl | $NH_3$/CI (M + H) | 575.3 | 575 |
| 39 | Ms—(D)2-Pyridylalanine-Pro—boroPhe(m-CN)—$C_{10}H_{16}$ | $NH_3$/CI (M + H) | 648.3 | 648 |
| 40 | Ms—(D)2-Thienylalanine-Pro—boroPhe(m-CN)—$C_{10}H_{16}$ | $NH_3$/CI (M + $NH_4$) | 670.3 | 670 |
| 41 | (2-Pyrimidylthio)acetyl-Pro—boroPhe(m-CN)—$C_{10}H_{16}$ | $NH_3$/CI (M + H) | 574.3 | 574 |
| 42 | trans-3-(3-pyridyl)acryl-Pro—boroPhe(m-CN)—$C_{10}H_{16}$ | $NH_3$/CI (M + H) | 553.3 | 553 |
| 43 | (4-Pyridylthio)acetyl-Pro—boroPhe(m-CN)—$C_{10}H_{16}$ | $NH_3$/CI (M + H) | 573.3 | 573 |
| 44 | Succinyl-(D)Phe—Pro—boroPhe(m-CN)—OH | $NH_3$/CI EG ester + $NH_4$ | 578.3 | 578 |
| 45 | 3-Pyridylpropionyl-Pro—boroPhe(m-CN)—$C_{10}H_{16}$ | $NH_3$/CI (M + H) | 553.3 | 555 |
| 46 | Boc—(D)Phe—Aze—boroPhe(m-CN)—$C_{10}H_{16}$ | $NH_3$/CI (M + $NH_4$) | 672.4 | 672 |
| 47 | H—(D)Phe—Aze—boroPhe(m-CN)—$C_{10}H_{16}$.HCl | $NH_3$/CI (M + H) | 555.3 | 555 |
| 48 | Hydrocinnamoyl-Pro—boroOrn(CH=NH)]OH.BSA | FAB EG ester + H | 445.5 | 445 |
| 49 | Hydrocinnamoyl-Pro—boroIrg($CH_2CH=CH_2$)—OH.HBr | ESI (M + H) | 461 | 461 |
| 50 | Hydrocinnamoyl-Pro—boroIrg($CH_3$)—OH.HBr | ESI (M + H) | 435 | 435 |
| 51 | Cbz—(D)Phe—Pro—boroIrg($CH_3$)—$C_{10}H_{16}$.HBr | $NH_3$/CI (M + H) | 718 | 718 |
| 52 | Ac—(D)Phe—Pro—boroIrg($CH_3$)—OH.HBr | ESI (M + H) | 492 | 492 |
| 53 | Hydrocinnamoyl-Pro—boroIrg($CH_2CH_3$)—OH.HBr | ESI (M + H) | 449 | 449 |
| 54 | Ac—(D)Phe—Pro—boroArg($CH_3$)—OH.HCl | $NH_3$/CI EG ester + H | 501 | 501 |
| 55 | Hydrocinnamoyl-Pro—boroArg($CH_3$)—OH.HCl | ESI (M + H) | 418 | 418 |
| 56 | Ms—(D)Phe—Pro—boroArg($CH_3$)—OH.HCl | ESI (M + H) | 511 | 511 |
| 57 | Ms—(D)Phe—Pro—boroOrn(CH=NH)—OH.HCl | ESI (M + H) | 482 | 482 |
| 58 | $PhSO_2$—(D)Phe—Pro—boroArg($CH_3$)—OH.HCl | ESI (M + H) | 573 | 573 |
| 59 | $PhSO_2$—(D)Phe—Pro—boroOrn(CH=NH)—OH.HCl | ESI (M + H) | 544 | 544 |
| 60 | Ms—(D)Phe(4-fluoro)-Pro—boroOrn(CH=NH)—OH.HCl | ESI (M + H) | 500 | 500 |
| 61 | $PhCH_2SO_2$—(D)Phe—Pro—boroArg($CH_3$)—OH.HCl | ESI (M + H) | 587 | 587 |
| 62 | $PhCH_2SO_2$—(D)Phe—Pro—boroOrn(CH=NH)—OH.HCl | ESI (M + H) | 558 | 558 |
| 63 | $CH_3CH_2CH_2SO_2$—(D)Phe—Pro—boroOrn(CH=NH)—OH.HCl | ESI (M + H) | 510 | 510 |
| 64 | $CH_3CH_2CH_2SO_2$—(D)Phe—Pro—boroArg($CH_3$)—OH.HCl | ESI (M + H) | 539 | 539 |
| 65 | $CH_3(CH_2)_3SO_2$—(D)Phe—Pro—boroArg($CH_3$)—OH.HCl | ESI (M + H) | 553 | 553 |
| 66 | $CH_3(CH_2)_3SO_2$—(D)Phe—Pro—boroOrn(CH=NH)—OH.HCl | ESI (M + H) | 524 | 524 |
| 67 | Ac—(D)Phe—Sar—boroOrn(CH=NH)—OH.HCl | $NH_3$/CI EG ester + H | 446.3 | 446.3 |
| 68 | Ms—(D)Phe—Sar—boroOrn(CH=NH)—OH.HCl | $NH_3$/CI EG ester + H | 482.2 | 482.2 |

TABLE 1-continued

| EX # | Compound | Ms Method | LRMS CALC'D | LRMS FOUND |
|---|---|---|---|---|
| 69 | Phenethyl—SO₂—(D)Phe—Sar—boroOrn(CH=NH)—OH.HCl | NH₃/CI EG ester + H | 572.27 | 572.27 |
| 70 | Boc—(D)Phe—Sar—boroOrn(CH=NH)—OH.HCl | NH₃/CI EG ester + H | 504.3 | 504.3 |
| 71 | N-alpha-[boroOrn(CH=NH)—OH]-(2-trans benzylcarboxamido)-cyclopentane-1-carboxamide.HCl | NH₃/CI EG ester + H | 415.25 | 415.25 |
| 72 | H—(D)Phe—Sar—boroOrn(CH=NH)—C₁₀H₁₆.2HCl | ESI (M + H) | 512.3 | 512.3 |
| 73 | Boc—(D)Phe—Sar—boroPhe(m-CN)—C₁₀H₁₆ | ESI (M + H) | 643.36 | 643.36 |
| 74 | Boc—(D)Phe—Aze—boroOrn(CH=NH)—OH.HCl | NH₃/CI EG ester + H | 546.3 | 546.3 |
| 75 | H—(D)Phe—Sar—boroPhe(m-CN)—C₁₀H₁₆.2HCl | ESI (M + H) | 543.3 | 543.3 |
| 76 | 4-(Phenyl)benzoyl-boroOrn(CH=NH)—C₁₀H₁₆.HCl | ESI (M + H) | 474.3 | 474.3 |
| 77 | Z—(D)Phe—Pro—boroOrn(CH=NH)—OH.HCl | NH₃/CI pinacol ester + H | 620.58 | 620.36 |
| 78 | H—boroPhe—(p-CN)—C₁₀H₁₆.HCl | | | |
| 79 | Boc—(D)Phe—Pro—N(CH₃)CH[(CH₂)₃NHC(NH)H]—B(OH)₂ | | | |
| 80 | Boc—(D)Phe—Pro—N(Phenyl)CH[(CH₂)₃NHC(NH)H]—B(OH)₂ | | | |
| 81 | Boc—(D)Phe—Pro—N(benzyl)CH[(CH₂)₃NHC(NH)H]—B(OH)₂ | | | |
| 82 | Boc—(D)Phe—Pro—N(CH₃)CH[(CH₂)₃NHC(NH)H]—B(OMe)₂ | | | |
| 83 | Boc—(D)Phe—Pro—N(CH₃)CH[(CH₂)₃NHC(NH)H]—B[N(Me)]₂ | | | |
| 84 | Boc—(D)Phe—Pro—N(CH₃)CH[(CH₂)₃NHC(NH)H]—B(F)₂ | | | |
| 85 | FMoc—(D)Phe—Pro—NHCH[(CH₂)₃NHC(NH)H]—B(OC₁₀H₁₆)₂ | | | |
| 86 | Ac—(D)cyclohexylalanyl-Pro—NHCH[(CH₂)₃NHC(NH)H]—B(OC₁₀H₁₆)₂ | | | |
| 87 | Ac—(D)Phe—Gly—NHCH[(CH₂)₃NHC(NH)H]—B(OC₁₀H₁₆)₂ | | | |
| 88 | Ac—(D)Phe—Pro—NHCH[(CH₂)₃NHC(NOH)NH₂]—B(OC₁₀H₁₆)₂ | | | |
| 91 | Ac—(D)Phe—Pro—BoroPhe(p-Br)—C₁₀H₁₆ | | | |
| 92 | Ac—(D)Phe—Pro—boroPhe(p-NH₂)—C₁₀H₁₆ | | | |
| 93 | Ac—(D)Phe—Pro—boroPhe(p-NHC(NH)NH₂)—C₁₀H₁₆ | | | |
| 95 | Ac—(D)Phe—Pro—boroPhe(p-CH₂NHC(NH)NH₂)—C₁₀H₁₆ | | | |
| 96 | Ac—(D)Phe—Pro—boroPhe(m-CH₂NHC(NH)NH₂)—C₁₀H₁₆ | | | |
| 97 | Ac—(D)Phe—Pro—boroPhe(m-CH₂NHC(NH)NHCN)—C₁₀H₁₆ | | | |
| 98 | Z—Leu—Ser(OT—Bu)—Asn—Leu—Ser(OT—Bu)—Asn—Leu—Ser(OT—Bu)—Asn—Leu—Ser(OT—Bu)—Asn—NHCH[(CH₂)₃NHC(NH)H]—B(OC₁₀H₁₆)₂ | | | |
| 99 | H—Leu—Ser(OT—Bu)—Asn—Leu—Ser(OT—Bu)—Asn—Leu—Ser(OT—Bu)—Asn—NHCH[(CH₂)₃NHC(NH)H]- | | | |

TABLE 1-continued

| EX # | Compound | Ms Method | LRMS CALC'D | LRMS FOUND |
|---|---|---|---|---|
| 100 | B(OC$_{10}$H$_{16}$)$_2$ Z—Leu—Ser—Asn—Leu—Ser—Asn—Leu—Ser—Asn—Leu—Ser—Asn—NHCH[(CH$_2$)$_3$NHC(NH)H]—B(OC$_{10}$H$_{16}$)$_2$ | | | |
| 101 | H—Leu—Ser—Asn—Leu—Ser—Asn—Leu—Ser—Asn—Leu—Ser—Asn—NHCH[(CH$_2$)$_3$NHC(NH)H]—B(OC$_{10}$H$_{16}$)$_2$ | | | |
| 102 | Boc—(D)Phe—Pro—boroGly[(CH$_2$)$_3$—ONH$_2$]—OH.HCl | NH$_3$/Cl (EG ester + H) | 519.3 | 519 |
| 103 | PhCH$_2$SO$_2$—(D)Phe—Pro—boroGly[(CH$_2$)$_3$—ONH$_2$]—C$_{10}$H$_{16}$.HCl | NH$_3$/Cl (M + H) | 681.4 | 681 |
| 104 | Boc—(D)Phe—Pro—boroGly[(CH$_2$)$_3$—ONHC(=NH)NH$_2$]—C$_{10}$H$_{16}$.HCl | NH$_3$/Cl (M + H) | 669.4 | 669 |
| 105 | Boc—(D)Phe—Pro—boroOrn[C(NCN)NHCH$_3$]—C$_{10}$H$_{16}$ | NH$_3$/Cl (M + NH$_4$) | 709.5 | 709 |
| 106 | HOOCCH$_2$—(D)Phe—Pro—boroOrn[C(NCN)NHCH$_3$]—C$_{10}$H$_{16}$.HCl | ESI (M + H) | 650.4 | 650.5 |
| 107 | Boc—(D)Phe—Pro—boroOrn[C(NCN)SCH$_3$]—C$_{10}$H$_{16}$ | NH$_3$/Cl (M + NH$_4$) | 726.4 | 726 |
| 108 | Boc—(D)Phe—Pro—boroOrn(CONH$_2$)—C$_{10}$H$_{16}$ | NH$_3$/Cl (M + NH$_4$) | 654.4 | 654 |
| 109 | H—(D)Phe—Pro—boroOrn(CONH$_2$)—C$_{10}$H$_{16}$.HCl | NH$_3$/Cl (M + H) | 554.4 | 554 |
| 110 | PhCH$_2$SO$_2$—(D)Phe—Pro—boroOrn(CONH$_2$)—C$_{10}$H$_{16}$ | NH$_3$/Cl (M + NH$_4$) | 725.4 | 725 |
| 111 | HOOCCH$_2$—(D)Phe—Pro—boroOrn(CONH$_2$)—C$_{10}$H$_{16}$.HCl | NH$_3$/Cl (M + H) | 612.4 | 612 |
| 112 | Boc—(D)Phe—Pro—boroOrn(COCH$_2$OH)—C$_{10}$H$_{16}$ | NH$_3$/Cl (M + NH$_4$) | 686.4 | 686 |
| 113 | Boc—(D)Phe—Pro—boroOrn(N-Methanesulfonyl)—C$_{10}$H$_{16}$ | NH$_3$/Cl (M + NH$_4$) | 706.4 | 706 |
| 114 | H—(D)Phe—Pro—boroOrn(N-Methanesulfonyl)-C$_{10}$H$_{16}$.HCl | NH$_3$/Cl (M + NH$_4$) | 589.3 | 589 |
| 115 | 4-(N-Acetyl)Anilinesulfonyl-(D)Phe—Pro—boroOrn(N-Methanesulfonyl)-C$_{10}$H$_{16}$ | NH$_3$/Cl (M + NH$_4$) | 803.4 | 803 |
| 116 | Methanesulfonyl-(D)Phe—Pro—boroOrn(N-Methanesulfonyl)-C$_{10}$H$_{16}$ | NH$_3$/Cl (M + NH$_4$) | 684.3 | 684 |
| 117 | N,N-dimethyl-(D)Phe—Pro—boroOrn-(N-Methanesulfonyl)-C$_{10}$H$_{16}$.HCl | NH$_3$/Cl (M + H) | 617.4 | 617 |
| 118 | Ac—Gly—(D)Phe—Pro—BoroOrn(N-Methanesulfonyl)-C$_{10}$H$_{16}$ | NH$_3$/Cl (M + NH$_4$) | 705.4 | 705 |
| 119 | HOOCCH$_2$—(D)Phe—Pro—boroOrn(N-Methanesulfonyl)-C$_{10}$H$_{16}$.HCl | NH$_3$/Cl (M + H) | 647.3 | 674 |
| 120 | PhCH$_2$SO$_2$—(D)Phe—Pro—boroOrn(N-Methanesulfonyl)-C$_{10}$H$_{16}$ | NH$_3$/Cl (M + H) | 760.4 | 760 |
| 121 | Boc—(D)Phe—Pro—boroGly[(CH$_2$)$_3$—OCH$_2$CH$_3$]—C$_{10}$H$_{16}$ | NH$_3$/Cl (M + NH$_4$) | 657.4 | 657 |
| 122 | Boc—(D)Phe—Pro—boroGly[(CH$_2$)$_3$—CN]—C$_{10}$H$_{16}$ | NH$_3$/Cl (M + NH$_4$) | 638.4 | 638 |
| 123 | Boc—(D)Phe—Pro—boroOrn(COCH$_3$)—C$_{10}$H$_{16}$ | NH$_3$/Cl (M + NH$_4$) | 670.4 | 670 |
| 124 | Ac—(D)Phe—Pro—NH—CH[CH2(4-amino-cyclohexyl)BO2—C10H16 | NH$_3$/Cl (M + H) | 607.4 | 607 |
| 125 | Boc—(D)Phe—Pro—NH—CH[CH$_2$(4-amino-cyclohexyl)]BO$_2$—C$_{10}$H$_{16}$ | NH$_3$/Cl (M + H) | 665.5 | 665.4 |
| 126 | Boc—(D)Phe—Pro—NH—CH[4-amino-cyclohexyl]BO$_2$—C$_{10}$H$_{16}$ | NH$_3$Cl (M + H) | 651.5 | 651.2 |
| 127 | Boc—(D)Phe—Pro—NH—CH[CH$_2$(4-hydroxy-cyclohexyl)]BO$_2$—C$_{10}$H$_{16}$ | NH$_3$/Cl (M + H) | 666.5 | 666.4 |
| 128 | Boc—(D)Phe—Pro—NH—CH[CH$_2$(4-guanidino-cyclohexyl)]BO$_2$—C$_{10}$H$_{16}$ | NH$_3$/Cl (M + H) | 707.5 | 707.4 |
| 129 | Boc—(D)Phe—Pro—(R)Phe(mCN)— | NH$_3$/Cl | 549.3 | 549.3 |

TABLE 1-continued

| EX # | Compound | Ms Method | LRMS CALC'D | LRMS FOUND |
|---|---|---|---|---|
| | OMe | (M + H) | | |
| 130 | Boc—(D)Phe—Pro—(S)Phe(mCN)—OMe | $NH_3$/Cl (M + H) | 549.3 | 549.3 |
| 131 | Boc—Pro—(S)Phe(mCN)—OMe | $NH_3$/Cl (M + $NH_4$) | 419 | 419 |
| 132 | Boc—Pro—Phe(mCN)—OH | $NH_3$/Cl (M + H) | 388.2 | 388.1 |
| 133 | Boc—Pro—Phe(mCN)—N(Me)—OMe | $NH_3$/Cl (M + $NH_4$) | 448.3 | 448 |
| 134 | Boc—Pro—Phe(mCN)—C(OEt)=$CH_2$ | $NH_3$/Cl (M + $NH_4$) | 459 | 459 |
| 135 | H—(D)Phe—Pro—boroPhe(mCOOMe)—$C_{10}H_{16}$·HCl | $NH_3$/Cl (M + H) | 602.3 | 602.3 |
| 136 | Hydrocinnamoyl-ProboroGly[$(CH_2)_4$—NH—Acetyl]$C_{10}H_{16}$ | $NH_3$/Cl (M + H) | 552.4 | 552.4 |
| 137 | Ac—(D)—Phe—Pro—boroGly[$(CH_2)_3$—$OCH_3$]—$C_{10}H_{16}$ | $NH_3$/Cl (M + H) | 568.61 | 568.53 |
| 138 | Boc—(D)—Phe—Pro—boroGly[$(CH_2)_3$—$OCH_3$]—$C_{10}H_{16}$ | $NH_3$/Cl (M + $NH_4$) | 643.4 | 643 |
| 139 | H—(D)—Phe—Pro—boroGly[$(CH_2)_3$—$OCH_3$]—$C_{10}H_{16}$ | $NH_3$/Cl (M + H) | 526.3 | 526.34 |
| 140 | $HO_2CCH_2$—(D)—Phe—Pro—boroGly[$(CH_2)_3$—$OCH_3$]—$C_{10}H_{16}$ | $NH_3$/Cl (M + H) | 584.4 | 584.4 |
| 141 | N,N-dimethyl-(D)—Phe—Pro—boroGly[$(CH_2)_3$—$OCH_3$]—$C_{10}H_{16}$ | $NH_3$/Cl (M + H) | 554.4 | 554 |
| 142 | N-methyl-(D)—Phe—Pro—boroGly[$(CH_2)_3$—$OCH_3$]—$C_{10}H_{16}$ | $NH_3$/Cl (M + H) | 540.4 | 540.36 |
| 143 | $(CH_3)_2CH$—(D)—Phe—Pro—boroGly[$(CH_2)_3$—$OCH_3$]—$C_{10}H_{16}$ | $NH_3$/Cl (M + H) | 568.4 | 568.4 |
| 144 | Ac—Gly—(D)—Phe—Pro—boroGly[$(CH_2)_3$—$OCH_3$]—$C_{10}H_{16}$ | $NH_3$/Cl (M + H) | 624.4 | 624 |
| 145 | H—Pro—(D)—Phe—Pro—boroGly[$(CH_2)_3$—$OCH_3$]—$C_{10}H_{16}$ | $NH_3$/Cl (M + H) | 623.3 | 623 |

Additional examples of compounds included within the scope of the current invention are found in Table 2.

TABLE 2

$$R^3\text{-}[A]_n\text{-}N(R^2)\text{-}CH(R^1)\text{-}B(Y^1)(Y^2)$$

| Ex # | $R^3$—[A]$_n$— | $R^1$ | $Y^1, Y^2$ | $R^2$ |
|---|---|---|---|---|
| 146 | Ac—(D)Phe—Pro | 4-($CH_2CN$)phenyl | —$C_{10}H_{16}$ ester | H |
| 147 | Ac—(D)Phe—Pro | 4-(C(NH)$NH_2$)phenyl | —$C_{10}H_{16}$ ester | H |
| 148 | Ac—(D)Phe—Pro | 4-($CH_2NH_2$)phenyl | —$C_{10}H_{16}$ ester | H |

EXAMPLES 98;99;100;101 REPRESENT SEQ ID NO:1; SEQ ID NO:2: SEQ ID NO:3 AND SEQ ID NO:4 RESPECTIVELY

Utility

N-Acyl and N-peptide boronic acids and amino acids which are described in the present invention represent a novel class of potent inhibitors of trypsin-like enzymes. Trypsin-like enzymes are a group of proteases which hydrolyzed peptide bonds at basic residues liberating either a C-terminal arginyl or lysyl residue. Among these are enzymes of the blood coagulation and fibrinolytic system required for hemostasis. They are Factors II, X, VII, IX, XII, kallikrein, tissue plasminogen activators, urokinase-like plasminogen activator, and plasmin. Enzymes of the complement system, acrosin (required for fertilization), pancreatic trypsin are also in this group. Elevated levels of proteolysis by these proteases can result in disease states. For example, consumptive coagulopathy, a condition marked by a decrease in the blood levels of enzymes of both the coagulation system, the fibrinolytic system and accompanying protease inhibitors is often fatal. Intervention by a synthetic inhibitor would clearly be valuable. More specifically, proteolysis by thrombin is required for blood clotting. Inhibition of thrombin results in an effective inhibitor of blood clotting. The importance of an effective inhibitor of thrombin is underscored by the observation that conventional anticoagulants such as heparin (and its complex with the protein inhibitor, antithrombin III) are ineffective in blocking arterial thrombosis associated with myocardial infractions and other clotting disorders. However, a low molecular weight thrombin inhibitor, containing a different functionality, was effective in blocking arterial thrombosis [Hanson and Harker (1988) Proc. Natl. Acad. Sci. U.S.A. 85, 3184–3188]. Therefore, we have chosen to demonstrate utility of compounds in the inhibition of thrombin, both as in buffered solutions and in plasma. Specifically, the compounds have utility as drugs for the treatment of diseases arising from elevated thrombin activity such as myocardial infarction, and as reagents used as anticoagulants in the processing of blood to plasma for diagnostic and other commercial purposes.

Compounds of the present invention are expected to be effective in the control of aberrant proteolysis and a number of accompanying disease states such as inflammation, pancretitis, and heritary angioedema.

The effectiveness of compounds of the present invention as inhibitors of blood coagulation proteases was determined using purified human proteases and synthetic substrates following procedures similar to those described in Kettner et al. (1990).

For these assays, the rate of enzymatic (thrombin, Factor Xa, and Factor VIIa) hydrolysis of chromogenic substrates (S2238 (H-D-Phe-Pip-Arg-pNA), S2222, and S2288, respectively; Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Thrombin and Xa determinations were made in 0.10M sodium phosphate buffer, pH 7.5, containing 0.20M NaCl, and 0.5% PEG 8000. VIIa determinations were made in 0.05M tris buffer, pH 7.6, containing 0.10M NaCl, 4 mM $CaCl_2$, and 0.1% bovine serum albumin. The Michaelis constant, $K_m$, for substrate hydrolysis was determined at 25° C. using the method of Lineweaver and Burk.

Values of $K_i$ were determined by allowing 0.2–0.5 nM human thrombin or human factor Xa (Enzyme Research Laboratories, South Bend, Ind.), or 50 nM human factor VIIa (BiosPacific, Emeryville, Calif.) react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values.

$$\frac{v_o - v_s}{v_s} = \frac{I}{Ki(1 + S/K_m)}$$

where:

$v_o$ is the velocity of the control in the absence of inhibitor;

$v_s$ is the velocity in the presence of inhibitor;

I is the concentration of inhibitor;

$K_i$ is the dissociation constant of the enzyme: inhibitor complex;

S is the concentration of substrate;

$K_m$ is the Michaelis constant.

Using the methodology described above, representative compounds of this invention were evaluated and found to exhibit a $K_i$ of less 500 μM thereby confirming the utility of compounds of the invention as effective inhibitors of human blood coagulation proteases. The results of these assays are summarized in Table 3, where +++ indicates a $K_i$<500 nM; ++ indicates a $K_i$<50,000 nM; + indicates a $K_i$ 500,000<nM; – indicates inactive; and NT indicates Not Tested.

TABLE 3

$K_i$ values for inhibition of Serine Proteases by compounds of the present invention.

| Ex No. EX # | Thrombin Ki (nM) | Factor Xa Factor XA Ki (nM) | Factor VIIa Factor VIIA Ki (nM) | $IC_{50}$ Thrombin time Factor VIIA Ki (nM) |
|---|---|---|---|---|
| 1 | ++ | NT | NT | |
| 2 | +++ | NT | NT | |
| 3 | +++ | NT | NT | |
| 4 | +++ | +++ | +++ | |
| 6 | +++ | NT | NT | |
| 7 | +++ | +++ | +++ | |
| 8 | +++ | NT | NT | |
| 9 | +++ | NT | NT | |
| 11 | +++ | ++ | +++ | |
| 12 | +++ | NT | NT | |
| 13 | +++ | NT | NT | |
| 14 | +++ | NT | NT | |
| 15 | +++ | NT | NT | |
| 16 | +++ | NT | NT | |
| 17 | +++ | NT | NT | |
| 18 | +++ | NT | NT | |
| 19 | +++ | NT | NT | |
| 20 | +++ | +++ | NT | |
| 21 | +++ | NT | NT | |
| 22 | +++ | NT | NT | |
| 23 | +++ | ++ | +++ | |
| 24 | +++ | +++ | NT | |
| 25 | +++ | +++ | NT | |
| 26 | ++ | NT | NT | |
| 27 | +++ | +++ | NT | |
| 28 | +++ | +++ | NT | |
| 29 | +++ | NT | NT | |
| 30 | +++ | +++ | NT | |
| 31 | +++ | +++ | NT | |
| 32 | +++ | +++ | NT | |
| 33 | +++ | NT | NT | |
| 34 | +++ | +++ | +++ | |
| 35 | ++ | NT | NT | |
| 36 | +++ | +++ | +++ | |
| 37 | +++ | ++ | +++ | |
| 38 | +++ | ++ | +++ | |
| 39 | +++ | +++ | +++ | |
| 40 | +++ | +++ | +++ | |
| 41 | +++ | NT | NT | |
| 42 | +++ | NT | NT | |

TABLE 3-continued

K_i values for inhibition of Serine Proteases by compounds of the present invention.

| Ex No. EX # | Thrombin Factor Xa Thrombin Ki (nM) | Factor VIIa Factor XA Ki (nM) | IC$_{50}$ Thrombin time Factor VIIA Ki (nM) |
|---|---|---|---|
| 43 | +++ | NT | NT |
| 44 | +++ | NT | NT |
| 45 | +++ | NT | NT |
| 46 | +++ | NT | NT |
| 47 | +++ | NT | NT |
| 48 | +++ | ++ | +++ |
| 49 | + | NT | NT |
| 50 | ++ | NT | NT |
| 51 | +++ | NT | NT |
| 52 | +++ | NT | NT |
| 53 | ++ | NT | NT |
| 54 | +++ | NT | NT |
| 55 | +++ | NT | NT |
| 56 | +++ | NT | NT |
| 57 | +++ | NT | NT |
| 58 | +++ | NT | NT |
| 59 | +++ | NT | NT |
| 60 | +++ | NT | NT |
| 61 | +++ | NT | NT |
| 62 | +++ | NT | NT |
| 63 | +++ | NT | NT |
| 64 | +++ | NT | NT |
| 65 | +++ | NT | NT |
| 66 | +++ | NT | NT |
| 67 | +++ | NT | NT |
| 68 | +++ | NT | NT |
| 69 | +++ | NT | NT |
| 70 | +++ | NT | NT |
| 71 | +++ | NT | NT |
| 73 | +++ | NT | NT |
| 74 | +++ | NT | NT |
| 76 | +++ | NT | NT |
| 102 | +++ | ++ | +++ |
| 103 | +++ | NT | NT |
| 104 | +++ | NT | NT |
| 105 | +++ | NT | NT |
| 106 | +++ | NT | NT |
| 107 | +++ | NT | NT |
| 108 | +++ | NT | NT |
| 109 | +++ | NT | NT |
| 110 | +++ | ++ | NT |
| 111 | +++ | NT | NT |
| 112 | +++ | NT | NT |
| 113 | +++ | NT | NT |
| 114 | +++ | NT | NT |
| 115 | +++ | NT | NT |
| 116 | +++ | NT | NT |
| 117 | +++ | NT | NT |
| 118 | +++ | NT | NT |
| 119 | +++ | NT | NT |
| 120 | +++ | NT | NT |
| 121 | +++ | NT | NT |
| 122 | ++ | NT | NT |
| 123 | +++ | NT | NT |
| 124 | +++ | ++ | NT |
| 125 | +++ | NT | NT |
| 126 | +++ | NT | NT |
| 127 | +++ | NT | NT |
| 128 | +++ | NT | NT |
| 129 | +++ | NT | NT |
| 130 | +++ | NT | NT |
| 135 | +++ | NT | NT |
| 136 | +++ | ++ | ++ |
| 137 | ++ | NT | NT |
| 138 | +++ | NT | NT |
| 139 | +++ | NT | NT |
| 140 | +++ | NT | ++ |
| 141 | +++ | ++ | ++ |
| 142 | +++ | NT | NT |
| 143 | +++ | NT | NT |
| 144 | +++ | NT | NT |
| 145 | +++ | NT | NT |
| 146 | +++ | NT | NT |

Representative of data for compounds of the present invention, Examples 3, 7, 9, 11, and 12 increased thrombin clotting times 2-fold at 0.25, <0.075, 0.10, 0.60, and 0.85 μM, respectively.

The effectiveness of compounds of the present invention as anticoagulants in vivo was demonstrated by the prolongation of the activated partial thromboplastin time of samples of blood taken from conscious dogs or anesthetized rats after either oral or intravenous administration at doses of the compounds from 0.5 to 10 mg/kg. Arterial or venous blood was withdrawn by syringe and mixed with 1/10 volume 3.2% sodium citrate. Plasma was obtained after centrifugation and a standard clinical activated partial thromboplastin time (APTT reagent, Sigma Chemical Co., St. Louis, Mo.) determined at 37° C. in a fibrometer. Results from blood samples obtained at various times after dosing showed an effective anticoagulant response which was at least equivalent to doubling of activated partial thromboplastin time as compared to the value obtained prior to dosing. In this model, Examples 4, 57, and 77 were shown to be effective following i.v. dosing and Examples 4, 56, 57, 60, and 66 effective following oral dosing. Similarly, oral administration of Examples 31 and 54 resulted in at least a 2-fold elevation in anticoagulant activity in an identical model except activity was measured by increases in thrombin clotting times.

What is claimed is:
1. A compound of formula (I)

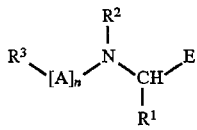

wherein

E is -BY$^1$Y$^2$;

Y$^1$ and Y$^2$ are
 a) —OH, or when taken together Y$^1$ and Y$^2$ form
 b) a cyclic boron ester where said chain or ring contains from 2 to 20 carbon atoms and, optionally, 1–3 heteroatoms which can be N, S, or O;

R$^1$ is
 a) C1–C12-alkyl substituted with —NHC(NH)H, —ONHR$^6$, or —ONHC(=NH)NHR$^6$;
 b)

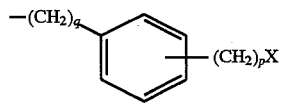

where X is
 aa) —CN
 bb) —NHC(NH)H
 cc) —C(O)NHR$^2$
 dd) —CO$_2$R$^2$
 ee) —OR$^2$, or
 ff) —NHC(=NR$^6$)H;
 c)

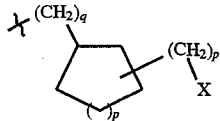

where X is as defined above and in addition can be selected from —NH$_2$, —NHC(NH)NHR$^6$, or —C(NH)NHR$^6$; or
 d)

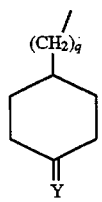

where Y is O;

R$^2$ is
 a) H,
 b) optionally substituted C1–C12-alkyl,
 c) optionally substituted cycloalkyl,
 d) optionally substituted aryl, where aryl is phenyl or napthyl, or
 e) optionally substituted -C1–C4-alkylaryl, where aryl is phenyl or napthyl;
 wherein the groups C1–C12-alkyl, cycloalkyl, aryl, and C1–C4-alkylaryl are optionally substituted with one or two substituents selected from the group consisting of:

halo (F, Cl, Br, I), C1–C4-alkyl, C1–C4-alkoxy, —NO$_2$, -CF$_3$, —S(O)$_r$-C1–C4-alkyl, —OH, —NH$_2$, —NH(C1-C4-alkyl), —N(C1–C4-alkyl)$_2$, or —CO$_2$R$^4$;

R$^3$ is H, alkyl, aryl, alkylaryl, —S(O)$_r$-R$^7$, —C(=O)R$^7$, —C(=O)OR$^7$, —P(O)$_2$OR$^7$ or a NH$_2$ blocking group having from 1–20 carbon atoms;

R$^4$ is
 a) hydrogen,
 b) C$_1$–C$_4$ alkyl,
 c) -(C$_1$–C$_4$ alkyl)-aryl, where aryl is phenyl or napthyl, or
 d) C$_5$–C$_7$ cycloalkyl;

R$^6$ and R$^7$ are independently:
 a) H,
 b) -C1–C4-alkyl,
 c) aryl, wherein aryl is phenyl or napthyl optionally substituted with one or two substituents selected from the group consisting of:
 halo (F, Cl, Br, I), C1–C4-alkyl, C1–C7-alkoxy, —NO$_2$, —CF$_3$,—S(O)$_r$-C1–C4-alkyl, —OH, —NH$_2$,—NH(C1-C4-alkyl), —N(C1–C4-alkyl), —N(C1–C4-alky)$_2$ and —CO$_2$R$^4$, or
 d) -C1–C4-alkylaryl, where aryl is as defined above;

A is an amino acid residue or a peptide having from 2–20 amino acid residues;

n is 0 or 1;

p is 0 to 3;

q is 0 to 4;

r is 0 to 2;

or a pharmaceutically acceptable salt thereof.

2. A compound of claim 1 wherein A is an amino acid residue or a peptide having from 2–20 amino acids residues selected from Ala, Arg, Ash, Asp, Aze., Cys, Gln, Glu, Gly, His, Ile, Irg, Leu, Lys, Met, Orn, Phe, Phe (4-fluoro), Pro, Sar, Ser, Thr, Trp, Tyr, Val, 2-aminobutanoicacid, 2-aminopentanoic acid, 2-aminohexanoic acid, 2-aminoheptanoic acid, 2-aminooctanoic acid, 2-aminononanoic acid, 2-aminodecanoic acid, 2-aminoundecanoic acid, 2-amino-3,3-dimethylbutanoic acid, 2-amino-4,4-dimethylpentanoic acid, 2-amino-3-methylhexanoic acid, 2-amino-3-methylheptanoic acid, 2-amino-3-methyloctanoic acid, 2-amino-3-methylnonanoic acid, 2-amino-4-methylhexanoic acid, 2-amino-3-ethylpentanoic acid, 2-amino-3,4-dimethylpentanoic acid, 2-amino-3,5-dimethylhexanoic acid, 2-amino-3,3-dimethylpentanoic acid, 2-amino-3-ethyl-3-methylpentanoic acid, 2-amino-3,3-diethylpentanoic acid, 2-amino-5-methylhexanoic acid, 2-amino-6-methylheptanoic, 2-amino-7-methyloctanoic, 2-amino-2-cyclopentylacetic, 2-amino-2-cylcohexylacetic acid, 2-amino-2-(1-methylcylcohexyl)acetic acid, 2-amino-2-(2-methyl-1-methylcylcohexyl)acetic acid, 2-amino-2-(3-methyl-1-methylcylcohexyl)acetic acid, 2-amino-2-(4-methyl-1-methylcylcohexyl)acetic acid, 2-amino-2-(1-ethylcycolhexyl)acetic acid, 2-amino-3-(cyclohexyl)propanoic acid, 2-amino-4-(cyclohexyl)butanoic acid, 2-amino-3-(1-adamantyl)propanoic acid, 2-amino-3-butenoic acid, 2-amino-3-methyl-3-butenoic acid, 2-amino-4-pentenoic acid, 2-amino-4-hexenoic acid, 2-amino-5-heptenoic acid, 2-amino-4-methyl-4-hexenoic acid, 2-amino-5-methyl-4-hexenoic acid, 2-amino-4-methy-5-hexenoic acid, 2-amino-6-heptenoic acid, 2-amino-3,3,4-trimethyl-4-pentenoic acid, 2-amino-4-chloro-4-pentenoic, 2-amino-4,4-dichloro-3-butenoic acid, 2-amino-3-(2-methylenecyclopropyl)-propanoic acid, 2-amino-2-(2- cyclopentenyl)acetic acid, 2-amino-2-(cyclohexenyl)acetic acid, 2-amino-3-(2-cyclopentenyl)propanoic acid, 2-amino-3-(3-cyclopentenyl)propanoic acid, 2-amino-3-(1-cyclohexyl)propanoic acid, 2-amino-2-(1-cyclopentenyl)acetic acid, 2-amino-2-(1-cylcohexyl)acetic acid, 2-amino-2-(1-cylcoheptenyl)acetic acid, 2-amino-2-(1-cyclooctenyl)acetic acid, 2-amino-3-(1-cycloheptenyl)propanoic acid, 2-amino-3-(1,4-cyclohexadienyl)propanoic acid, 2-amino-3-(2,5-cyclohexadienyl)propanoic acid, 2-amino-2-(7-cycloheptatrienyl)acetic acid, 2-amino-4,5-hexadienoic acid, 2-amino-3-butynoic acid, 2-amino-4-pentyoic acid, 2-amino-4-hexynoic acid, 2-amino-4-hepten-6-ynoic acid, 2-amino-3-fluoropropanoic acid, 2-amino-3,3,3-trifluoropropanoic acid, 2-amino-3-fluorobutanoic acid, 2-amino-3-fluoropentanoic acid, 2-amino-3-fluorohexanoic acid, 2-amino-3,3-difluorobutanoic acid, 2-amino-3,3-difluoro-3-phenylpropanoic acid, 2-amino-3-perfluoroethylpropanoic acid, 2-amino-3-perfluoropropylpropanoic acid, 2-amino-3-fluoro-3-methylbutanoic acid, 2-amino-5,5,5-trifluoropentanoic acid, 2-amino-3-methyl-4,4,4-trifluorobutanoic acid, 2-amino-3-trifluoromethyl-4,4,4-trifluorobutanoic acid, 2-amino-3,3,4,4,5,5-heptafluoropentanoic acid, 2-amino-3-methyl-5-fluoropentanoic acid, 2-amino-3-methyl-4-fluoropentanoic acid, 2-amino-5,5-difluorohexanoic acid, 2-amino-4-(fluoromethyl)-5-fluoropentanoic acid, 2-amino-4-trifluoromethyl-5,5,5-trifluoropentanoic acid, 2-amino-3-fluoro-3-methylbutanoic acid, 2-amino-3-fluoro-3-phenylpentanoic acid, 2-amino-2-(1-fluorocyclopentyl)acetic acid, 2-amino-2-(1-fluorocyclohexyl)acetic acid, 2-amino-3-chloropropanoic acid acid, 2-amino-3-chlorobutanoic acid acid, 2-amino-4,4-dichlorobutanoic acid acid, 2-amino4,4,4-trichlorobutanoic acid, 2-amino-3,4,4-trichlorobutanoic acid, 2-amino-6-chlorohexanoic acid, 2-amino-4-bromobutanoic acid, 2-amino-3-bromobutanoic acid, 2-amino-3-mercaptobutanoic acid, 2-amino-4-mercaptobutanoic acid, 2-amino-3-mercapto-3,3-dimethylpropanoic acid, 2-amino-3-mercapto-3-methylpentanoic acid, 2-amino-3-mercaptopentanoic acid, 2-amino-3-mercapto-4-methylpentanoic acid, 2-amino-3-methyl-4-mercaptopentanoic acid, 2-amino-5-mercapto-5-methylhexanoic acid, 2-amino-2-(1-mercaptocyclobutyl)acetic acid, 2-amino-2-(1-mercaptocyclopentyl)acetic acid, 2-amino-2-(1-mercaptocyclohexyl)acetic acid, 2-amino-5-(methylthio)pentanoic acid, 2-amino-6-(methylthio)hexanoic acid, 2-amino-4-methylthio-3-phenylbutanoic acid, 2-amino-5-ethylthio-5-methylpentanoic acid, 2-amino-5-ethylthio-3,5,5-trimethylpentanoic acid, 2-amino-5-ethylthio-5-phenylpentanoic acid, 2-amino-5-ethylthio-5-pentanoic acid, 2-amino-5-butylthio-5-methylpentanoic acid, 2-amino-5-butylthio-3,5,5-trimethylpentanoic acid, 2-amino-5-butylthio-5-phenylpentanoic acid, 2-amino-5-(butylthio)pentanoic acid, 2-amino-3-methy4-hydroselenopentanoic acid, 2-amino-4-methylselenobutanoic acid, 2-amino-4-ethylselenobutanoic acid, 2-amino-4-benzylselenobutanoic acid, 2-amino-3-methyl-4-(methylseleno)butanoic acid, 2-amino-3-(aminomethylseleno)propanoic acid, 2-amino-3-(3-aminopropylseleno)propanoic acid, 2-amino-4-methyltellurobutanoic acid, 2-amino-4-hydroxybutanoic acid, 2-amino-4-hydroxyhexanoic acid, 2-amino-3-hydroxypentanoic acid, 2-amino-3-hydroxyhexanoic acid, 2-amino-3methyl-4-hydroxybutanoic acid, 2-amino-3-hydroxy-3-methylbutanoic acid, 2-amino-6-hydroxyhexanoic acid, 2-amino-4-hydroxyhexanoic acid, 2-amino-3-hydroxy-4-methylpentanoic acid, 2-amino-3-hydroxy-3-methylpentanoic acid, 2-amino4-hydroxy-3,3-dimethylbutanoic acid, 2-amino-3-hydroxy4-methylpentanoic acid, 2-amino-3-hydroybutanedioic acid, 2-amino-3-hydroxy-3-phenyl-propanoic acid, 2-amino-3-hydroxy-3-(4-nitrophenyl)propanoic acid, 2-amino-3-hydroxy-3-(3-pyridyl)propanoic acid, 2-amino-2-(1-hydroxycyclopropyl)acetic acid, 2-amino-3-(1-hydroxycyclohexyl)propanoic acid, 2-amino-3-hydroxy-3-phenylpropanoic acid, 2-amino-3-hydroxy-3-[3-bis(2-chloroethyl)aminophenyl]propanoic acid, 2-amino-3-hydroxy-3-(3,4-dihydroxyphenyl)propanoic acid, 2-amino-3-hydroxy-3-(3,4-methylenedioxyphenyl)propanoic acid, 2-amino-4-fluoro-3-hydroxybutanoic acid, 2-amino-4,4,4-trichloro-3-hydroxybutanoic acid, 2-amino-3-hydroxy-4-hexynoic acid, 2-amino-3,4-dihydroxybutanoic acid, 2-amino-3,4,5,6-tetrahydroxyhexanoic acid, 2-amino-4,5-dihydroxy-3-methylpentanoic acid, 2-amino-5,6-dihydroxyhexanoic acid, 2-amino-5-hydroxy-4-(hydroxyrnethyl)pentanoic acid, 2-amino-4,5-dihydroxy-4-(hydroxymethyl)pentanoic acid, 2-amino-3-hydroxy-5-benzyloxypentanoic acid, 2-amino-3-(2-aminoethoxy)propanoic acid, 2-amino-4-(2-aminoethoxy)butanoic acid, 2-amino-4-oxobutanoic acid, 2-amino-3-oxobutanoic acid, 2-amino-4-methyl-3-oxopentanoic acid, 2-amino-3-phenyl-3-oxopropanoic acid, 2-amino-4-phenyl-3-oxobutanoic acid, 2-amino-3-methyl-4-oxopentanoic acid, 2-amino-4-oxo-4-(4-hydroxyphenyl)butanoic acid, 2-amino-4-oxo-4-(2-furyl)butanoic acid, 2-amino-4-oxo-4-(2-nitrophenyl)butanoic acid, 2-amino-4-oxo-4-(2-amino-4-chlorophenyl)butanoic acid, 2-amino-3-(4-oxo-1-cyclohexenyl)propanoic acid, 2-amino-3-(4-oxocyclohexanyl)propanoic acid, 2-amino-3-(2,5-dimethyl-3,6-dioxo-1,4-cydohexadienyl)propanoic acid, 2-amino-3-(1-hydroxy-5-methyl-7-oxo-cyclohepta-1,3,5-trien-2-yl)propanoic acid, 2-amino-3-(1-hydroxy-7-oxo-cyclohepta-1,3,5-trien-3-yl)propanoic acid, 2-amino-3-(1-hydroxy-7-oxo-cyclohepta-1,3,5-trien-4-yl)propanoic acid, 2-amino-4-methoxy-3-butenoic acid, 2-amino-4-(2-aminoethoxy)-3-butenoic acid, 2-amino-4-(2-amino-3-hydroxypropyl)-3-butenoic acid, 2-amino-2-(4-methoxy-1,4-cyclohexadienyl)acetic acid, 2-amino-3,3-diethoxypropanoic acid, 2-amino-4,4-dimethylbutanoic acid, 2-amino-2-(2,3-epoxycyclohexyl)acetic acid, 2-amino-3-(2,3-epoxycyclohexy)propanoic acid, 2-amino-8-oxo-9,10-epoxydecanoic acid, 2-amino-propanedioic acid, 2-amino-3-methylbutanedioic acid, 2-amino-3,3-dimethylbutanedioic acid, 2-amino4-methylpentanedioic acid, 2-amino-3-methylpentanedioic acid, 2-amino-3-phenylpentanedioic acid, 2-amino-3-hydroxypentanedioic acid, 2-amino-3-carboxypentanedioic acid, 2-amino-4-ethylpentanedioic acid, 2-amino-4-propylpentanedioic acid, 2-amino-4-isoamylpentanedioic acid, 2-amino-4-phenylpentanedioic acid, 2-amino-hexanedioic acid, 2-amino-heptanedioic acid, 2-amino-decanedioic acid, 2-amino-octanedioic acid, 2-amino-dodecanedioic acid, 2-amino-3-methylenebutanedioic acid, 2-amino-4-methylenepentanedioic acid, 2-amino-3-fluorobutanedioic acid, 2-amino-4-fluoropentanedioic acid, 2-amino-3,3-difluorobutanedioic acid, 2-amino-3-chloropentanedioic acid, 2-amino-3-hydroxybutanedioic acid, 2-amino-4-hydroxypentanedioic acid, 2-amino-4-hydroxyhexanedioic acid, 2-amino-3,4-dihydroxypentanedioic acid, 2-amino-3-(3-hydroxypropyl)butanedioic acid, 2-amino-3-(1-carboxy-4-hydroxy-2-cyclodienyl)propanoic acid, 2-amino-3-(aceto)butanedioic acid, 2-amino-3-cyanobutanedioic acid, 2-amino-3-(2-carboxy-6-oxo-6H-pyranyl)propanoic acid, 2-amino-3-carboxybutanedioic acid, 2-amino-4-carboxypentanedioic acid, 3-amido-2-amino-3-hydroxypropanoic acid, 3-arnido-2-amino-3- methylpropanoic acid, 3-amido-2-amino-3-phenylpropanoic acid, 3-amido-2,3-diaminopropanoic acid, 3-amido-2-amino-3-[N-(4-hydroxyphenyl)amino]propanoic acid, 2,3-diaminopropanoic acid, 2,3-diaminobutanoic acid, 2,4-diaminobutanoic acid, 2,4-diamino-3-methylbutanoic acid, 2,4-diamino-3-phenylbutanoic acid, 2-amino-3-(methylamino)butanoic acid, 2,5-diamino-3-methylpentanoic acid, 2,7-diaminoheptanoic acid, 2,4-diaminoheptanoic acid, 2-amino-2-(2-piperidyl)acetic acid, 2-amino-2-(1-aminocyclohexyl)acetic acid, 2,3-diamino-3-phenylpropanoic acid, 2,3-diamino-3-(4-hydroxyphenyl)propanoic acid, 2,3-diamino-3-(4-methoxyphenyl)propanoic acid, 2,3-diamino-3-[4-(N,N'-dimethyamino)phenyl]propanoic acid, 2,3-diamino-3-(3,4-dimethoxyphenyl)propanoic acid, 2,3-diamino-3-(3,4-methylenedioxyphenyl)propanoic acid, 2,3-diamino-3-(4-hydroxy-3-methoxyphenyl)propanoic acid, 2,3-diamino-3-(2-phenylethyl)propanoic acid, 2,3-diamino-3-propylpropanoic acid, 2,6-diamino-4-hexenoic acid, 2,5-diamino-4-fluoropentanoic acid, 2,6-diamino-5-fluorohexanoic acid, 2,6-diamino-4-hexynoic acid, 2,6-diamino-5,5-difluorohexanoic acid, 2,6-diamino-5,5-dimethylhexanoic acid, 2,5-diamino-3-hydroxypentanoic acid, 2,6-diamino-3-hydroxyhexanoic acid, 2,5-diamino-4-hydroxypentanoic acid, 2,6-diamino-4-hydroxyhexanoic acid, 2,6-diamino-4-oxohexanoic acid, 2,7-diaminooctanedioic acid, 2,6-diamino-3-carboxyhexanoic acid, 2,5-diamino-4-carboxypentanoic acid, 2-amino-4-[2-(N,N'-diethylamino)ethyl]pentandioic acid, 2-amino-4-(N,N'-diethylamino)pentandioic acid, 2-amino-4-(N-morpholino)pentandioic acid, 2-amino-4-[N,N'-bis(2-chloroethyl)amino]pentandioic acid, 2-amino-4-[N,N'-bis(2-hydroxyethyl)amino]pentandioic acid, 2,3,5-triaminopentanoic acid, 2-amino-3-[N-(2-aminethyl)amino]propanoic acid, 2-amino-3-[(2-aminoethyl)seleno]propanoic acid, 2-amino-3-[(2-aminoethyl)thio]propanoic acid, 2-amino4-aminooxybutanoic acid, 2-amino-5-hydroxyaminopentanoic acid, 2-amino-5-[N-(5-nitro-2-pyrimidinyl)amino]pentanoic acid, 2-amino-4-[(7-nitro-2,1,3-benzoxadiazol-4-yl)amino]butanoic acid, 2-amino-3-guanidinopropanoic acid, 2-amino-3-guanidinobutanoic acid, 2-amino-4-guanidobutanoic acid, 2-amino-6-guanidohexanoic acid, 2-amino-6-ureidohexanoic acid, 2-amino-3-(2-iminoimidiazolin-4-yl)propanoic acid, 2-amino-2-(2-iminohexahydropyrimidin-4-yl)acetic acid, 2-amino-3-(2-iminohexahydropyrimidiny-4-yl)propanoic acid, 2-amino4-fluoro-5-guanidopentanoic acid, 2-amino-4-hydroxy-5-guanidopentanoic acid, 2-amino-4-guanidooxybutanoic acid, 2-amino-6-amidinohexanoic acid, 2-amino-5-(N-acetimidoylamino)pentanoic acid, 1-aminocyclopropanecarboxylic acid, 1-amino4-ethylcyclpropanecarboxylic acid, 1-aminocyclopentanecarboxylic acid, 1-aminocyclopentanecarboxylic acid, 1-amino-2,2,5,5-tetramethyl-cyclohexanecarboxylic acid, 1-aminocydoheptanecarboxylic acid, 1-aminocyclononanecarboxylic acid, 2-aminoindan-2-carboxylic acid, 2-aminonorbornane-2-carboxylic acid, 2-amino-3-phenylnorbornane-2-carboxylic acid, 3-aminotetrahydrothiophene-3-carboxylic acid, 1-amino-1,3-cyclohexanedicarboxylic acid, 3-aminopyrrolidine-3-carboxylic acid, 1,4-diaminocyclohexanecarboxylic acid, 6-alkoxy-3-amino-1,2,3,4-tetrahydrocarbazole-3-carboxylic acid, 2-aminobenzobicyclo[2,2,2]octane-2-carboxylic acid, 2-aminoindan-2-carboxylic acid, 1-amino-2-(3,4-dhydroxyphenyl)cyclopropanecarboxylic acid, 5,6-dialkoxy-2-aminoindane-2-carboxylic acid, 4,5-dihydroxy-2-aminoindan-2-caroxylic acid, 5,6-dihydroxy-2-aminotetralin-2-carboxylic acid, 2-amino-2-cyanoacetic acid, 2-amino-3-cyanopropanoic acid, 2-amino-4-cyanobutanoic acid, 2-amino-5-nitropentanoic acid, 2-amino-6-nitrohexanoic acid, 2-amino-4-aminooxybutanoic acid, 2-amino-3-(N-nitrosohydroxyamino)propanoic acid, 2-amino-3-ureidopropanoic acid, 2-amino-4-ureidobutanoic acid, 2-amino-3-phosphopropanoic acid, 2-amino-3-thiophosphopropanoic acid, 2-amino-4-methanephosphonylbutanoic acid, 2-amino-3-(trimethylsilyl)propanoic acid, 2-amino-3-(dimethyl(trimethylsilylmethylsilyl)propanoic acid, 2-amino-2-phenylacetic acid, 2-amino-2-(3-chlorophenyl)acetic acid, 2-amino-2-(4-chlorophenyl)acetic acid, 2-amino-2-(3-fluorophenyl)acetic acid, 2-amino-2-(3-methylphenyl)acetic acid, 2-amino-2-(4ofluorophenyl)acetic acid, 2-amino-2-(4-methylphenyl)acetic acid, 2-amino-2-(4-methoxyphenyl)acetic acid, 2-amino-2-(2-fluorophenyl)acetic acid, 2-amino-2-(2-methylphenyl)acetic acid, 2-amino-2-(4-chloromethylphenyl)acetic acid, 2-amino-2-(4-hydroxymethylphenyl)acetic acid, 2-amino-2-[4-(methylthiomethyl)phenyl]acetic acid, 2-amino-2-(4-bromomethylphenyl)acetic acid, 2-amino-2-[4-(methoxymethy)phenyl]acetic acid, 2-amino-2-[4-((N-benzylamino)methyl)phenyl]acetic acid, 2-amino-2-(4-hydroxylphenyl)acetic acid, 2-amino-2-(3-hydroxylphenyl)acetic acid, 2-amino-2-(3-carboxyphenyl)acetic acid, 2-amino-2-(4-aminophenyl)acetic acid, 2-amino-2-(4-azidophenyl)acetic acid, 2-amino-2-(3-t-butyl-4-hydroxyphenyl)acetic acid, 2-amino-2-(3,5-difluoro-4-hydroxyphenyl)acetic acid, 2-amino-2-(3,5-dihydroxyphenyl)acetic acid, 2-amino-2-(3-carboxy-4-hydroxyphenyl)acetic acid, 2-amino-2-(3,5-di-t-butyl-4-hydroxyphenyl)acetic acid, 2-amino-3-(2-methylphenyl)propanoic acid, 2-amino-3-(4-ethylphenyl)propanoic acid, 2-amino-3-(4-phenylphenyl)propanoic acid, 2-amino-3-(4-benzylphenyl)propanoic acid, 2-amino-3-(3-fluorophenyl)propanoic acid, 2-amino-3-(4-methylphenyl)propanoic acid, 2-amino-3-(4-fluorophenyl)propanoic acid, 2-amino-3-(4-chlorophenyl)propanoic acid, 2-amino-3-(2-chlorophenyl)propanoic acid, 2-amino-3-(4-bromophenyl)propanoic acid, 2-amino-3-(2-bromophenyl)propanoic acid, 2-amino-3-(3-hydroxyphenyl)propanoic acid, 2-amino-3-(2-hydroxyphenyl)propanoic acid, 2-amino-3-(4-mercaptophenyl)propanoic acid, 2-amino-3-(3-trifluoromethylphenyl)propanoic acid, 2-amino-3-(3-hydroxyphenyl)propanoic acid, 2-amino-3-(4-hydroxyphenyl)propanoic acid, 2-amino-3-[4-(hydroxymethy)phenyl]propanoic acid, 2-amino-3-[3-(hydroxymethyl)phenyl]propanoic acid, 2-amino-3-[3-(aminomethyl)phenyl]propanoic acid, 2-amino-3-(3-carboxyphenyl)propanoic acid, 2-amino-3-(4-nitrophenyl)propanoic acid, 2-amino-3-(4-aminophenyl)propanoic acid, 2-amino-3-(4-azidophenyl)propanoic acid, 2-amino-3-(4-cyanophenyl)propanoic acid, 2-amino-3-(4-acetophenyl)propanoic acid, 2-amino-3-(4-guanidinophenyl)propanoic acid, 2-amino-3-[4-(phenylazo)phenyl]propanoic acid, 2-amino-3-[4-(2-phenylethylenyl)phenyl]propanoic acid, 2-amino-3-(4-trialkylsilylphenyl)propanoic acid, 2-amino-3-(2,4-dimethylphenyl)propanoic acid, 2-amino-3-(2,3-dimethylphenyl)propanoic acid, 2-amino-3-(2,5-dimethylphenyl)propanoic acid, 2-amino-3-(3,5-dimethylphenyl)propanoic acid, 2-amino-3-(2,4,6-trimethylphenyl)propanoic acid, 2-amino-3-(3,4,5-trimethylphenyl)propanoic acid, 2-amino-3-(2,3,4,5,6-pentamethylphenyl)propanoic acid, 2-amino-3-(2,4,- difluorophenyl)propanoic acid, 2-amino-3-(3,4,-difluorophenyl)propanoic acid, 2-amino-3-(2,5,-difluorophenyl)propanoic acid, 2-amino-3-(2,6,-difluorophenyl)propanoic acid, 2-amino-3-(2,3,5,6-tetrafluorophenyl)propanoic acid, 2-amino-3-(3,5-dichloro-2,4,6-trifluorophenyl)propanoic acid, 2-amino-3-(2,3-difluorophenyl)propanoic acid, 2-amino-3-(2,3-bistrifluoromethylphenyl)propanoic acid, 2-amino-3-(2,4-bistrifluoromethylphenyl)propanoic acid, 2-amino-3-(2-chloro-5-trifluoromethylphenyl)propanoic acid, 2-amino-3-(2,5-difluorophenyl)propanoic acid, 2-amino-3-(2,3,4,5,6-pentafluorophenyl)propanoic acid, 2-amino-3-(2,3-dibromophenyl)propanoic acid, 2-amino-3-(2,5-dibromophenyl)propanoic acid, 2-amino-3-(3,4-dibromophenyl)propanoic acid, 2-amino-3-(3,4,5-triiodophenyl)propanoic acid, 2-amino-3-(2,3-dihydroxyphenyl)propanoic acid, 2-amino-3-(2,5-dihydroxyphenyl)propanoic acid, 2-amino-3-(2,6-dihydroxyphenyl)propanoic acid, 2-amino-3-(3-bromo-5-methoxyphenyl)propanoic acid, 2-amino-3-(2,5-dimethoxyphenyl)propanoic acid, 2-amino-3-(2,5-dimethoxy-4-methylphenyl)propanoic acid, 2-amino-3-(4-bromo-2,5-dimethoxyphenyl)propanoic acid, 2-amino-3-(3-carboxy-4-hydroxyphenyl)propanoic acid, 2-amino-3-(3-carboxy-4-aminophenyl)propanoic acid, 2-amino-3-(2-hydroxy-5-nitrophenyl)propanoic acid, 2-amino-3-(2-ethoxy-5-nitrophenyl)propanoic acid, 2-amino-3-(3,4,5-trimethoxyphenyl)propanoic acid, 2-amino-3-(4-azido-2-nitrophenyl)propanoic acid, 2-amino-3-(2-hydroxy-5-nitrophenyl)propanoic acid, 2-amino-3-(2,4-bis-trimethylsilylphenyl)propanoic acid, 2-amino-3-(4-hydroxy-3,5-di-t-butylphenyl)propanoic acid, 2-amino-3-(4-hydroxy-3-benzylphenyl)propanoic acid, 2-amino-3-(4-hydroxy-3-fluorophenyl)propanoic acid, 2-amino-3-(4-hydroxy-2,3,5,6-tetrafluorophenyl)propanoic acid, 2-amino-3-(4-hydroxy-3,5-dichlorophenyl)propanoic acid, 2-amino-3-(4-hydroxy-3-iodophenyl)propanoic acid, 2-amino-3-(4-hydroxy-3,5-diiodophenyl)propanoic acid, 2-amino-3-(4-hydroxy-2-hydroxyphenyl)propanoic acid, 2-amino-3-(4-hydroxy-3-hydroxymethylphenyl)propanoic acid, 2-amino-3-(4-hydroxy-2-hydroxy-6-methylphenyl)propanoic acid, 2-amino-3-(4-hydroxy-3-carboxyphenyl)propanoic acid, 2-amino-3-(4-hydroxy-3,5-dinitrophenyl)propanoic acid, substituted thyronines, 2-amino-3-(3,4-dihydroxy-2-chlorophenyl)propanoic acid, 2-amino-3-(3,4-dihydroxy-2-bromophenyl)propanoic acid, 2-amino-3-(3,4-dihydroxy-2-fluorophenyl)propanoic acid, 2-amino-3-(3,4-dihydroxy-2-nitrophenyl)propanoic acid, 2-amino-3-(3,4-dihydroxy-2-methylphenyl)propanoic acid, 2-amino-3-(3,4-dihydroxy-2-ethylphenyl)propanoic acid, 2-amino-3-(3,4-dihydroxy-2-isopropylphenyl)propanoic acid, 2-amino-3-(2-t-butyl-4,5-dihydroxyphenyl)propanoic acid, 2-amino-3-(3-fluoro-4,5-dihydroxyphenyl)propanoic acid, 2-amino-3-(2-fluoro-4,5-dihydroxyphenyl)propanoic acid, 2-amino-3-(2,5,6-trifluoro-3,4-dihydroxyphenyl)propanolc acid, 2-amino-3-(2,6-dibromo-3,4-dihydroxyphenyl)propanoic acid, 2-amino-3-(5,6-dibromo-3,4-dihydroxyphenyl)propanoic acid, 2-amino-3-(2,4,5-trihydroxyphenyl)propanoic acid, 2-amino-3-(2,3,4-trihydroxyphenyl)propanoic acid, 2-amino-3-(3,4-dihydroxy-5-methoxyphenyl)propanoic acid, 2-amino-3-methyl-3-phenylpropanoic acid, 2-amino-3-ethyl-3-phenylpropanoic acid, 2-amino-3-isopropyl-3-phenylpropanoic acid, 2-amino-3-butyl-3-phenylpropanoic acid, 2-amino-3-benzyl-3-phenylpropanoic acid, 2-amino-3-phenylethyl-3-phenylpropanoic acid, 2-amino-3-(4-chlorophenyl)-3-phenylpropanoic acid, 2-amino-3-(4-methoxyphenyl)-3-phenylpropanoic acid, 2-amino-3,3-diphenylpropanoic acid, 2-amino-3-[4-(N,N-diethylamino)phenyl]heptanoic acid, 2-amino-3-[4-(N,N-diethylamino)phenyl]pentanoic acid, 2-amino-3-(3,4-dimethoxyphenyl)pentanoic acid, 2-amino-3-(3,4-dihydroxyphenyl)pentanoic acid, 2-amino-3-methyl-3-phenylbutanoic acid, 2-amino-3-ethyl-3-phenylpentanoic acid, 2-amino-3-methyl-3-phenylpentanoic acid, 2-amino-3,3-diphenylbutanoic acid, 2-amino-3-fluoro-3-phenylpropanoic acid, 2-amino-3-methylene-3-phenylpropanoic acid, 2-amino-3-methylmercapto-3-phenylpropanoic acid, 2-amino-4-methylmercapto-4-phenylbutanoic acid, 2-amino-4-(3,4-dihydroxyphenyl)butanoic acid, 2-amino-5-(4-methoxyphenyl)pentanoic acid, 2-amino-4-phenylbutanoic acid, 2-amino-5-phenylpentanoic acid, 2-amino-3,3-dimethyl-5-phenylpentanoic acid, 2-amino-4-phenyl-3-butenoic acid, 2-amino-4-phenoxybutanoic acid, 2-amino-5-phenoxypentanoic acid, 2-amino-2-(indanyl)acetic acid, 2-amino-2-(1-tetralyl)acetic acid, 2-amino-4,4-diphenylbutanoic acid, 2-amino-2-(2-naphthyl)acetic acid, 2-amino-3-(1-naphthyl)propanoic acid, 2-amino-3-(1-naphthyl)pentanoic acid, 2-amino-3-(2-naphthyl)propanoic acid, 2-amino-3-(1-chloro-2-naphthyl)propanoic acid, 2-amino-3-(1-bromo-2-naphthyl)propanoic acid, 2-amino-3-(4-hydroxy-1-naphthyl)propanoic acid, 2-amino-3-(4-methoxy-1-naphthyl)propanoic acid, 2-amino-3-(4-hydroxy-2-chloro-1-naphthyl)propanoic acid, 2-amino-3-(2-chloro-4-methoxy-1-naphthyl)propanoic acid, 2-amino-2-(2-anthryl)acetic acid, 2-amino-3-(9-anthryl)propanoic acid, 2-amino-3-(2-fluorenyl)propanoic acid, 2-amino-3-(4-fluorenyl)propanoic acid, 2-amino-3-(carboranyl)propanoic acid, 3-methylproline, 4-methylproline, 5-methylproline, 4,4-dimethylproline, 4-fluoroproline, 4,4-difluoroproline, 4-bromoproline, 4-chloroproline, 4-aminoproline, 3,4-dehydroproline, 4-methylproline, 4-methyleneproline, 4-mercaptoproline, 4-(4-methoxybenzylmercapto)proline, 4-hydroxymethylproline, 3-hydroxyproline, 3-hydroxy-5-methylproline, 3,4-dihydroxyproline, 3-phenoxyproline, 2-aminoproline, 5-aminoproline, 3-carbamylalkylproline, 4-cyano-5-methyl-5-carboxyproline, 4,5-dicarboxyl-5-methylproline, 2-aziridinecarboxylic acid, 2-azetidinecarboxylic acid, 4-methyl-2-azetidinecarboxylic acid, pipecolic acid, 1,2,3,6-tetrahydropicolinic acid, 3,4-methyleneproline, 2,4-methyleneproline, 4-aminopipecolic acid, 5-hydroxypipecolic acid, 4,5-dihydroxypipecolic acid, 5,6-dihydroxy-2,3-dihydroindole-2-carboxylic acid, 1,2,3,4-tetrahydroquinoline-2-carboxylic acid, 6,7-dihydroxy-1,2,3,4-tetrahydroisoquinoline-3-carboxylic acid, 6-hydroxy-1-methyl-1,2,3,4-tetrahydroisoquinoline-3-carboxylic acid, 6,7-dihydroxy-1-methyl-1,2,3,4-tetrahydroisoquinoline-3-carboxylic acid, 1,3-oxazolidine-4-carboxylic acid, 1,2-oxazolidine-3-carboxylic acid, perhydro-1,4-thiazine-3-carboxylic acid, 2,2-dimethylthiazolidine-4-carboxylic acid, perhydro-1,3-thlazine-2-carboxylic acid, selenazolidine4-carboxylic acid, 2-phenylthiazolidine4-carboxylic acid, 2-(4-carboxylicyl)thiazolidine-4-carboxylic acid, 1,2,3,4,4a,9a-hexahydro-beta-carboline-3-carboxylic acid, 2,3,3a,8a-tetrahydropyrrolo(2,3b)indole-2-carboxylic acid, 2-amino-3-(2-pyridyl)propanoic acid, 2-amino-3-(3-pyridyl) propanoic acid, 2-amino-3-(4-pyridyl)propanoic acid, 2-amino-3-(2-bromo-3-pyridyl)propanoic acid, 2-amino-3-(2-bromo-4-pyridyl)propanoic acid, 2-amino-3-(2-bromo-5-pyridyl)propanoic acid, 2-amino-3-(2-bromo-6-pyridyl) propanoic acid, 2-amino-3-(2-chloro-3-pyridyl)propanoic acid, 2-amino-3-(2-chloro-4-pyridyl)propanoic acid, 2-amino-3-(2-chloro-5-pyridyl)propanoic acid, 2-amino-3-(2-chloro-6-pyridyl)propanoic acid, 2-amino-3-(2-fluoro-3-pyridyl)propanoic acid, 2-amino-3-(2-fluoro-4-pyridyl)

loropanoic acid, 2-amino-3-(2-fluoro-5-pyridyl)propanoic acid, 2-amino-3-(2-fluoro-6-pyridyl)proloanoic acid, 2-amino-3-(1,2-dihydro-2-oxo-3-pyridyl)propanoic acid, 2-amino-3-(1,2-dihydro-2-oxo4-pyridyl)propanoic acid, 2-amino-3-(1,2-dihydro-2-oxo-5-pyridyl)propanoic acid, 2-amino-3-(1,2-dihydro-2-oxo-6-pyridyl)propanoic acid, 2-amino-3-(5-hydroxy-2-pyridyl)propanoic acid, 2-amino-3-(5-hydroxy-6-iodo-2-pyridyl)propanoic acid, 2-amino-3-(3-hydroxy-4-oxo-1,4dihydro-1-pyridyl)propanoic acid, N-(5-caroxyl-5-aminopentyl)pyridinium chloride, 1,2,5-trimethyl-4-(2-amino-2-carboxy-1-hydroxyethyl) pyridinium chloride, 2-amino-2-(5-chloro-2-pyridyl)acetic acid, N-(3-amino-3-carboxypropyl)pyridinium chloride, 2-amino-3-(2-pyrryl)propanoic acid, 2-amino-3-(1-pyrryl) propanoic acid, 2-amino-4-(1-pyrryl)butanoic acid, 2-amino-5-(1-pyrryl)pentanoic acid, 2-amino-3-(5-imidazolyl)-3-methylpropanoic acid, 2-amino-3-(5-imidazolyl)-3-ethylpropanoic acid, 2-amino-3-hexyl-3-(5-imidazolyl)propanoic acid, 2-amino-3-hydroxy-3-(5-imidazolyl)propanoic acid, 2-amino-3-(4-nitro-5-imidazolyl)proloanoic acid, 2-amino-3-(4-methyl-5-imidazolyl)propanoic acid, 2-amino-3-(2-methyl-5-imidazolyl)propanoic acid, 2-amino-3-(4-fluoro-5-imidazolyl)propanoic acid, 2-amino-3-(2-fluoro-5-imidazolyl)propanoic acid, 2-amino-3-(2-amino-5-imidazolyl)propanoic acid, 2-amino-3-(2-phenylaza-5-imidazolyl)propanoic acid, 2-amino-3-(1-methyl-2-nitro-5-imidazolyl)propanoic acid, 2-amino-3-(1-methy14-nitro-5-imidazolyl)propanoic acid, 2-amino-3-(1-methyl-5-nitro-5-imidazolyl)propanoic acid, 2-amino-3-(2-mercapto-5-imidazolyl)propanoic acid, 2-amino-4-(5-imidazolyl) butanoic acid, 2-amino-3-(1-imidazolyl)propanoic acid, 2-amino-3-(2-imidazolyl)propanoic acid, 2-amino-(1-pyrazolyl)propanoic acid, 2-amino-(3-pyrazolyl)propanoic acid, 2-amino-(3,5-dialkyl-4-pyrazolyl)propanoic acid, 2-amino-3-(3-amino-1,2,4-triazol-1-yl)propanoic acid, 2-amino-3-(tetrazol-5-yl)propanoic acid, 2-amino-4-(5-tetrazolyl)butanoic acid, 2-amino-3-(6-methyl-3-indolyl) propanoic acid, 2-amino-3-(4-fluoro-3-indolyl)propanoic acid, 2-amino-3-(5-fluoro-3-indolyl)propanoic acid, 2-amino-3-(6-fluoro-3-indolyl)propanoic acid, 2-amino-3-(4,5,6,7-tetrafluoro-3-indolyl)propanoic acid, 2-amino-3-(5-chloro-3-indolyl)propanoic acid, 2-amino-3-(6-chloro-3-indolyl)propanoic acid, 2-amino-3-(7-chloro-3-indolyl) propanoic acid, 2-amino-3-(5-bromo-3-indolyl)propanoic acid, 2-amino-3-(7-bromo-3-indolyl)propanoic acid, 2-amino-3-(2-hydroxy-3-indolyl)propanoic acid, 2-amino-3-(5-hydroxy-3-indolyl)propanoic acid, 2-amino-3-(7-hydroxy-3-indolyl)propanoic acid, 2-amino-3-(2-alkylmercapto-3-indolyl)propanoic acid, 2-amino-3-(7-amino-3-indolyl)propanoic acid, 2-amino-3-(4-nitro-3-indolyl)propanoic acid, 2-amino-3-(7-nitro-3-indolyl) propanoic acid, 2-amino-3-(4-carboxy-3-indolyl)propanoic acid, 2-amino-3-(3-indolyl)butanoic acid, 2-amino-3-(2,3-dihydro-3-indolyl)propanoic acid, 2-amino-3-(2,3-dihydro-2-oxo-3-indolyl)propanoic acid, 2-amino-3-alkylmercapto-3-(3-indolyl)propanoic acid, 2-amino-3-(4-aza-3-indolyl) propanoic acid, 2-amino-3-(7-aza-3-indolyl)propanoic acid, 2-amino-3-(7-aza-6-chloro-4-methyl-3-indolyl)propanoic acid, 2-amino-3-(2,3-dihydrobenzofuran-3-yl)propanoic acid, 2-amino-3-(3-methyl-5-7-dialkylbenzofuran-2-yl) propanoic acid, 2-amino-3-(benzothiophen-3-yl)propanoic acid, 2-amino-3-(5-hydroxybenzothiophen-3-yl)propanoic acid, 2-amino-3-eoenzoselenol-3yl)propanoic acid, 2-amino-3-quinolylpropanoic acid, 2-amino-3-(8-hydroxy-5-quinolyl)propanoic acid, 2-amino-2-(5,6,7,8-tetrahydroquinol-5-yl)acetic acid, 2-amino-3-(3-coumarinyl)propanoic acid, 2-amino-2-(benzisoxazol-3-yl) acetic acid, 2-amino-2-(5-methylbenzisoxazol-3-yl)acetic acid, 2-amino-2-(6-methylbenzisoxazol-3-yl)acetic acid, 2-amino-2-(7-methylbenzisoxazol-3-yl)acetic acid, 2-amino-2-(5-bromobenzisoxazol-3-yl)acetic acid, 2-amino-3-(benzimidazol-2-yl)propanoic acid, 2-amino-3-(5,6-dichlorobenzimidazol-2-yl)propanoic acid, 2-amino-3-(5,6-dimethylbenzimidazol-2-yl)propanoic acid, 2-amino-3-(4,5,6,7-hydrobenzirnidazol-2-yl)propanoic acid, 2-amino-2-(benzimidazol-5-yl)acetic acid, 2-amino-2-(1,3-dihydro-2,2-dioxoisobenzothiophen-5-yl)acetic acid, 2-amino-2-(1,3-dihydro-2,2-dioxo-2,1,3-benzothiadiazol-5-yl)acetic acid, 2-amino-2-(2-oxobenzimidazol-5-yl)acetic acid, 2-amino-3-(4-hydroxybenzothiazol-6-yl)propanoic acid, 2-amino-3-(benzoxazol-2-yl)propanoic acid, 2-amino-3-(benzothiazol-2-yl)propanoic acid, 2-amino-3-(9-adeninyl)propanoic acid, 2-amino-2-(6-chloro-9-purinyl)acetic acid, 2-amino-2-(6-amino-9-purinyl)acetic acid, 2-amino-3-(6-purinyl) propanoic acid, 2-amino-3-(8-theobrominyl)propanoic acid, 2-amino-2-(1-uracilyl)acetic acid, 2-amino-2-(1-cytosinyl) acetic acid, 2-amino-3-(1-uracilyl)propanoic acid, 2-amino-3-(1-cytosinyl)propanoic acid, 2-amino-4-(1-pyrimidinyl) butanoic acid, 2-amino-4-(4-amino-1-pyrimidinyl)butanoic acid, 2-amino-4-(4-hydroxy-1-pyrimidinyl)butanoic acid, 2-amino-5-(1-pyrimidinyl)pentanoic acid, 2-amino-5-(4-amino-1-pyrimidinyl)pentanoic acid, 2-amino-5-(4-hydroxy-1-pyrimidinyl)pentanoic acid, 2-amino-3-(5-pyrimidinyl)propanoic acid, 2-amino-3-(6-uracilyl) propanoic acid, 2-amino-3-(2-pyrimidinyl)propanoic acid, 2-amino-3-(6-amino-4-chloro-2-pyrimidinyl)propanoic acid, 2-amino-3-(4-hydroxy-2-pyrimidinyl)propanoic acid, 2-amino-3-(2-amino-4-pyrimidinyl)propanoic acid, 2-amino-3-(4,5-dihydroxypyrimidin-2-yl)propanoic acid, 2-amino-3-(2-thiouracil-6-yl)propanoic acid, 2-amino-2-(5-alkyl-2-tetrahydrofuryl)acetic acid, 2-amino-2-(5-methyl-2,5-dihydro-2-furyl)acetic acid, 2-amino-2-(5-alkyl-2-furyl) acetic acid, 2-amino-2-(2-furyl)acetic acid, 2-amino-2-(3-hydroxy-5-methyl-4-isoxazolyl)acetic acid, 2-amino-3-(4-bromo-3-hydroxy-5-isoxazolyl)propanoic acid, 2-amino-3-(4-methyl-3-hydroxy-5-isoxazolyl)propanoic acid, 2-amino-3-(3-hydroxy-5-isoxazolyl)propanoic acid, 2-amino-2-(3-chloro-D$^2$-isoxazolin-5-yl)acetic acid, 2-amino-2-(3-oxo-5-isoxazolidinyl)acetic acid, 2-amino-3-(3,5-dioxo-1,2,4-oxadiazolin-2-yl)propanoic acid, 2-amino-3-(3-phenyl-5-isoxazolyl)propanoic acid, 2-amino-3-[3-(4-hydroxyphenyl)-1,2,4-oxadiazol-5-yl]propanoic acid, 2-amino-3-(2-thienyl)propanoic acid, 2-amino-2-(2-furyl) acetic acid, 2-amino-2-(2-thienyl)acetic acid, 2-amino-2-(2-thiazolyl)acetic acid, 2-amino-3-(2-thiazolyl)propanoic acid, 2-amino-4-(4-carboxy-2-thiazolyl)butanoic acid, 2-amino-3-(4-thiazolyl)propanoic acid, 2-amino-3-(2-selenolyl)propanoic acid, 2-amino-3-(2-amino-4-selenolyl) propanoic acid, or 2-amino-3-(β-ribofuranosyl)propanoic acid.

3. A compound of claim 2 wherein A is an amino acid residue or peptide having from 2-20 amino acid residues selected from Ala, Arg, Asn, Asp, Aze, Cys, Gln, Glu, Gly, His, ile, Irg, Leu, Lys, Met, Orn, Phe, Phe (4-fluoro), Pro, Sar, Ser, Thr, Trp, Tyr or Val.

4. A compound of claim 3 wherein A is selected from Pro or (D)Phe-Pro.

5. A compound of claim 2 selected from the group consisting of:

Ac-(D)Phe-Pro-NHCH[(CH$_2$)$_3$-NHC(NH)H]B(OH)$_2$,
Boc-(D)Phe-Pro-NHCH[(CH$_2$)$_3$-NHC(NH)H]B(OH)$_2$,.
Ac-(D)Phe-Pro-boroPhe(p-CN)-C$_{10}$H$_{16}$,
Boc-(D)Phe-Pro-boroPhe(m-CN)-C$_{10}$H$_{16}$, N,N-(CH₃)₂-(D)Phe-Pro-boroPhe(m-CN)—OH·HCl,
Ac-(D)Phe-Pro-boroPhe(m-CN)—OH·HCl,
Ms-(D)Phe-Pro-boroPhe(m-CN)—OH·HCl,
Boc-(D)Thiazolylalanine-Pro-boroPhe(m-CN)-C₁₀C₁₆,
Boc-(D)3-Pyridylalanine-Pro-boroPhe(m-CN)-C₁₀C₁₆,
Ms-(D)3-Pyridylalanine-Pro-boroPhe(m-CN)-C₁₀H₁₆,
Boc-(D)2-Pyridylalanine-Pro-boroPhe(m-CN)-C₁₀H₁₆,
Boc-(D)2-Thienylalanine-Pro-boroPhe(m-CN)-C₁₀H₁₆,
Ms-(D)2-Thienylalanine-Pro-boroPhe(m-CN)-C₁₀H₁₆,
Boc-(D)Phe-Aze-boroPhe(m-CN)C₁₀H₁₆,
PhCH₂SO₂-(D)Phe-Pro-boroOrn(CH=NH)—OH·HCl,
CH₃CH₂CH₂SO₂-(D)Phe-Pro-b oroOrn(CH=NH)—OH·HCl,
Ac-(D)Phe-Sar-boroOrn(CH=NH)—OH·HCl,
Boc-(D)Phe-Sar-boroPhe(mCN)-C₁₀H₁₆,
Boc-(D)Phe-Aze-boroOrn(CH=NH)—OH·HCl,
4-(Phenyl)benzoyl-boroOrn(CH=NH)-C₁₀H₁₆·HCl,
Ac-(D)Phe-Pro-boroOrn(CH=NH)]-C₁₀H₁₆·HCl,
Boc-Pro-b oroOrn(CH=NH)-C₁₀H₁₆·HCl,
Boc-(D)Phe-Pro-boroOrn(CH=NH)]-C₁₀H₁₆·0.5 HCl·0.5 BSA,
H-(D)Phe-Pro-boroOrn(CH=NH)]-C₁₀H₁₆·0.5 HCl·0.5 BSA,
H-(D)Phe-Pro-boroOrn(CH=NH)]—OH·0.65 HCl·0.35 BSA,
H-boroPhe(mCN)-C₁₀H₁₆·HCl,
Ac-(D)Phe-Pro-boroPhe-(m-CN)-C₁₀H₁₆,
H-(D)Phe-Pro-boroPhe(m-CN)-C₁₀H₁₆·HCl,
H-(D)Phe-Pro-boroFhe(m-CN)—OH·HCl,
N,N-(CH₃)₂-(D)Phe-Pro-boroPhe(m-CN)—OH·HCl (ISOMER I),
N-CH₃-(D)Phe-Pro-boroPhe(m-CN)-C₁₀H₁₆·HCl,
H-Pro-boroPhe(m-CN)-C₁₀H₁₆·HCl,
H-(D)Thiazolylalanine-Pro-boroPhe(m-CN)-C₁₀H₁₆·HCl,
H-(D)3-Pyridylalanine-Pro-boroPhe(m-CN)-C₁₀H₁₆ HCl,
Ms-(D)Thiazolylalanine-Pro-boroPhe(m-CN)-C₁₀H₁₆,
N-Boc-N-CH₃-(D)Phe-Pro-boroPhe(m-CN)-C₁₀H₁₆,
Ac-Pro-boroPhe(m-CN)-C₁₀H₁₆,
H-(D)2-Pyridylalanine-Pro-boroPhe(m-CN)-C₁₀H₁₆·HCl,
H-(D)2-Thienylalanine-Pro-boroPhe(m-CN)-C₁₀H₁₆·HCl,
Ms-(D)2-Pyridylalanine-Pro-boroPhe(m-CN)-C₁₀H₁₆,
(2-Pyrimidylthio)acetyl-Pro-boroPhe(m-CN)-C₁₀H₁₆,
trans-3-(3-pyridyl)acryl-Pro-boroPhe(m-CN)-C₁₀H₁₆,
(4-Pyridylthio)acetyl-Pro-boroPhe(m-CN)-C₁₀H₁₆,
Succinyl-(D)Phe-Pro-boroPhe(m-CN)—OH,
3-Pyridylpropionyl-Pro-boroPhe(m-CN)-C₁₀H₁₆,
Boc-(D)Phe-Aze-boroPhe(m-CN)-C₁₀H₁₆,
H-(D)Phe-Aze-boroPhe(m-CN)-C₁₀H₁₆·HCl,
Hydrocirmamoyl-Pro-boroOrn(CH=NH)]OH·BSA,
M-s-(D)Phe-Pro-boroOrn(CH=NH)—OH·HCl,
PhSO2-(D)Phe-Pro-boroOrn(CH=NH)—OH·HCl,
Ms-(D)Phe(4-fluoro)-Pro-boroOrn(CH=NH)—OH·HCl,
PhCH₂SO₂-(D)Phe-Pro-boroOrn(CH=NH)—OH·HCl,
CH₃CH₂CH₂SO₂-(D)Phe-Pro-boroOm(CH=NH)—OH·HCl,
CH₃(CH₂)₃SO₂-(D)Phe-Pro-boroOrn(CH=NH)—OH·HCl,
Z-(D)Phe-Pro-boroOrn(CH=NH)—OH·HCl,
Boc-(D)Phe-Pro-boroGly[(CH₂)₃—ONH₂]—OH·HCl,
PhCH₂SO₂-(D)Phe-Pro-boroGly[(CH₂)₃—ONH₂]-C₁₀H₁₆·HCl,
Boc-(D)Phe-Pro-boroGly[(CH₂)₃—ONHC(=NH)NH₂]-C₁₀H₁₆·HCl,
Boc-(D)Phe-Pro-boroOrn(CONH₂)-C₁₀H₁₆,
H-(D)Phe-Pro-boroOrn(CONH₂)-C₁₀H₁₆·HCl,
PhCH₂SO₂-(D)Phe-Pro-boroOrn(CONH₂)-C₁₀H₁₆,
HOOCCH₂-(D)Phe-Pro-boroOrn(CONH₂)-C₁₀H₁₆·HCl,
Ac-(D)Phe-Pro-NH-CH[CH₂(4-amino-cyclohexyl)]BO₂-C₁₀H₁₆,
Boc-(D)Phe-Pro-NH-CH[CH₂(4-amino-cyclohexyl)]BO₂-C₁₀H₁₆,
Boc-(D)Phe-Pro-NH-CH[4-amino-cyclohexyl]BO₂-C₁₀H₁₆,
Boc-(D)Phe-Pro-NH-CH[CH₂(4-hydoxy-cyclohexyl)]BO₂-C₁₀H₁₆,
Boc-(D)Phe-Pro-NH-CH[CH₂(4-guanidino-cyclohexyl)]BO₂-C₁₀H₁₆ and
H-(D)Phe-Pro-boroPhe(mCOOMe)-C₁₀H₁₆·HCl.

6. A pharmaceutical composition comprising a pharmaceutically suitable carrier and a compound of claim 1.

7. A pharmaceutical composition comprising a pharmaceutically suitable carrier and a compound of claim 2.

8. A pharmaceutical composition comprising a pharmaceutically suitable carrier and a compound of claim 3.

9. A pharmaceutical composition comprising a pharmaceutically suitable carrier and a compound of claim 4.

10. A pharmaceutical composition comprising a pharmaceutically suitable carrier and a compound of claim 5.

11. A method of treating thrombosis in a warm blooded animal comprising administering to said animal in need of such treatment an effective amount of a compound of claim 1.

12. A method of treating thrombosis in a warm blooded animal comprising administering to said animal in need of such treatment an effective amount of a compound of claim 2.

13. A method of treating thrombosis in a warm blooded animal comprising administering to said animal in need of such treatment an effective amount of a compound of claim 3.

14. A method of treating thrombosis in a warm blooded animal comprising administering to said animal in need of such treatment an effective amount of a compound of claim 4.

15. A method of treating thrombosis in a warm blooded animal comprising administering to said animal in need of such treatment an effective amount of a compound of claim 5.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

(A) LENGTH: 12
(B) TYPE: amino acids
(C) TOPOLOGY: linear (ii) MOLECULE TYPE: peptide (vi) ORIGINAL SOURCE: synthetic (ix) FEATURE:
(D) OTHER INFORMATION: Example Number 98

(xi) SEQUENCE DESCRIPTION: SEQ ID NO:1:

```
Xaa  Xaa  Asn  Leu  Xaa  Asn  Leu  Xaa  Asn  Leu  Xaa  Asn
 1                    5                        10
```

(2) INFORMATION FOR SEQ ID NO:2:

(i) SEQUENCE CHARACTERISTICS:
(A) LENGTH: 12
(B) TYPE: amino acids
(C) TOPOLOGY: linear (ii) MOLECULE TYPE: peptide (vi) ORIGINAL SOURCE: synthetic (ix) FEATURE:
(D) OTHER INFORMATION: Example Number 99

(xi) SEQUENCE DESCRIPTION: SEQ ID NO:2:

```
Leu  Xaa  Asn  Leu  Xaa  Asn  Leu  Xaa  Asn  Leu  Xaa  Asn
 1                    5                        10
```

(2) INFORMATION FOR SEQ ID NO:3:

(i) SEQUENCE CHARACTERISTICS:
(A) LENGTH: 12
(B) TYPE: amino acids
(C) TOPOLOGY: linear (ii) MOLECULE TYPE: peptide (vi) ORIGINAL SOURCE: synthetic (ix) FEATURE:
(D) OTHER INFORMATION: Example Number 100

(xi) SEQUENCE DESCRIPTION: SEQ ID NO:3:

```
Xaa  Ser  Asn  Leu  Ser  Asn  Leu  Ser  Asn  Leu  Ser  Asn
 1                    5                        10
```

(2) INFORMATION FOR SEQ ID NO:4:

(i) SEQUENCE CHARACTERISTICS:
(A) LENGTH: 12
(B) TYPE: amino acids
(C) TOPOLOGY: linear (ii) MOLECULE TYPE: peptide (vi) ORIGINAL SOURCE: synthetic (ix) FEATURE:
(D) OTHER INFORMATION: Example Number 101

(xi) SEQUENCE DESCRIPTION: SEQ ID NO:4:

```
Leu  Ser  Asn  Leu  Ser  Asn  Leu  Ser  Asn  Leu  Ser  Asn
 1                    5                        10
```